US009857374B2

(12) United States Patent
LaBaer et al.

(10) Patent No.: US 9,857,374 B2
(45) Date of Patent: Jan. 2, 2018

(54) BIOMARKERS FOR THE EARLY DETECTION OF BREAST CANCER

(75) Inventors: Joshua LaBaer, Chandler, AZ (US); Karen Sue Anderson, Chestnut Hill, MA (US); Garrick Wallstrom, Mesa, AZ (US); Sahar Sibani, La Mesa, CA (US); Niroshan Ramachandran, San Marcos, CA (US)

(73) Assignees: Arizona Board of Regents, A Body Corporate Acting For and On Behalf of Arizona State University, Scottsdale, AZ (US); President and Fellows of Harvard College, Cambridge, MA (US); Dana Farber Cancer Institute, Inc., Boston, MA (US)

( * ) Notice: Subject to any disclaimer, the term of this patent is extended or adjusted under 35 U.S.C. 154(b) by 64 days.

(21) Appl. No.: 13/809,695

(22) PCT Filed: Aug. 15, 2011

(86) PCT No.: PCT/US2011/047741
§ 371 (c)(1),
(2), (4) Date: Feb. 27, 2013

(87) PCT Pub. No.: WO2012/021887
PCT Pub. Date: Feb. 16, 2012

(65) Prior Publication Data
US 2013/0150259 A1 Jun. 13, 2013

Related U.S. Application Data

(60) Provisional application No. 61/373,359, filed on Aug. 13, 2010.

(51) Int. Cl.
*A61K 45/00* (2006.01)
*A61K 39/00* (2006.01)
*G01N 33/574* (2006.01)
*C12Q 1/68* (2006.01)

(52) U.S. Cl.
CPC ..... *G01N 33/57415* (2013.01); *C12Q 1/6886* (2013.01); *C12Q 2600/158* (2013.01)

(58) Field of Classification Search
CPC .......................... G01N 33/5745; C12Q 1/6886
See application file for complete search history.

(56) References Cited

U.S. PATENT DOCUMENTS

| 9,141,756 B1* | 9/2015 | Hillis .................. G06F 19/12 |
| 2004/0048256 A1* | 3/2004 | Agee et al. ................... 435/6 |
| 2009/0136917 A1* | 5/2009 | Szalay .................. C07K 14/005 435/5 |
| 2010/0159469 A1 | 6/2010 | Harris et al. | |

FOREIGN PATENT DOCUMENTS

| WO | 03/012067 A2 | 2/2003 |
| WO | 2005/010180 A1 | 2/2005 |
| WO | 2007/147265 A1 | 12/2007 |
| WO | 2008/021290 A2 | 2/2008 |
| WO | 2008030845 A2 | 3/2008 |
| WO | 2008/106660 A1 | 9/2008 |
| WO | 2009/108917 A2 | 9/2009 |
| WO | 2010/083252 A2 | 7/2010 |

OTHER PUBLICATIONS

Cameron et al., (PLos ONE. Jan. 2009,4(1):e403(8 pages) doi:10.1371/journal.pone.0004303).*
Anderson, Karen S., et al., "Protein Microarray Signature of Autoantibody Biomarkers for Early Detection of Breast Cancer," J. Proteome Res., Jan. 2011, pp. 85-96, vol. 10, No. 1.
Anderson, Karen S., et al., In "Using custom protein microarrays to identify autoantibody biomarkers for the early detection of breast cancer," San Antonio Breast Cancer Symposium, San Antonio, TX, 2008. (abstract).
Anderson, Karen S., et al., "Application of protein microarrays for multiplexed detection of antibodies to tumor antigens in breast cancer." J. Proteome Res., Apr. 2008, pp. 1490-1499, vol. 7, No. 4.
Anderson, Karen S., et al., "The sentinel within: exploiting the immune system for cancer biomarkers," J. Proteome Res., Jul.-Aug. 2005, pp. 1123-1133, vol. 4, No. 4.
Anderson, N. Leigh, et al., "The human plasma proteome: history, character, and diagnostic prospects," Mol. Cell. Proteomics, Nov. 2002, pp. 845-867, vol. 1, No. 11.
Baugher, Paige J., et al., "Rac1 and Rac3 isoform activation is involved in the invasive and metastatic phenotype of human breast cancer cells," Breast Cancer Res., 2005, pp. R965-R974, vol. 7, No. 6.
Breiman, Leo, "Random Forests." Mach. Learn., 2001, pp. 5-32, vol. 45.
Bouwman, Kerri, et al., "Microarrays of tumor cell derived proteins uncover a distinct pattern of prostate cancer serum immunoreactivity," Proteomics, Nov. 2003, pp. 2200-2207, vol. 3, No. 11.
Chapman, C., et al., "Autoantibodies in breast cancer: their use as an aid to early diagnosis," Ann. Oncol., May 2007, pp. 868-873, vol. 18, No. 5.
Chatterjee, Madhumita, et al., "Diagnostic markers of ovarian cancer by high-throughput antigen cloning and detection on arrays," Cancer Res., Jan. 2006, pp. 1181-1190, vol. 66, No. 2.
Chen, Kai-Yun, et al., "The role of tyrosine kinase Etk/Bmx in EGF-induced apoptosis of MDAMB-468 breast cancer cells," Oncogene, 2004, pp. 1854-1862, vol. 23, No. 10.
Chen, Yupeng, et al., "The molecular mechanism governing the oncogenic potential of SOX2 in breast cancer," J. Biol. Chem., Jun. 2008, pp. 17969-17978, vol. 283, No. 26.
Chen, Guoan, et al., "Autoantibody profiles reveal ubiquilin 1 as a humoral immune response target in lung adenocarcinoma," Cancer Res., Apr. 2007, pp. 3461-3467, vol. 67, No. 7.
Csepregi, Antal, et al., "Characterization of a lipoyl domain-independent B-cell autoepitope on the human branched-chain acyltransferase in primary biliary cirrhosis and overlap syndrome with autoimmune hepatitis," Clin. Dev. Immunol., Jun.-Dec. 2003, pp. 173-181, vol. 10, Nos. 2-4.

(Continued)

*Primary Examiner* — Cherie M Stanfield
(74) *Attorney, Agent, or Firm* — McDonnell Boehnen Hulbert & Berghoff LLP

(57) ABSTRACT

The present invention provides reagents and methods for breast cancer detection.

8 Claims, No Drawings

(56) References Cited

OTHER PUBLICATIONS

Desmetz, Caroline, et al., "Identification of a new panel of serum autoantibodies associated with the presence of in situ carcinoma of the breast in younger women," Clin. Cancer Res., Jul. 2009, pp. 4733-4741, vol. 15, No. 14.

Edwards, Brenda K., et al., "Annual report to the nation on the status of cancer, 1975-2002, featuring population-based trends in cancer treatment," J. Natl. Cancer Inst., Oct. 2005, pp. 1407-1427, vol. 97, No. 19.

Efron, B., "Bootstrap Methods: Another Look at the Jackknife," Ann. Stat., 1979, pp. 1-26, vol. 7, No. 1.

Esserman, M.D., Laura, et al., "Rethinking screening for breast cancer and prostate cancer," J. Am. Med. Assoc., Oct. 2009, pp. 1685-1692, vol. 302, No. 15.

Esserman, M.D., Laura, et al., "A role for biomarkers in the screening and diagnosis of breast cancer in younger women," Expert Rev. Mol. Diagn., Sep. 2007, pp. 533-544, vol. 7, No. 5.

Forti, Stefania, et al., "Identification of breast cancer-restricted antigens by antibody screening of SKBR3 cDNA library using a preselected patient's serum," Breast Cancer Res. Treat., Jun. 2002, pp. 245-256, vol. 73, No. 3.

Fossa, Alexander, et al., "Serological cloning of cancer/testis antigens expressed in prostate cancer using cDNA surface display," Cancer Immunol. Immunother., May 2004, pp. 431-438, vol. 53, No. 5.

Gnjatic, Sacha, et al., "Seromic profiling of ovarian and pancreatic cancer," Proc. Natl. Acad. Sci., Mar. 2010, pp. 5088-5093, vol. 107, No. 11.

Grzmil, Michal, et al., "An oncogenic role of eIF3e/INT6 in human breast cancer," Oncogene, Jul. 2010, pp. 4080-4089, vol. 29, No. 28.

Güre, Ali O., et al., "Serological identification of embryonic neural proteins as highly immunogenic tumor antigens in cell lung cancer," Proc. Natl. Acad. Sci. U.S.A., Apr. 2000, pp. 4198-4203, vol. 97, No. 8.

Güre, Ali O., et al., "Human lung cancer antigens recognized by autologous antibodies: definition of a novel cDNA derived from the tumor suppressor gene loc us on chromosome 3p21.3," Cancer Res., Mar. 1998, pp. 1034-1041, vol. 58, No. 5.

Harris, Lyndsay, et al., "American Society of Clinical Oncology 2007 update of recommendations for the use of tumor markers in breast cancer," J. Clin. Oncol., Nov. 2007, pp. 5287-5312, vol. 25, No. 33.

Hartmann, Lynn C., et al., "Benign breast disease and the risk of breast cancer," N. Engl. J. Med., Jul. 2005, pp. 229-237, vol. 353, No. 3.

Hattori, Takako, et al., "Rheumatoid arthritis-related antigen 47 kDa (RAA47) is a product of colligin-2 and acts as a human HSP47," J. Bone Miner. Metab., 2000, pp. 328-334, vol. 18, No. 6.

Hodi, F. Stephen, et al., "ATP6S1 elicits potent humoral responses associated with immunemediated tumor destruction," Proc. Natl. Acad. Sci., May 2002, pp. 6919-6924, vol. 99, No. 10.

Hudson, Michael E., et al., "Identification of differentially expressed proteins in ovarian cancer using high-density protein microarrays," Proc. Natl. Acad. Sci. U.S.A., Oct. 2007, pp. 17494-17499, vol. 104, No. 44.

Huttenhower, Curtis, et al., "Exploring the human genome with functional maps," Genome Res., Jun. 2009, pp. 1093-1106, vol. 19, No. 6.

Iejima, Daisuke, et al., "FRS2beta, a potential prognostic gene for non-small cell lung cancer, encodes a feedback inhibitor of EGF receptor family members by ERK binding," Oncogene, May 2010, pp. 3087-3099, vol. 29, No. 21.

Jäger, Dirk, et al., "Identification of a tissue-specific putative transcription factor in breast tissue by serological of a breast cancer library," Cancer Res., Mar. 2001, pp. 2055-2061, vol. 61, No. 5.

Jäger, Dirk, et al., Antibodies and vaccines—hope or illusion, Breast, Dec. 2005, pp. 631-635, vol. 14, No. 6.

Jäger, Dirk, et al., Identification of tumorrestricted antigens NY-BR-1, SCP-1, and a new cancer/testis-like antigen NW-BR-3 by serological screening of a testicular library with breast cancer serum, Cancer Immun., Jun. 2002, p. 5, vol. 2.

Joos, Thomas O., et al., "Miniaturised multiplexed immunoassays," Curr. Opin. Chem. Biol., Feb. 2002, pp. 76-80, vol. 6, No. 1.

Kano, Satoshi, et al., "Tripartite motif protein 32 facilitates cell growth and migration via degradation of Abl-interactor 2," Cancer Res., Jul. 2008, pp. 5572-5580, vol. 68, No. 14.

Koziol, James A., et al., "Recursive partitioning as an approach to selection of immune markers for tumor diagnosis," Clin. Cancer Res., Nov. 2003, pp. 5120-5126, vol. 9, No. 14.

Kwok, Sukyee, et al., "Transforming growth factorbeta1 regulation of ATF-3 and identification of ATF-3 target genes in breast cancer cells," J. Cell. Biochem., Oct. 2009, pp. 408-414, vol. 108, No. 2.

Lichtenfels, Rudolf, et al., "Identification of metabolic enzymes in renal cell carcinoma utilizing PROTEOMEX analyses," Biochim. Biophys. Acta., Mar. 2003, pp. 21-31, vol. 1646, Nos. 1-2.

MacBeath, Gavin, et al., "Printing proteins as microarrays for high-throughput function determination," Science, Sep. 2000, pp. 1760-1763, vol. 289, No. 5485.

Mahul-Mellier, Anne-Laure, et al., "Alix and ALG-2 are involved in tumor necrosis factor receptor 1-induced cell death," J. Biol. Chem., Dec. 2008, pp. 34954-34965, vol. 283, No. 50.

Marchese, Rocio D., et al., "Optimization and validation of a multiplex, electrochemiluminescence-based detection assay for the quantitation of immunoglobulin G serotype-specific antipneumococcal antibodies in human serum," Clin. Vaccine Immunol., Mar. 2009, pp. 387-396, vol. 16, No. 3.

McClish, Donna K., "Analyzing a portion of the ROC curve," Med. Decis. Making, Jul.-Sep. 1989, pp. 190-195, vol. 9, No. 3.

Minenkova, Olga, et al., "Identification of tumorassociated antigens by screening phage-displayed human cDNA libraries with sera from tumor patients," Int. J. Cancer, Sep. 2003, pp. 534-544, vol. 106, No. 4.

Mira, Jean-Paul, et al., "Endogenous, hyperactive Rac3 controls proliferation of breast cancer cells by a p21-activated kinase-dependent pathway," Proc. Natl. Acad. Sci., Jan. 2000, pp. 185-189, vol. 97, No. 1.

Nese, M.D., Nalan, et al., "Comparison of the desmoplastic reaction and invading ability in invasive ductal carcinoma of the breast and prostatic adenocarcinoma based on the expression of heat shock protein 47 and fascin," Anal. Quant. Cytol. Histol., Apr. 2010, pp. 90-101, vol. 32, No. 2.

Palijan, Ana, et al., "Ligand-dependent corepressor LCoR is an attenuator of progesterone-regulated gene expression," J. Biol. Chem., Oct. 2009, pp. 30275-30287, vol. 284, No. 44.

Parkin, D. Max, et al., "Global cancer statistics, 2002," CA Cancer J. Clin., Mar.-Apr. 2005, pp. 74-108, vol. 55, No. 2.

Petricoin, Emmanuel, et al., "Clinical proteomics: revolutionizing disease detection and patient tailoring therapy," J. Proteome Res., Mar.-Apr. 2004, pp. 209-217, vol. 3, No. 2.

Qian, Jun, et al., "[Identification of digital differential expression patterns of a novel human gene (UBAP1) by an expressed sequence tag strategy]," [Ai zheng =Chinese Journal of Cancer], 2002, pp. 225-228, vol. 21, No. 3. (Abstract and figures translated).

Qiu, Ji, et al., "Development of natural protein microarrays for diagnosing cancer based on an antibody response to tumor antigens," J. Proteome Res., Mar.-Apr. 2004, pp. 261-267, vol. 3, No. 2.

Ramachandran, Niroshan, et al., "Self-assembling protein microarrays," Science, Jul. 2004, pp. 86-90, vol. 305, No. 5680.

Ramachandran, Niroshan, et al., "Next-generation highdensity self-assembling functional protein arrays," Nat. Methods, Jun. 2008, pp. 535-538, vol. 5, No. 6.

Ramachandran, Niroshan, et al., Tracking humoral responses using self assembling protein microarrays, Proteomics Clin. Appl., Oct. 2008, pp. 1518-1527, vol. 2, Nos. 10-11.

Richardson, Andrea L., et al., "X chromosomal abnormalities in basal-like human breast cancer," Cancer Cell, Feb. 2006, pp. 121-132, vol. 9, No. 2.

(56) References Cited

OTHER PUBLICATIONS

Robinson, William H., et al., "Autoantigen microarrays for multiplex characterization of autoantibody responses," Nat. Med., Mar. 2002, pp. 295-301, vol. 8, No. 3.
Schmoor, C., et al., "Long-term prognosis of breast cancer patients with 10 or more positive lymph nodes treated with CMF." Eur. J. Cancer, Jun. 2001, pp. 1123-1131, vol. 37, No. 9.
Sioud, Mouldy, et al., "Profiling the immune response in patients with breast cancer by phage-displayed cDNA libraries," Eur. J. Immunol., Mar. 2001, pp. 716-725, vol. 31, No. 3.
Stockert, Elisabeth, et al., "A survey of the humoral immune response of cancer patients to a panel of human tumor antigens," J. Exp. Med., Apr. 1998, pp. 1349-1354, vol. 187, No. 8.
Stoll, Dieter, et al., "Protein microarray technology," Front. Biosci., Jan. 2002, pp. c13-c32, vol. 7.
Storey, John D., "A direct approach to false discovery rates," J. R. Stat. Soc. B, 2002, pp. 479-498, vol. 64, Pt. 3.
Tamimi, Rulla M., "Endogenous hormone levels, mammographic density, and subsequent risk of breast cancer in postmenopausal women," J. Natl. Cancer Inst., Aug. 2007, pp. 1178-1187, vol. 99, No. 15.
Tamimi, Rulla M., "Endogenous sex hormone levels and mammographic density among postmenopausal women," Cancer Epidemiol. Biomarkers Prev., Nov. 2005, pp. 2641-2647, vol. 14, No. 11 Pt. 1.
Templin, Markus F., et al., "Protein microarrays: promising tools for proteomic research," Proteomics, Nov. 2003, pp. 2155-2166, vol. 3, No. 11.
Torres, Vicente A., et al., "Rab5 mediates caspase-8-promoted cell motility and metastasis," Mol. Biol. Cell, Jan. 2010, pp. 369-376, vol. 21, No. 2.
Tozlu, Sengül, et al., "Identification of novel genes that co-cluster with estrogen receptor alpha in breast tumor biopsy specimens, using a large-scale real-time reverse transcription-PCR approach," Endocr. Relat. Cancer, Dec. 2006, pp. 1109-1120, vol. 13, No. 4.
Wandall, Hans H., et al., "Cancer biomarkers defined by autoantibody signatures to aberrant Oglycopeptide epitopes," Cancer Res., Feb. 2010, pp. 1306-1313, vol. 70, No. 4.
Wang, Cheng-Chi, et al., "Glycan microarray of Globo H and related structures for quantitative analysis of breast cancer," Proc. Natl. Acad. Sci., Aug. 2008, pp. 11661-11666, vol. 105, No. 33.
Wang, Xiaoju, et al., "Autoantibody signatures in prostate cancer," N. Engl. J. Med., Sep. 2005, pp. 1224-1235, vol. 353, No. 12.
Witt, Abigail E., et al., "Functional proteomics approach to investigate the biological activities of cDNAs implicated in breast cancer," J. Proteome Res., Mar. 2006, pp. 599-610, vol. 5, No. 3.
Wong, Jessica, et al., "Rapid detection of antibodies in sera using multiplexed self-assembling bead arrays," J. Immunol. Methods, Oct. 2009, pp. 171-182, vol. 350, Nos. 1-2.
Wulfkuhle, Julia D., et al., "New approaches to proteomic analysis of breast cancer," Proteomics, Oct. 2001, pp. 1205-1215, vol. 1, No. 10.
Zhao, Hongjuan, "Different gene expression patterns in invasive lobular and ductal carcinomas of the breast," Mol. Biol. Cell, Jun. 2004, pp. 2523-2536, vol. 15, No. 6.
Zhou, Jin, et al., "A novel gene, NMES1, downregulated in human esophageal squamous cell carcinoma," Int. J. Cancer, 2002,101 (4), 311-6.
Zhu, Henh, et al., "Global analysis of protein activities using proteome chips," Science, Sep. 2001, pp. 2101-2105, vol. 293, No. 5537.
International Search Report and Written Opinion for PCT/US2011/047741 dated Mar. 23, 2012 (19 pages).
International Preliminary Report on Patentability for PCT/US2011/047741 dated Feb. 19, 2013 (11 pages).
Madrid, et al. "Autoantibodies in breast cancer identify proteins involved in self-renewal and epigenetic chromatin remodeling" The Open Biomarkers Journal, 3: 13-20 (2010).
Tan, et al., "Serum autoantibodies as biomarkers for early cancer detection," FEBS Journal, 276: 6880-6900 (2009).
Davis, et al., Amplification Patterns of three genomic regions predict distant recurrence in breast carcinoma, Journal of Molecular Diagnostics, 9(3): 327-336. Jul. 2007.
Pan, et al., "Involvement of the Conserved adaptor protein alix in actin cytoskeleton assembly," Journal of Biological Chemistry, 281(45): 34640-34650, Nov. 2006.
Zhao, et al., "Different gene expression patterns in invasive lobular and ductal carcinomas of the breast," Molecular Biology of the Cell, 15(6): 2523-2536, Jan. 2004.
Thatcher, et al., "Regulation of zebrafish fin regeneration by microRNAs," Proceedings of the National Academy of Sciences, 105(47): 18384-18389, Nov. 2008.
Yamashita, et al., "Suppression of invasive characteristics by antisense introduction of overexpressed HOX genes in ovarian cancer cells," International Journal of Oncology, 28: 931, Apr. 2006.
Yoo, et al., "Transcriptional factor Late SV40 Factor (LSF) functions as an oncogene in hepatocellular carcinoma," PNAS, 107(18): 8357-8362, Apr. 2010.
European Search Report for EP3054299, dated Oct. 16, 2016.

\* cited by examiner

BIOMARKERS FOR THE EARLY DETECTION OF BREAST CANCER

CROSS-REFERENCE

This application claims priority to U.S. Provisional Patent Application Ser. No. 61/373,359 filed Aug. 13, 2010, incorporated by reference herein in its entirety.

STATEMENT OF U.S. GOVERNMENT INTEREST

This invention was made with government support under U01 CA117374 and P50 CA089393 awarded by the National Institutes of Health. The U.S. government has certain rights in the invention.

SEQUENCE LISTING STATEMENT

The sequence listing is filed in this application in electronic format only and is incorporated by reference herein. The sequence listing text file "10-294-PCT_SeqList.txt" was created on Aug. 1, 2011, and is 54,649 byte in size.

BACKGROUND

Despite recent advances in early detection and treatment, breast cancer remains a common and significant health problem in the United States. Women diagnosed with stage II and III breast cancer have a high-risk for distant recurrence and up to half of these women will develop metastatic disease, which remains incurable with current therapy. In this setting, there is intense effort in the search for biomarkers that can detect early disease, and to monitor for disease progression and recurrence. With the advent of molecularly-targeted therapeutics, biomarkers that are associated with biological subtypes of cancer may be useful for predicting responses to therapeutic interventions.

Proteomics-based approaches to distinguish cancer-bearing patient sera from healthy control sera have been challenged by the difficulty in identifying small quantities of protein fragments within complex protein mixtures, protein instability, and natural variations in protein content within patient populations. Autoantibodies (AAb) to tumor antigens have advantages over other serum proteins as potential cancer biomarkers as they are stable, highly specific, easily purified from serum, and are readily detected with well-validated secondary reagents. Although they have high specificities to distinguish cancer from control sera, most tumor AAb demonstrate poor sensitivities. Testing multiple antigens in parallel may serve to increase the predictive value of tumor-specific antibodies for use as immunodiagnostics.

Protein microarrays offer an emerging platform to present tumor antigens to screen for immune responses. In comparison to traditional ELISAs, protein microarrays are capable of presenting and assessing hundreds of tumor antigens simultaneously. The responses are rapidly identified because the address of each protein is known in advance and there are no representation issues; all proteins, even rare ones, are represented equally (usually in duplicate). The proteins are arrayed on a single microscope slide requiring only a few microliters of serum per assay. Known tumor antigens as well as predicted tumor antigens can be included to generate a comprehensive protein tumor antigen array. Despite some early demonstrations of feasibility, protein microarrays are not yet widely used, due to the labor and technical issues associated with production, purification, and quality control of proteins for spotting on the array, as well as difficulties with downstream validation assays of target AAb.

SUMMARY OF THE INVENTION

In a first aspect, the present invention provides polypeptide probe sets comprising:
at least 2 different isolated polypeptides selected from the group consisting of ATP6AP1 (SEQ ID NO: 13), PDCD6IP (SEQ ID NO: 21), DBT (SEQ ID NO: 25), CSNK1E (SEQ ID NO: 9), FRS3 (SEQ ID NO: 3), RAC3 (SEQ ID NO: 15), HOXD1 (SEQ ID NO: 7), SF3A1 (SEQ ID NO: 1), CTBP1 (SEQ ID NO: 29), C15orf48 (SEQ ID NO: 35), MYOZ2 (SEQ ID NO: 33), EIF3E (SEQ ID NO: 39), BAT4 (SEQ ID NO: 5), ATF3 (SEQ ID NO: 19), BMX (SEQ ID NO: 45), RAB5A (SEQ ID NO: 23), UBAP1 (SEQ ID NO: 47), SOX2 (SEQ ID NO: 31), GPR157 (SEQ ID NO: 43), BDNF (SEQ ID NO: 17), ZMYM6 (SEQ ID NO: 41), SLC33A1 (SEQ ID NO: 11), TRIM32 (SEQ ID NO: 37), ALG10 (SEQ ID NO: 27), TFCP2 (SEQ ID NO: 49), SERPINH1 (SEQ ID NO: 51), SELL (SEQ ID NO: 55), ZNF510 (SEQ ID NO: 53), or antigenic fragments thereof, attached to the support.

In a second aspect, the present invention provides polynucleotide arrays comprising:
(a) a support; and
(b) at least 2 different isolated nucleic acids encoding polypeptides selected from the group consisting of ATP6AP1 (SEQ ID NO: 14), PDCD6IP (SEQ ID NO: 22), DBT (SEQ ID NO: 26), CSNK1E (SEQ ID NO: 10), FRS3 (SEQ ID NO: 4), RAC3 (SEQ ID NO: 16), HOXD1 (SEQ ID NO: 8), SF3A1 (SEQ ID NO: 2), CTBP1 (SEQ ID NO: 30), C15orf48 (SEQ ID NO: 36), MYOZ2 (SEQ ID NO: 34), EIF3E (SEQ ID NO: 40), BAT4 (SEQ ID NO: 6), ATF3 (SEQ ID NO: 20), BMX (SEQ ID NO: 46), RAB5A (SEQ ID NO: 24), UBAP1 (SEQ ID NO: 48), SOX2 (SEQ ID NO: 32), GPR157 (SEQ ID NO: 44), BDNF (SEQ ID NO: 18), ZMYM6 (SEQ ID NO: 42), SLC33A1 (SEQ ID NO: 12), TRIM32 (SEQ ID NO: 38), ALG10 (SEQ ID NO: 28), TFCP2 (SEQ ID NO: 50), SERPINH1 (SEQ ID NO: 52), SELL (SEQ ID NO: 56), ZNF510 (SEQ ID NO: 54), or antigenic fragments thereof, attached to the support.

In a third aspect, the present invention provides methods for detecting breast cancer, comprising;
(a) contacting a suitable bodily fluid sample obtained from a subject at risk of breast cancer with one or more isolated polypeptides selected from the group consisting of ATP6AP1 (SEQ ID NO: 13), PDCD6IP (SEQ ID NO: 21), DBT (SEQ ID NO: 25), CSNK1E (SEQ ID NO: 9), FRS3 (SEQ ID NO: 3), RAC3 (SEQ ID NO: 15), HOXD1 (SEQ ID NO: 7), SF3A1 (SEQ ID NO: 1), CTBP1 (SEQ ID NO: 29), C15orf48 (SEQ ID NO: 35), MYOZ2 (SEQ ID NO: 33), EIF3E (SEQ ID NO: 39), BAT4 (SEQ ID NO: 5), ATF3 (SEQ ID NO: 19), BMX (SEQ ID NO: 45), RAB5A (SEQ ID NO: 23), UBAP1 (SEQ ID NO: 47), SOX2 (SEQ ID NO: 31), GPR157 (SEQ ID NO: 43), BDNF (SEQ ID NO: 17), ZMYM6 (SEQ ID NO: 41), SLC33A1 (SEQ ID NO: 11), TRIM32 (SEQ ID NO: 37), ALG10 (SEQ ID NO: 27), TFCP2 (SEQ ID NO: 49), SERPINH1 (SEQ ID NO: 51), SELL (SEQ ID NO: 55), ZNF510 (SEQ ID NO: 53), or antigenic fragments thereof; wherein the contacting occurs under conditions suitable for selective binding of antibodies in the bodily fluid sample to the one or more polypeptides; and (b) detecting presence of antibodies to the polypeptides in the bodily fluid sample;

wherein the presence of antibodies to the one or more polypeptides indicates a likelihood of breast cancer in the subject.

DETAILED DESCRIPTION OF THE INVENTION

In a first aspect, the present invention provides polypeptide probe sets comprising:

(a) at least 2 different isolated polypeptides selected from the group consisting of ATP6AP1 (SEQ ID NO: 13), PDCD6IP (SEQ ID NO: 21), DBT (SEQ ID NO: 25), CSNK1E (SEQ ID NO: 9), FRS3 (SEQ ID NO: 3), RAC3 (SEQ ID NO: 15), HOXD1 (SEQ ID NO: 7), SF3A1 (SEQ ID NO: 1), CTBP1 (SEQ ID NO: 29), C15orf48 (SEQ ID NO: 35), MYOZ2 (SEQ ID NO: 33), EIF3E (SEQ ID NO: 39), BAT4 (SEQ ID NO: 5), ATF3 (SEQ ID NO: 19), BMX (SEQ ID NO: 45), RAB5A (SEQ ID NO: 23), UBAP1 (SEQ ID NO: 47), SOX2 (SEQ ID NO: 31), GPR157 (SEQ ID NO: 43), BDNF (SEQ ID NO: 17), ZMYM6 (SEQ ID NO: 41), SLC33A1 (SEQ ID NO: 11), TRIM32 (SEQ ID NO: 37), ALG10 (SEQ ID NO: 27), TFCP2 (SEQ ID NO: 49), SERPINH1 (SEQ ID NO: 51), SELL (SEQ ID NO: 55), ZNF510 (SEQ ID NO: 53), or antigenic fragments thereof, attached to the support.

Using a sequential screening strategy to select antigen-specific antibodies (AAb) from 4988 tumor antigens, 119 AAb potential novel biomarkers for the early detection of breast cancer were identified. A blinded validation study produced supporting evidence for 28 of these potential biomarkers, recited above. Thus, the polypeptide probe sets of the invention can be used, for example, to detect tumor antigen-specific autoantibodies in a bodily fluid sample from patients with breast cancer, such as early stage breast cancer. Descriptions of the polypeptides, their amino acid sequences and their nucleic acid sequences are provided in Table 1.

In various embodiments, the polypeptide probe sets comprise at least 2, 3, 4, 5, 6, 7, 8, 9, 10, 11, 12, 13, 14, 15, 16, 17, 18, 19, 20, 21, 22, 23, 24, 25, 26, 27, or all 28 of the recited polypeptides, or antigenic portions thereof.

In a preferred embodiment, the at least 2 different isolated polypeptides in the probe sets are selected from the group consisting of ATP6AP1 (SEQ ID NO: 13), PDCD6IP (SEQ ID NO: 21), DBT (SEQ ID NO: 25), CSNK1E (SEQ ID NO: 9), FRS3 (SEQ ID NO: 3), HOXD1 (SEQ ID NO: 7), SF3A1 (SEQ ID NO: 1), C15orf48 (SEQ ID NO: 35), MYOZ2 (SEQ ID NO: 33), BAT4 (SEQ ID NO: 5), BMX (SEQ ID NO: 45), RAB5A (SEQ ID NO: 23), UBAP1 (SEQ ID NO: 47), GPR157 (SEQ ID NO: 43), ZMYM6 (SEQ ID NO: 41), SLC33A1 (SEQ ID NO: 11), TRIM32 (SEQ ID NO: 37), ALG10 (SEQ ID NO: 27), TFCP2 (SEQ ID NO: 49), SERPINH1 (SEQ ID NO: 51), SELL (SEQ ID NO: 55), ZNF510 (SEQ ID NO: 53), or antigenic fragments thereof. Thus, in various embodiments, the polypeptide probe sets comprise at least 2, 3, 4, 5, 6, 7, 8, 9, 10, 11, 12, 13, 14, 15, 16, 17, 18, 19, 20, 21, or all 22 of the recited polypeptides, or antigenic portions thereof. In a further preferred embodiment the probe sets comprise ATP6AP1 (SEQ ID NO: 13) and at least one other of the recited polypeptides, or antigenic portions thereof. Thus, in various embodiments, the polypeptide arrays comprise at least ATP6AP1 and 1, 2, 3, 4, 5, 6, 7, 8, 9, 10. 11, 12, 13, 14, 15, 16, 17, 18, 19, 20, 21, 22, 23, 24, 25, 26, or all 27 of the other recited polypeptides, or antigenic portions thereof.

In a preferred embodiment, the probe sets comprise at least 2, 3, 4, 5, or all 6 of ATP6AP1 (SEQ ID NO: 13), CTBP1 (SEQ ID NO: 29), EIF3E (SEQ ID NO: 39), ATF3 (SEQ ID NO: 19), SOX2 (SEQ ID NO: 31), and BDNF (SEQ ID NO: 17), or antigenic portions thereof. The term "polypeptide" is used in its broadest sense to refer to a polymer of subunit amino acids, amino acid analogs, or peptidomimetics, including proteins and peptoids. The polypeptides may be naturally occurring full length proteins or fragments thereof, processed forms of naturally occurring polypeptides (such as by enzymatic digestion), chemically synthesized polypeptides, or recombinantly expressed polypeptides. The polypeptides may comprise D- and/or L-amino acids, as well as any other synthetic amino acid subunit, and may contain any other type of suitable modification, including but not limited to peptidomimetic bonds and reduced peptide bonds.

As used herein, an "antigenic fragment" is any portion of at least 4 amino acids of the recited polypeptide that can give rise to an immune response. In various preferred embodiments, the antigenic fragments are at least 5, 6, 7, 8, 9, 10, 11, 12, 13, 14, 151, 16, 17, 18, 19, 20, 21, 22, 23, 24, 25, 26, 27, 28, 29, 30, 35, 40, 45, 50, 75, 100, 150, 200, 250, 300, or the full amino acid sequence of the recited polypeptide.

In various further preferred embodiments, that can be combined with any other embodiments, the polypeptide probe sets comprise no more than 20,000 different polypeptides, or antigenic portions thereof and preferably comprise no more than 10,000; 5,000; 1,000; 500; 250; 100; 75; 50; 45; 40; 35; 30; 28, 27, 26, 25, 24, 23, 22, 21, 20, 19, 18, 17, 16, 15, 14, 13, 12, 11, 10, 9, 8, 7, 6, 5, 4, 3, or 2 different polypeptides. In this and other embodiments, two or more antigenic portions of the same polypeptide in the probe set count only as 1 polypeptide or antigenic portion thereof.

As will be appreciated by those of skill in the art, it may be desirable to include further polypeptides or other molecules in the probe sets as references, controls, positional markers, or as additional markers. Any suitable such further polypeptide or other molecule can be used. Exemplary additional polypeptide markers include but are not limited to p53, CTBP1, RAC3, and activating transcription factor-3 (ATF3). Exemplary analytical controls include human IgG and empty spots (when the probe set is present on a support). Any portion or the entirety of the recited polypeptides may be used in the probe set, so long as it is capable of binding to autoantibodies against the polypeptide.

The polypeptide probe sets can be present in any form useful for a given purpose. In various preferred embodiments, they can be present in solution, lyophilized, frozen, or immobilized on a substrate.

In one preferred embodiment, the polypeptides are immobilized on a substrate. Any suitable technique for immobilizing the polypeptides on the support can be used. In one embodiment, Nucleic Acid Protein Programmable Array (NAPPA technology can be used. NAPPA arrays are generated by printing full-length cDNAs encoding the target proteins at each feature of the array. The proteins are then transcribed and translated by a cell-free system and immobilized in situ using epitope tags fused to the proteins. Other suitable immobilization methods include, but are not limited to luciferase immunoprecipitation systems (LIPS), Luminex™ beads, wells of a 96 well dish, standard immune dipstick assays, standard ELISA assays.

As used herein, an array may be any arrangement or disposition of the polypeptides. In one embodiment, the polypeptides are at specific and identifiable locations on the array. Those of skill in the art will recognize that many such permutations of the polypeptides on the array are possible. In another non-limiting embodiment, each distinct location on the array comprises a distinct polypeptide.

Any suitable support may be used. Examples of such supports include, but are not limited to, microarrays, beads, columns, optical fibers, wipes, nitrocellulose, nylon, glass, quartz, diazotized membranes (paper or nylon), silicones, polyformaldehyde, cellulose, cellulose acetate, paper, ceramics, metals, metalloids, semiconductive materials, coated beads, magnetic particles; plastics such as polyethylene, polypropylene, and polystyrene; and gel-forming materials, such as proteins (e.g., gelatins), lipopolysaccharides, silicates, agarose, polyacrylamides, methylmethacrylate polymers; sol gels; porous polymer hydrogels; nanostructured surfaces; nanotubes (such as carbon nanotubes), and nanoparticles (such as gold nanoparticles or quantum dots).

In one embodiment, the support is a solid support. Any suitable "solid support" may be used to which the polypeptides can be attached including but not limited to dextrans, hydrogels, silicon, quartz, other piezoelectric materials such as langasite ($La_3Ga_5SiO_{14}$), nitrocellulose, nylon, glass, diazotized membranes (paper or nylon), polyformaldehyde, cellulose, cellulose acetate, paper, ceramics, metals, metalloids, semiconductive materials, coated beads, magnetic particles; plastics such as polyethylene, polypropylene, and polystyrene; and gel-forming materials, such as proteins (e.g., gelatins), lipopolysaccharides, silicates, agarose and polyacrylamides.

Any suitably sized solid support can be used. In one non-limiting example, the solid support comprises slides with dimensions of approximately 3 inches by 1 inch.

In all embodiments of the invention, the polypeptides of the probe set may further comprise a tag, such as a detectable moiety. This is particularly preferred when the polypeptide probe sets or in solution, or in any other format where different polypeptides in the probe set cannot be distinguished by differential positions on a support. In such embodiments, it is particularly preferred that the different polypeptides, or antigenic fragments thereof, that are present in the probe set are distinguishable, through the use of differentially detectable tags, using techniques known to those of skill in the art. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. The polypeptides of the probe set, comprising a detectable tag can be used diagnostically to, for example, assess the presence of antibodies to the polypeptides in a sample; and thereby detect the presence of breast cancer, or monitor the development or progression of breast cancer as part of a clinical testing procedure. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis/diagnosis techniques and/or methods used such as immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples preferred tags are enzymes that catalyze production and local deposition of a detectable product. Enzymes typically conjugated to polypeptides to permit their immunohistochemical visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. The polypeptides can be labeled using colloidal gold or they can be labeled with radioisotopes, such as $^{33}P$, $^{32}P$, $^{35}S$, $^{3}H$, and $^{125}I$. Polypeptides of the probe set can be attached to radionuclides directly or indirectly via a chelating agent by methods well known in the art.

In a second aspect, the present invention provides polynucleotide arrays comprising:

(a) a support; and (b) at least 2 different isolated nucleic acids encoding polypeptides selected from the group consisting of ATP6AP1 (SEQ ID NO: 14), PDCD6IP (SEQ ID NO: 22), DBT (SEQ ID NO: 26), CSNK1E (SEQ ID NO: 10), FRS3 (SEQ ID NO: 4), RAC3 (SEQ ID NO: 16), HOXD1 (SEQ ID NO: 8), SF3A1 (SEQ ID NO: 2), CTBP1 (SEQ ID NO: 30), C15orf48 (SEQ ID NO: 36), MYOZ2 (SEQ ID NO: 34), EIF3E (SEQ ID NO: 40), BAT4 (SEQ ID NO: 6), ATF3 (SEQ ID NO: 20), BMX (SEQ ID NO: 46), RAB5A (SEQ ID NO: 24), UBAP1 (SEQ ID NO: 48), SOX2 (SEQ ID NO: 32), GPR157 (SEQ ID NO: 44), BDNF (SEQ ID NO: 18), ZMYM6 (SEQ ID NO: 42), SLC33A1 (SEQ ID NO: 12), TRIM32 (SEQ ID NO: 38), ALG10 (SEQ ID NO: 28), TFCP2 (SEQ ID NO: 50), SERPINH1 (SEQ ID NO: 52), SELL (SEQ ID NO: 56), ZNF510 (SEQ ID NO: 54), or antigenic fragments thereof, attached to the support In this aspect, the arrays can also be used for example, to detect tumor antigen-specific autoantibodies in patients with breast cancer, such as early stage breast cancer. Any suitable technique can be used for attaching the nucleic acids to the support. In one embodiment, NAPPA arrays are generated by printing fcDNAs encoding the target proteins, or antigenic fragments thereof, at features of the support. Other techniques for printing nucleic acids on a support can be used and are well known in the art.

In various embodiments, the arrays comprise at least 2, 3, 4, 5, 6, 7, 8, 9, 10, 11, 12, 13, 14, 15, 16, 17, 18, 19, 20, 21, 22, 23, 24, 25, 26, 27, or all 28 of the recited nucleic acids, attached to the support.

In a preferred embodiment the at least 2 different isolated nucleic acids encode polypeptides selected from the group consisting of ATP6AP1 (SEQ ID NO: 14), PDCD6IP (SEQ ID NO: 22), DBT (SEQ ID NO: 26), CSNK1E (SEQ ID NO: 10), FRS3 (SEQ ID NO: 4), HOXD1 (SEQ ID NO: 8), SF3A1 (SEQ ID NO: 2), C15orf48 (SEQ ID NO: 36), MYOZ2 (SEQ ID NO: 34), BAT4 (SEQ ID NO: 6), BMX (SEQ ID NO: 46), RAB5A (SEQ ID NO: 24), UBAP1 (SEQ ID NO: 48), GPR157 (SEQ ID NO: 44), ZMYM6 (SEQ ID NO: 42), SLC33A1 (SEQ ID NO: 12), TRIM32 (SEQ ID NO: 38), ALG10 (SEQ ID NO: 28), TFCP2 (SEQ ID NO: 50), SERPINH1 (SEQ ID NO: 52), SELL (SEQ ID NO: 56), ZNF510 (SEQ ID NO: 54), or antigenic fragments thereof. Thus, in various embodiments, the polynucleotide arrays comprise at least 2, 3, 4, 5, 6, 7, 8, 9, 10, 11, 12, 13, 14, 15, 16, 17, 18, 19, 20, 21, or all 22 of the recited nucleic acids, or antigenic portions thereof, attached to the support.

In a further preferred embodiment the at least 2 different isolated nucleic acids encode ATP6AP1 (SEQ ID NO: 14) and at least one other of the recited nucleic acids, or antigenic portions thereof. Thus, in various embodiments, the polynucleotide arrays comprise at least ATP6AP1 and 1, 2, 3, 4, 5, 6, 7, 8, 9, 10, 11, 12, 13, 14, 15, 16, 17, 18, 19, 20, 21, 22, 23, 24, 25, 26, or all 27 of the other recited nucleic acids, or antigenic portions thereof, attached to the support.

In another preferred embodiment, the at least isolated nucleic acids encode 2, 3, 4, 5, or all 6 of ATP6AP1 (SEQ ID NO: 13), CTBP1 (SEQ ID NO: 29), EIF3E (SEQ ID NO: 39), ATF3 (SEQ ID NO: 19), SOX2 (SEQ ID NO: 31), and BDNF (SEQ ID NO: 17), or antigenic portions thereof.

In various further preferred embodiments, that can be combined with any other embodiments, the arrays comprise no more than 20,000 different nucleic acids, and preferably comprise no more than 10,000; 5,000; 1,000; 500; 250; 100; 75; 50; 45; 40; 35; 30; 28, 27, 26, 25, 24, 23, 22, 21, 20, 19, 18, 17, 16, 15, 14, 13, 12, 11, 10, 9, 8, 7, 6, 5, 4, 3, or 2 different nucleic acids.

As will be appreciated by those of skill in the art, it may be desirable to place nucleic acids encoding other polypeptides on the support as controls, positional markers, or as additional markers, including but not limited to p53, CTBP1, RAC3, and activating transcription factor-3 (ATF3).

Any portion or the entirety of the recited nucleic acid may be attached to the support, so long as it is encodes a polypeptide, or antigenic fragment thereof, capable of binding to autoantibodies against the polypeptide.

The definitions and all embodiments disclosed in the first aspect apply to this second aspect.

In a third aspect, the present invention provides methods for detecting breast cancer, comprising;

(a) contacting a suitable bodily fluid sample obtained from a subject at risk of breast cancer with one or more isolated polypeptides selected from the group consisting of ATP6AP1 (SEQ ID NO: 13), PDCD6IP (SEQ ID NO: 21), DBT (SEQ ID NO: 25), CSNK1E (SEQ ID NO: 9), FRS3 (SEQ ID NO: 3), RAC3 (SEQ ID NO: 15), HOXD1 (SEQ ID NO: 7), SF3A1 (SEQ ID NO: 1), CTBP1 (SEQ ID NO: 29), C15orf48 (SEQ ID NO: 35), MYOZ2 (SEQ ID NO: 33), EIF3E (SEQ ID NO: 39), BAT4 (SEQ ID NO: 5), ATF3 (SEQ ID NO: 19), BMX (SEQ ID NO: 45), RAB5A (SEQ ID NO: 23), UBAP1 (SEQ ID NO: 47), SOX2 (SEQ ID NO: 31), GPR157 (SEQ ID NO: 43), BDNF (SEQ ID NO: 17), ZMYM6 (SEQ ID NO: 41), SLC33A1 (SEQ ID NO: 11), TRIM32 (SEQ ID NO: 37), ALG10 (SEQ ID NO: 27), TFCP2 (SEQ ID NO: 49), SERPINH1 (SEQ ID NO: 51), SELL (SEQ ID NO: 55), ZNF510 (SEQ ID NO: 53), or antigenic fragments thereof; wherein the contacting occurs under conditions suitable for selective binding of antibodies in the bodily fluid sample to the one or more polypeptides; and (b) detecting presence of antibodies to the polypeptides in the bodily fluid sample;

wherein the presence of antibodies in the bodily fluid sample to the one or more polypeptides indicates a likelihood of breast cancer in the subject.

The inventors have discovered that the presence of autoantibodies to one or more of the recited polypeptides is a positive predictor of breast cancer, and thus the methods of the invention provide valuable diagnostic and prognostic information to an attending physician.

As used herein a subject "at risk of breast cancer" is any human considered to be in a risk group for breast cancer. In one embodiment, the subject is a woman. In other embodiments, the subject has one or more of a lump in their breast tissue, lymph nodes, or armpit; changes in breast size or shape; skin dimpling; nipple inversion; spontaneous single-nipple discharge; a family/personal history of breast cancer; or is a carrier of a mutation in the BRCA or other gene that predisposes one to breast cancer.

Suitable bodily fluid samples include serum, plasma, CSF, pleural fluid, joint fluid, nipple discharge, saliva. In a preferred embodiment, the bodily fluid sample is serum or plasma.

In one embodiment, the presence of any amount of antibodies to the polypeptides in a sample from a subject at risk of breast cancer can indicate a likelihood of breast cancer in the subject. In another embodiment, if antibodies to the polypeptides are present in a sample from a subject at risk of breast cancer, at levels which are higher than that of a control sample (i.e. a sample from a subject who does not have breast cancer) than the subject at risk of breast cancer has a likelihood of breast cancer. Subjects with a likelihood of breast cancer can then be tested for the actual presence of breast cancer using standard diagnostic techniques known to the skilled artisan, including mammography, biopsy, or breast MRI. In various embodiments, the method results in an accurate diagnosis in at least 70% of cases; more preferably of at least 75%, 80%, 85%, 90%, or more of the cases. In a preferred embodiment, the likelihood of breast cancer is a likelihood of Stage I or Stage II breast cancer.

In various embodiments, the methods comprise contacting a bodily fluid sample, such as serum, obtained from a subject at risk of breast cancer with 2, 3, 4, 5, 6, 7, 8, 9, 10, 11, 12, 13, 14, 15, 16, 17, 18, 19, 20, 21, 22, 23, 24, 25, 26, 27, or all 28 of the recited polypeptides, or antigenic fragments thereof. In various embodiments, the presence of antibodies in the bodily fluid sample to 1, 2, 3, 4, 5, 6, 7, 8, 9, 10, 11, 12, 13, 14, 15, 16, 17, 18, 19, 20, 21, 22, 23, 24, 25, 26, 27, or all 28 of the recited polypeptides, or antigenic fragments thereof, indicates a likelihood of breast cancer in the subject.

In a preferred embodiment, the one or more isolated polypeptides are selected from the group consisting of ATP6AP1 (SEQ ID NO: 13), PDCD6IP (SEQ ID NO: 21), DBT (SEQ ID NO: 25), CSNK1E (SEQ ID NO: 9), FRS3 (SEQ ID NO: 3), HOXD1 (SEQ ID NO: 7), SF3A1 (SEQ ID NO: 1), C15orf48 (SEQ ID NO: 35), MYOZ2 (SEQ ID NO: 33), BAT4 (SEQ ID NO: 5), BMX (SEQ ID NO: 45), RAB5A (SEQ ID NO: 23), UBAP1 (SEQ ID NO: 47), GPR157 (SEQ ID NO: 43), ZMYM6 (SEQ ID NO: 41), SLC33A1 (SEQ ID NO: 11), TRIM32 (SEQ ID NO: 37), ALG10 (SEQ ID NO: 27), TFCP2 (SEQ ID NO: 49), SERPINH1 (SEQ ID NO: 51), SELL (SEQ ID NO: 55), ZNF510 (SEQ ID NO: 53), or antigenic fragments thereof. Thus, in various embodiments, the methods comprise contacting a serum sample obtained from a subject at risk of breast cancer with 2, 3, 4, 5, 6, 7, 8, 9, 10, 11, 12, 13, 14, 15, 16, 17, 18, 19, 20, 21, or all 22 of the recited polypeptides, or antigenic fragments thereof.

In a further preferred embodiment, the methods comprise contacting a bodily fluid sample, such as a serum sample, obtained from a subject at risk of breast cancer with ATP6AP1 (SEQ ID NO: 13), or an antigenic fragment thereof. In this embodiment, the method may further comprise contacting the serum sample with 1, 2, 3, 4, 5, 6, 7, 8, 9, 10, 11, 12, 13, 14, 15, 16, 17, 18, 19, 20, 21, 22, 23, 24, 25, 26, or all 27 of the other recited polypeptides, or antigenic portions thereof.

In a preferred embodiment, the methods comprise contacting a bodily fluid sample, such as a serum sample, obtained from a subject at risk of breast cancer with 2, 3, 4, 5, or all 6 of ATP6AP1 (SEQ ID NO: 13), CTBP1 (SEQ ID NO: 29), EIF3E (SEQ ID NO: 39), ATF3 (SEQ ID NO: 19), SOX2 (SEQ ID NO: 31), and BDNF (SEQ ID NO: 17), or antigenic portions thereof.

In one preferred embodiment, the method comprises contacting the bodily fluid sample, such as a serum sample, to a polypeptide array of any embodiment of the first aspect of the invention, or to an array according to any embodiment of the second aspect of the invention after the encoded proteins are then transcribed and translated by a cell-free system and immobilized in situ using epitope tags fused to the proteins.

As will be appreciated by those of skill in the art, it may be desirable to test for autoantibodies to other polypeptides, and so the method may comprise testing for such further autoantibodies, such as antibodies to p53, CTBP1, RAC3, and activating transcription factor-3 (ATF3).

The "binding" may comprise any detectable interaction of an antibody with an antigen (polypeptide or polynucleotide molecule), including without limitation a covalent bond, ionic bond, salt bridge, hydrogen bond, van der Waals interaction, hydrophobic/hydrophilic interaction, electrostatic interaction, steric interaction, other associations, or any combination of any of the foregoing. As will be understood by those of skill in the art, array interactions do not require chemical binding.

In one embodiment, a probe set, such as an array according to any embodiment of the invention are contacted with the bodily fluid, such as a serum sample, under conditions suitable for binding of antibodies in the fluid to antigens in the probe set; unbound antibodies are washed and bound antibodies are detected by labeled secondary reagents, such as labeled secondary antibodies. Suitable conditions and reagents to promote binding of specific antibody types to antigens (polypeptides or polynucleotides molecules) is well within the level of those of skill in the art. Thus, the methods of the invention are not limited by any specific type of binding conditions employed. Such conditions will vary depending on the type of sample, desired stringency of the binding interaction, and nature of the competing materials in the binding solution, the type of molecules (polypeptide or polynucleotide) in the probe set, the type of probe set, and, for embodiments in which the probe set is present on a support, the type of support, and the density of the molecules arrayed on the support. In a preferred embodiment, the conditions comprise a step to remove unbound antibodies. Determining the need for such a step, and appropriate conditions for such a step, are well within the level of skill in the art.

Any type of labeled secondary reagents label can be used in the methods of the present invention, including but not limited to radioisotope labels, fluorescent labels, luminescent labels, and electrochemical labels (ie: antibody labels with different electrode mid-point potential, where detection comprises detecting electric potential of the label). In a preferred embodiment, fluorescent or electrochemical labels are used. Detection of signal from detectable labels is well within the level of skill in the art. For example, fluorescent array readers are well known in the art, as are instruments to record electric potentials on a substrate (For electrochemical detection see, for example, J. Wang (2000) *Analytical Electrochemistry*, Vol., 2nd ed., Wiley-VCH, New York). In a further embodiment, the detectable labels comprise quantum dots. In one embodiment, secondary labels can be used, including but not limited to secondary antibodies or ligands that bind to the antibodies. In embodiments where multiple polypeptides are used as probes, it is preferable that they are differentially distinguishable, as discussed above. In a further embodiment, antibodies bound to each polypeptide are quantified by staining with anti-fusion tag antibodies and measurement of the fluorescence intensity signal generated from secondary antibodies. Detecting presence of antibodies to the polypeptides in the bodily fluid sample can be accomplished by standard methods in the art. Suitable conditions and reagents will be understood by those of skill in the art based on the teachings herein. The presence of antibodies to the polypeptides may be determined by immunoassay methods utilizing the antibodies described above. Such immunoassay methods include, but are not limited to, direct or indirect immunoassay such as for example a competitive binding assay, a non-competitive binding assay, a radioimmunoassay, immunohistochemistry, an enzyme-linked immunosorbent assay (ELISA), a sandwich assay, a gel diffusion immunodiffusion assay, an agglutination assay, dot blotting, a fluorescent immunoassay such as fluorescence-activated cell sorting (FACS), chemiluminescence immunoassay, immunoPCR immunoassay, a protein A or protein G immunoassay, and an immunoelectrophoresis assay such as western blotting and others commonly used and widely described in scientific and patent literature, and many employed commercially.

In the case of an enzyme immunoassay, an enzyme is conjugated to the second antibody, usually by means of glutaraldehyde or periodate. As will be readily recognized, however, a wide variety of different ligation techniques exist which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product, rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of secreted protein or fragment thereof. Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed.

In a further embodiment, the presence of antibodies to the polypeptides may be determined by using Western blot analysis. The technique generally comprises separating sample antibody proteins by gel electrophoresis on the basis of molecular weight and transferring the antibody proteins to a suitable solid support, such as nitrocellulose filter, a nylon filter, or derivatized nylon filter. The sample is incubated with the polypeptides or antigenic fragments thereof that specifically bind the sample antibodies and the resulting complex is detected. The polypeptides may be directly labeled or alternatively may be subsequently detected using labeled secondary antibodies that specifically bind to the polypeptide-antibody complex. Antibody binding reagents may be, for example, protein A, or other antibodies. Antibody binding reagents may be radiolabeled or enzyme linked. Detection may be by autoradiography, calorimetric reaction or chemiluminescence. This method allows both quantitation of an amount of sample antibody and determination of its identity by a relative position on the membrane which is indicative of a migration distance in the acrylamide gel during electrophoresis. The definitions and all embodiments disclosed in the first and second aspects apply to this third aspect.

Examples

Custom NAPPA protein microarrays were used to detect tumor antigen-specific AAb in the sera of patients with early-stage breast cancer. Using a sequential screening strategy to select AAb from 4988 tumor antigens, we identified 119 AAb potential biomarkers for the early detection of breast cancer. A blinded validation study produced supporting evidence for 28 of these potential biomarkers.

Sera used in these analyses were obtained from Fox Chase Cancer Center (FCCC) and the Duke University Medical Center (DUMC) with support from the NCI Early Detection Research Network and the NCI Breast SPORE program. Sera were derived from early-stage breast cancer patients from FCCC (53 cases/53 controls); control sera were sex- and age-matched (+/−2 yrs). All samples were obtained at the time of routine mammography, prior to the diagnosis of cancer, and were selected retrospectively. To control for benign breast disease, we obtained an independent set of sera of early-stage invasive breast cancer patients and age-matched (+/−3 yrs) benign breast disease controls from DUMC (102 cases/102 controls). These samples were collected using a standardized sample collection protocol and stored at −80° C. until use. Cases and matched controls were processed simultaneously. Written consent was obtained from all subjects under institutional review board approval.

Sequence-verified, full-length cDNA expression plasmids in flexible donor vector systems were obtained from the Harvard Institute of Proteomics and are publicly available (see web site dnasu.asu.edu/DNASU/). These were converted to the T7-based mammalian expression vector pANT7_GST using LR recombinase (Invitrogen, Carlsbad, Calif.). Expression plasmids were transformed into *E. coli* DH5α and grown in 1.5 mL terrific broth and ampicillin (100 μg/mL). DNA was purified with the NucleoPrepII anion exchange resin (Macherey-Nagel Inc., Bethlehem, Pa.) using a Biomek FX (Beckman Coulter, Inc., Fullerton, Calif.) automated laboratory workstation. Automated addition of all solutions was accomplished using a Matrix WellMate™ (Thermo Scientific, Hudson, N.H.) rapid bulk liquid-dispensing instrument. Purified DNA was precipitated by addition of 0.6 volumes isopropanol, followed by centrifugation at 5000 rcf for 30 minutes. The DNA pellet was washed with 200 μL of 80% ethanol, centrifuged at 5000 rcf for 15 minutes, dried, and resuspended in dH$_2$O. For bead array ELISAs, larger quantities of DNA were prepared using standard Nucleobond™ preparation methods (Macherey-Nagel Inc., Bethlehem, Pa.).

Plasmid DNA (1.5 μg/μL) was supplemented with capture antibody (50 μg/mL, anti-GST antibody, GE Healthcare Biosciences, Piscataway, N.J.) or anti-FLAG antibody (Sigma-Aldrich, St. Louis, Mo.), protein crosslinker (2 mM, BS3, Pierce, Rockford, Ill.) and BSA (3 mg/mL, Sigma-Aldrich) to the DNA prior to printing onto the array surface. All samples were printed using a Genetix QArray2™ with 300 μm solid tungsten pins on amine-treated glass slides. Arrays were stored in an air-tight container at room temperature, protected from light. The printed DNA was transcribed and translated in situ using previously published protocols. Protein expression was detected using anti-GST MAb (Cell Signaling, Danvers, Mass.) diluted at 1:200. For detecting serum antibodies, the arrays were incubated with serum diluted 1:300-1:600 in 5% PBS milk with 0.2% Tween 20. All incubations were carried out at 4° C. overnight with mixing (Corning hybridization chambers) unless indicated otherwise. Detection on the array was carried out using an anti-human IgG (Jackson ImmunoResearch Labs, West Grove, Pa.) conjugated with HRP. The slides were developed for fluorescent detection using the Tyramide Signal Amplification reagent (PerkinElmer, Waltham, Mass.) per manufacturer's instructions. Slides were scanned with a Perkin Elmer ProScanArray HT and the images were quantitated using MicroVigene software (Vigene Tech version 2.9.9.2). The highly immunogenic EBV-derived antigen, EBNA-1, was included as N- and C-terminal fragments for positive control antigens. Negative controls included empty vectors and no DNA controls. Registration spots for array alignment were printed purified human IgG proteins.

For the first screening stage, 53 cases and 53 control sera from FCCC were screened on 4,988 antigens displayed in NAPPA protein array format. Each array was normalized by first removing the background signal estimated by the first quartile of the non-spots and then log-transforming the median-scaled raw intensities to bring the data to the same scale and stabilize the variance across the range of signals. Candidate antigens from the initial 4,988 antigens were selected if they met two different criteria: 1) comparison of the $95^{th}$ percentiles of the cases and controls using quantile regression and 2) comparison of the proportion of cases with intensities above the $95^{th}$ percentile of controls to the expected number seen by chance, with a p-value ≤0.05 (n=217). Additional antigens (n=544) were ranked based on intensity and decreasing specificity (cases/controls). Independent arrays of these 761 candidate antigens were screened with a fully independent set of age-matched sera consisting of 76 controls with benign breast disease and 102 patient sera from DUMC, randomly divided into training and validation sets. We normalized these arrays as follows. First, we removed differences in intensity associated with plates and pins by consecutively multiplying the raw intensities by three factors: the median intensity of all antigens divided by the median intensity of antigens from the same plate, the median intensity of all antigens divided by the median intensity of antigens printed at the same within-pin position, and the median intensity of all antigens divided by the median intensity of antigens printed with the same pin. These scalings yielded a median reduction in variance of 9%. We removed any duplicate antigen pairs that differed by more than 3 times the median absolute deviation, resulting in removal of 0.5% of spots. Third, we rescaled the raw intensities as above and averaged duplicate antigen pairs. Finally, we removed background signal by subtracting the first quartile of control spot (no DNA) intensity and divided the excess intensity by the median excess intensity.

We used the partial area under the receiver operating characteristic curve (pAUC) as the basis for comparing the normalized intensities of cases and controls for each antigen. Specifically, we used the pAUC where the false positive rate is at most 5%. For each antigen we tested the hypothesis that the pAUC was greater than 0.00125, which is the same partial area under the 45 degree line receiver operating characteristic curve that represents no difference between cases and controls. We used the training set to identify 119 potential antigen biomarkers with p-values less than 0.05 and confirmed 28 of these using the validation set (p<0.05). Training and validation statistics for the 28 breast cancer biomarkers is provided in Table 1.

TABLE 1

| Gene Name | Accession number | Amino acid | Nucleotide |
|---|---|---|---|
| SF3A1 splicing factor 3A subunit 1 isoform 1-full length (1-793) | NP_005868 | SEQ ID NO: 1 | SEQ ID NO: 2 |
| FRS3 fibroblast growth factor receptor substrate 3-full length (1-492) | NP_006644 | SEQ ID NO: 3 | SEQ ID NO: 4 |
| BAT4 HLA-B associated transcript-4-full length (1-356) | NP_149417 | SEQ ID NO: 5 | SEQ ID NO: 6 |
| HOXD1 homeobox protein Hox-D1 full length (1-328) | AAH14477 | SEQ ID NO: 7 | SEQ ID NO: 8 |
| CSNK1E casein kinase I isoform epsilon full length (1-416) | NP_001885 | SEQ ID NO: 9 | SEQ ID NO: 10 |
| SLC33A1 acetyl-coenzyme A transporter 1-full length (1-549) | NP_004724 | SEQ ID NO: 11 | SEQ ID NO: 12 |
| ATP6AP1 V-type proton ATPase subunit S1 precursor-full length (1-470) | NP_001174 | SEQ ID NO: 13 | SEQ ID NO: 14 |
| RAC3 ras-related C3 botulinum toxin substrate 3 precursor-full length (1-192) | NP_005043 | SEQ ID NO: 15 | SEQ ID NO: 16 |
| BDNF brain-derived neurotrophic factor transcript variant 5-full length (1-247) | AAA96140 | SEQ ID NO: 17 | SEQ ID NO: 18 |
| ATF3 cyclic AMP-dependent transcription factor ATF-3 isoform 1-full length (1-181) | NP_001665 | SEQ ID NO: 19 | SEQ ID NO: 20 |
| PDCD6IP programmed cell death 6-interacting protein isoform 1-full length (1-868) | NP_037506 | SEQ ID NO: 21 | SEQ ID NO: 22 |
| RAB5A ras-related protein Rab-5A-full length (1-215) | NP_004153 | SEQ ID NO: 23 | SEQ ID NO: 24 |

TABLE 1-continued

| Gene Name | Accession number | Amino acid | Nucleotide |
|---|---|---|---|
| DBT Dihydrolipoamide branched chain transacylase E2-full length (1-482) | AAH16675 | SEQ ID NO: 25 | SEQ ID NO: 26 |
| ALG10 alpha-1,2-glucosyltransferase ALG10-A-full length(1-473) | NP_116223 | SEQ ID NO: 27 | SEQ ID NO: 28 |
| CTBP1 C-terminal-binding protein 1 isoform 1-full length (1-440) | NP_001319 | SEQ ID NO: 29 | SEQ ID NO: 30 |
| SOX2 transcription factor SOX-2-full length (1-317) | NP_003097 | SEQ ID NO: 31 | SEQ ID NO: 32 |
| MYOZ2 myozenin-2-full length (1-264) | NP_057683 | SEQ ID NO: 33 | SEQ ID NO: 34 |
| C15orf48 normal mucosa of esophagus-specific gene 1 protein-full length (1-83) | NP_115789 | SEQ ID NO: 35 | SEQ ID NO: 36 |
| TRIM32 E3 ubiquitin-protein ligase TRIM32-full length (1-653) | NP_001093149 | SEQ ID NO: 37 | SEQ ID NO: 38 |
| EIF3E eukaryotic translation initiation factor 3 subunit E-full length (1-445) | NP_001559 | SEQ ID NO: 39 | SEQ ID NO: 40 |
| ZMYM6 zinc finger, MYM-type 6, isoform CRA_b-partial (1-156/163) | AAP35781 | SEQ ID NO: 41 | SEQ ID NO: 42 |
| GPR157 probable G-protein coupled receptor 157-partial (1-155/335) | EAW71612 | SEQ ID NO: 43 | SEQ ID NO: 44 |
| BMX cytoplasmic tyrosine-protein kinase BMX-full length (1-675) | NP_001712 | SEQ ID NO: 45 | SEQ ID NO: 46 |
| UBAP1 ubiquitin-associated protein 1 isoform 1-full length (1-502) | NP_057609 | SEQ ID NO: 47 | SEQ ID NO: 48 |
| TFCP2 grainyhead-like 3 (Drosophila), isoform CRA_d-full length (1-555) | AAH36890 | SEQ ID NO: 49 | SEQ ID NO: 50 |
| SERPINH1 serpin H1 precursor-full length (1-418) | NP_001226 | SEQ ID NO: 51 | SEQ ID NO: 52 |
| ZNF510 zinc finger protein 510-partial (1-636/683) | AAH68587 | SEQ ID NO: 53 | SEQ ID NO: 54 |
| SELL L-selectin precursor-full length (1-375) | AAH20758 | SEQ ID NO: 55 | SEQ ID NO: 56 |

We claim:

1. A method comprising;
   (a) contacting a serum or plasma sample obtained from a subject having or at risk of having breast cancer with a polypeptide probe set bound to a surface of a solid support, wherein the polypeptide probe set comprises CTBP1 polypeptide (SEQ ID NO: 29) or an antigenic fragment thereof, BDNF (SEQ ID NO: 17) or an antigenic fragment thereof, GPR157 (SEQ ID NO: 43) or an antigenic fragment thereof, and one or more additional polypeptides selected from the group consisting of ATP6AP1 (SEQ ID NO: 13), PDCD6IP (SEQ ID NO: 21), DBT (SEQ ID NO: 25), CSNK1E (SEQ ID NO: 9), FRS3 (SEQ ID NO: 3), RAC3 (SEQ ID NO: 15), HOXD1 (SEQ ID NO: 7), SF3A1 (SEQ ID NO: 1), C15orf48 (SEQ ID NO: 35), MYOZ2 (SEQ ID NO: 33), EIF3E (SEQ ID NO: 39), BAT4 (SEQ ID NO: 5), ATF3 (SEQ ID NO: 19), BMX (SEQ ID NO: 45), RAB5A (SEQ ID NO: 23), UBAP1 (SEQ ID NO: 47), SOX2 (SEQ ID NO: 31), ZMYM6 (SEQ ID NO: 41), SLC33A1 (SEQ ID NO: 11), TRIM32 (SEQ ID NO: 37), ALG10 (SEQ ID NO: 27), TFCP2 (SEQ ID NO: 49), SERPINH1 (SEQ ID NO: 51), SELL (SEQ ID NO: 55), ZNF510 (SEQ ID NO: 53), and antigenic fragments thereof; wherein the contacting occurs under conditions whereby antibodies, if present in the bodily fluid, selectively bind to the polypeptides bound to the surface;
   (b) detecting presence of antibodies to the polypeptides in the sample;
   wherein the presence of antibodies in the sample to the one or more polypeptides is used to diagnose breast cancer in the subject, and wherein detecting comprises normalizing intensities for each polypeptide of the probe set and comparing normalized intensities with a control using partial area under a receiver operating characteristic curve (pAUC) with a false positive rate no greater than 5 percent; and
   (c) administering a therapeutic agent to the subject to treat the breast cancer.

2. The method of claim 1, wherein the polypeptide probe set further comprises ATP6AP1 (SEQ ID NO: 13), or an antigenic fragment thereof.

3. The method of claim 1, wherein the subject has one or more of a lump in breast tissue, lymph nodes, or armpit; changes in breast size or shape, skin dimpling, nipple inversion, spontaneous single-nipple discharge, a family/personal history of breast cancer, or the subject is a carrier of a mutation in BRCA.

4. The method of claim 1, wherein the breast cancer is Stage I or Stage II breast cancer.

5. The method of claim 1, wherein the detecting comprises use of a labeled antibody.

6. The method of claim 1, wherein the subject is further tested for the presence of breast cancer using a technique selected from the group consisting of mammography, biopsy, or magnetic resonance imaging.

7. The method of claim 1, wherein the polypeptide probe set further comprises two or more additional polypeptides selected from the group recited in claim 1.

8. The method of claim 1, wherein each polypeptide of the polypeptide probe set is bound to the surface using Nucleic Acid Programmable Protein Array (NAPPA) technology.

* * * * *

SEQUENCE LISTING

<160> NUMBER OF SEQ ID NOS: 56

<210> SEQ ID NO 1
<211> LENGTH: 793
<212> TYPE: PRT
<213> ORGANISM: Homo sapiens

<400> SEQUENCE: 1

Met Pro Ala Gly Pro Val Gln Ala Val Pro Pro Pro Pro Val Pro
1               5                   10                  15

Thr Glu Pro Lys Gln Pro Thr Glu Glu Ala Ser Ser Lys Glu Asp
                20                  25                  30

Ser Ala Pro Ser Lys Pro Val Val Gly Ile Ile Tyr Pro Pro Glu
                35                  40                  45

Val Arg Asn Ile Val Asp Lys Thr Ala Ser Phe Val Ala Arg Asn Gly
    50                  55                  60

Pro Glu Phe Glu Ala Arg Ile Arg Gln Asn Glu Ile Asn Asn Pro Lys
65                  70                  75                  80

Phe Asn Phe Leu Asn Pro Asn Asp Pro Tyr His Ala Tyr Tyr Arg His
                85                  90                  95

Lys Val Ser Glu Phe Lys Glu Gly Lys Ala Gln Glu Pro Ser Ala Ala
                100                 105                 110

Ile Pro Lys Val Met Gln Gln Gln Gln Thr Thr Gln Gln Gln Leu
                115                 120                 125

Pro Gln Lys Val Gln Ala Gln Val Ile Gln Thr Ile Val Pro Lys
                130                 135                 140

Glu Pro Pro Pro Glu Phe Glu Phe Ile Ala Asp Pro Pro Ser Ile Ser
145                 150                 155                 160

Ala Phe Asp Leu Asp Val Val Lys Leu Thr Ala Gln Phe Val Ala Arg
                165                 170                 175

Asn Gly Arg Gln Phe Leu Thr Gln Leu Met Gln Lys Glu Gln Arg Asn
                180                 185                 190

Tyr Gln Phe Asp Phe Leu Arg Pro Gln His Ser Leu Phe Asn Tyr Phe
                195                 200                 205

Thr Lys Leu Val Glu Gln Tyr Thr Lys Ile Leu Ile Pro Pro Lys Gly
                210                 215                 220

Leu Phe Ser Lys Leu Lys Glu Ala Glu Asn Pro Arg Glu Val Leu
225                 230                 235                 240

Asp Gln Val Cys Tyr Arg Val Glu Trp Ala Lys Phe Gln Glu Arg Glu
                245                 250                 255

Arg Lys Lys Glu Glu Glu Glu Lys Glu Lys Glu Arg Val Ala Tyr Ala
                260                 265                 270

Gln Ile Asp Trp His Asp Phe Val Val Glu Thr Val Asp Phe Gln
                275                 280                 285

Pro Asn Glu Gln Gly Asn Phe Pro Pro Thr Thr Pro Glu Glu Leu
                290                 295                 300

Gly Ala Arg Ile Leu Ile Gln Glu Arg Tyr Glu Lys Phe Gly Glu Ser
305                 310                 315                 320

Glu Glu Val Glu Met Glu Val Glu Ser Asp Glu Glu Asp Lys Gln
                325                 330                 335

Glu Lys Ala Glu Glu Pro Ser Gln Leu Asp Gln Asp Thr Gln Val
                340                 345                 350

Gln Asp Met Asp Glu Gly Ser Asp Asp Glu Glu Glu Gly Gln Lys Val
                355                 360                 365

```
Pro Pro Pro Glu Thr Pro Met Pro Pro Leu Pro Thr Pro
    370             375             380

Asp Gln Val Ile Val Arg Lys Asp Tyr Asp Pro Lys Ala Ser Lys Pro
385                 390                 395                 400

Leu Pro Pro Ala Pro Ala Pro Asp Glu Tyr Leu Val Ser Pro Ile Thr
                405                 410                 415

Gly Glu Lys Ile Pro Ala Ser Lys Met Gln Glu His Met Arg Ile Gly
            420                 425                 430

Leu Leu Asp Pro Arg Trp Leu Glu Gln Arg Asp Arg Ser Ile Arg Glu
        435                 440                 445

Lys Gln Ser Asp Asp Glu Val Tyr Ala Pro Gly Leu Asp Ile Glu Ser
450                 455                 460

Ser Leu Lys Gln Leu Ala Glu Arg Arg Thr Asp Ile Phe Gly Val Glu
465                 470                 475                 480

Glu Thr Ala Ile Gly Lys Lys Ile Gly Glu Glu Ile Gln Lys Pro
                485                 490                 495

Glu Glu Lys Val Thr Trp Asp Gly His Ser Gly Ser Met Ala Arg Thr
            500                 505                 510

Gln Gln Ala Ala Gln Ala Asn Ile Thr Leu Gln Glu Gln Ile Glu Ala
        515                 520                 525

Ile His Lys Ala Lys Gly Leu Val Pro Glu Asp Asp Thr Lys Glu Lys
    530                 535                 540

Ile Gly Pro Ser Lys Pro Asn Glu Ile Pro Gln Gln Pro Pro Pro Pro
545                 550                 555                 560

Ser Ser Ala Thr Asn Ile Pro Ser Ser Ala Pro Pro Ile Thr Ser Val
                565                 570                 575

Pro Arg Pro Pro Thr Met Pro Pro Val Arg Thr Thr Val Val Ser
            580                 585                 590

Ala Val Pro Val Met Pro Arg Pro Pro Met Ala Ser Val Val Arg Leu
        595                 600                 605

Pro Pro Gly Ser Val Ile Ala Pro Met Pro Pro Ile His Ala Pro
    610                 615                 620

Arg Ile Asn Val Val Pro Met Pro Pro Ser Ala Pro Pro Ile Met Ala
625                 630                 635                 640

Pro Arg Pro Pro Met Ile Val Pro Thr Ala Phe Val Pro Ala Pro
                645                 650                 655

Pro Val Ala Pro Val Pro Ala Pro Ala Pro Met Pro Pro Val His Pro
            660                 665                 670

Pro Pro Pro Met Glu Asp Glu Pro Thr Ser Lys Lys Leu Lys Thr Glu
        675                 680                 685

Asp Ser Leu Met Pro Glu Glu Glu Phe Leu Arg Arg Asn Lys Gly Pro
    690                 695                 700

Val Ser Ile Lys Val Gln Val Pro Asn Met Gln Asp Lys Thr Glu Trp
705                 710                 715                 720

Lys Leu Asn Gly Gln Val Leu Val Phe Thr Leu Pro Leu Thr Asp Gln
                725                 730                 735

Val Ser Val Ile Lys Val Lys Ile His Glu Ala Thr Gly Met Pro Ala
            740                 745                 750

Gly Lys Gln Lys Leu Gln Tyr Glu Gly Ile Phe Ile Lys Asp Ser Asn
        755                 760                 765

Ser Leu Ala Tyr Tyr Asn Met Ala Asn Gly Ala Val Ile His Leu Ala
    770                 775                 780

Leu Lys Glu Arg Gly Gly Arg Lys Lys
```

<210> SEQ ID NO 2
<211> LENGTH: 2379
<212> TYPE: DNA
<213> ORGANISM: Homo sapiens

<400> SEQUENCE: 2

```
atgccggccg acccgtgca ggcggtgccc ccgccgccgc ccgtgcccac ggagcccaaa      60
cagcccacag aagaagaagc atcttcaaag gaggattctg caccttctaa gccagttgtg     120
gggattattt accctcctcc agaggtcaga aatattgttg acaagactgc cagctttgtg     180
gccagaaacg ggcctgaatt tgaagctagg atccgacaga acgagatcaa caaccccaag     240
ttcaactttc tgaaccccaa tgacccttac catgcctact accgccacaa ggtcagcgag     300
ttcaaggaag ggaaggctca ggagccgtcc gccgccatcc caaggtcat gcagcagcag      360
cagcagacca cccagcagca gctgccccag aaggtccaag cccaagtaat ccaagagacc     420
atcgtgccca agagcctcc tcctgagttt gagttcattg ctgatcctcc ctctatctca     480
gccttcgact tggatgtggt gaagctgacg gctcagtttg tggccaggaa tgggcgccag     540
tttctgaccc agctgatgca gaaagagcag cgcaactacc agtttgactt ctcccgccca     600
cagcacagcc tcttcaacta cttcacgaag ctagtggaac agtacaccaa gatcttgatt     660
ccacccaaag gtttatttc aaagctcaag aaagaggctg aaaaccccg agaagttttg       720
gatcaggtgt gttaccgagt ggaatgggcc aaattccagg aacgtgagag gaagaaggaa     780
gaagaggaga aggagaagga gcgggtggcc tatgctcaga tcgactggca tgattttgtg     840
gtggtggaaa cagtggactt ccaacccaat gagcaaggga acttccctcc ccccaccacg     900
ccagaggagc tggggcccg aatcctcatt caggagcgct atgaaaagtt tgggagagt       960
gaggaagttg agatggaggt cgagtctgat gaggaggatg acaaacagga aaggcggag     1020
gagcctcctt cccagctgga ccaggacacc caagtacaag atatggatga gggttcagat    1080
gatgaagaag aagggcagaa agtgccccca ccccagaga cacccatgcc tccacctctg     1140
ccccaactc cagaccaagt cattgtccgc aaggattatg atcccaaagc ctccaagccc     1200
ttgcctccag cccctgctcc agatgagtat cttgtgtccc ccattactgg ggagaagatc    1260
cccgccagca aaatgcagga acacatgcgc attggacttc ttgaccctcg ctggctggag    1320
cagcgggatc gctccatccg tgagaagcag agcgatgatg aggtgtacgc accaggtctg    1380
gatattgaga gcagcttgaa gcagttggct gagcggcgta ctgacatctt cggtgtagag    1440
gaaacagcca ttggtaagaa gatcggtgag gaggagatcc agaagccaga ggaaaaggtg    1500
acctgggatg ccactcagg cagcatggcc ggacccagc aggctgccca ggccaacatc     1560
accctccagg agcagattga ggccattcac aaggccaaag cctggtgcc agaggatgac    1620
actaaagaga gattggccc cagcaagccc aatgaaatcc ctcaacagcc accgccacca    1680
tcttcagcca ccaacatccc cagctcggct ccacccatca cttcagtgcc ccgaccaccc    1740
acaatgccac ctccagttcg tactacagtt gtctccgcag tacccgtcat gccccggccc   1800
ccaatggcat ctgtggtccg gctgccccca ggtcagtga tcgcccccat gccgccatc    1860
atccacgcgc ccagaatcaa cgtggtgccc atgcctccct cggcccctcc tattatggcc    1920
ccccgcccac cccccatgat tgtgccaaca gcctttgtgc ctgctccacc tgtggcacct    1980
gtcccagctc cagccccaat gcccctgtg catcccccac ctcccatgga agatgagccc    2040
acctccaaaa aactgaagac agaggacagc ctcatgccag aggaggagtt cctgcgcaga    2100
```

```
aacaagggtc cagtgtccat caaagtccag gtgcccaaca tgcaggataa gacggaatgg    2160
aaactgaatg ggcaggtgct ggtcttcacc ctcccactca cggaccaggt ctctgtcatt    2220
aaggtgaaga ttcatgaagc cacaggcatg cctgcaggga acagaagct acagtatgag     2280 ggtatcttca tcaaagattc caactcactg gcttactaca acatggccaa tggcgcagtc    2340
atccacctgg ccctcaagga gagaggcggg aggaagaag                           2379
```

<210> SEQ ID NO 3
<211> LENGTH: 492
<212> TYPE: PRT
<213> ORGANISM: Homo sapiens

<400> SEQUENCE: 3

```
Met Gly Ser Cys Cys Ser Cys Leu Asn Arg Asp Ser Val Pro Asp Asn
1               5                   10                  15

His Pro Thr Lys Phe Lys Val Thr Asn Val Asp Asp Glu Gly Val Glu
            20                  25                  30

Leu Gly Ser Gly Val Met Glu Leu Thr Gln Ser Glu Leu Val Leu His
        35                  40                  45

Leu His Arg Arg Glu Ala Val Arg Trp Pro Tyr Leu Cys Leu Arg Arg
    50                  55                  60

Tyr Gly Tyr Asp Ser Asn Leu Phe Ser Phe Glu Ser Gly Arg Arg Cys
65                  70                  75                  80

Gln Thr Gly Gln Gly Ile Phe Ala Phe Lys Cys Ser Arg Ala Glu Glu
                85                  90                  95

Ile Phe Asn Leu Leu Gln Asp Leu Met Gln Cys Asn Ser Ile Asn Val
            100                 105                 110

Met Glu Glu Pro Val Ile Ile Thr Arg Asn Ser His Pro Ala Glu Leu
        115                 120                 125

Asp Leu Pro Arg Ala Pro Gln Pro Pro Asn Ala Leu Gly Tyr Thr Val
    130                 135                 140

Ser Ser Phe Ser Asn Gly Cys Pro Gly Glu Gly Pro Arg Phe Ser Ala
145                 150                 155                 160

Pro Arg Arg Leu Ser Thr Ser Ser Leu Arg His Pro Ser Leu Gly Glu
                165                 170                 175

Glu Ser Thr His Ala Leu Ile Ala Pro Asp Glu Gln Ser His Thr Tyr
            180                 185                 190

Val Asn Thr Pro Ala Ser Glu Asp Asp His Arg Arg Gly Arg His Cys
        195                 200                 205

Leu Gln Pro Leu Pro Glu Gly Gln Ala Pro Phe Leu Pro Gln Ala Arg
    210                 215                 220

Gly Pro Asp Gln Arg Asp Pro Gln Val Phe Leu Gln Pro Gly Gln Val
225                 230                 235                 240

Lys Phe Val Leu Gly Pro Thr Pro Ala Arg Arg His Met Val Lys Cys
                245                 250                 255

Gln Gly Leu Cys Pro Ser Leu His Asp Pro Pro His His Asn Asn Asn
            260                 265                 270

Asn Glu Ala Pro Ser Glu Cys Pro Ala Gln Pro Lys Cys Thr Tyr Glu
        275                 280                 285

Asn Val Thr Gly Gly Leu Trp Arg Gly Ala Gly Trp Arg Leu Ser Pro
    290                 295                 300

Glu Glu Pro Gly Trp Asn Gly Leu Ala His Arg Arg Ala Ala Leu Leu
305                 310                 315                 320
```

```
His Tyr Glu Asn Leu Pro Pro Leu Pro Pro Val Trp Glu Ser Gln Ala
            325                 330                 335

Gln Gln Leu Gly Gly Glu Ala Gly Asp Gly Asp Ser Arg Asp Gly
        340                 345                 350

Leu Thr Pro Ser Ser Asn Gly Phe Pro Asp Gly Glu Glu Asp Glu Thr
            355                 360                 365

Pro Leu Gln Lys Pro Thr Ser Thr Arg Ala Ala Ile Arg Ser His Gly
        370                 375                 380

Ser Phe Pro Val Pro Leu Thr Arg Arg Gly Ser Pro Arg Val Phe
385                 390                 395                 400

Asn Phe Asp Phe Arg Arg Pro Gly Pro Glu Pro Arg Gln Leu Asn
                405                 410                 415

Tyr Ile Gln Val Glu Leu Lys Gly Trp Gly Gly Asp Arg Pro Lys Gly
            420                 425                 430

Pro Gln Asn Pro Ser Ser Pro Gln Ala Pro Met Pro Thr Thr His Pro
        435                 440                 445

Ala Arg Ser Ser Asp Ser Tyr Ala Val Ile Asp Leu Lys Lys Thr Val
    450                 455                 460

Ala Met Ser Asn Leu Gln Arg Ala Leu Pro Arg Asp Asp Gly Thr Ala
465                 470                 475                 480

Arg Lys Thr Arg His Asn Ser Thr Asp Leu Pro Leu
            485                 490

<210> SEQ ID NO 4
<211> LENGTH: 1476
<212> TYPE: DNA
<213> ORGANISM: Homo sapiens

<400> SEQUENCE: 4 atgggagct gctgcagctg cctgaacaga gacagcgttc cagacaacca ccccaccaag      60
ttcaaggtga caaatgtgga tgatgagggg gtggagctgg gctctggggt gatggagctg     120
acgcagagtg agctggtgct gcacctgcat cggcgtgagg ccgtccgctg gccttatctc     180
tgcttgcggc gctatggcta cgactccaac ctcttctcct ttgagagtgg ccgccgatgt     240
cagacaggcc agggaatatt tgcatttaag tgttcccggg ctgaggaaat cttcaacctc     300
cttcaggatc tgatgcagtg caacagcatc aatgtgatgg aagagcctgt catcatcacc     360
cgcaatagcc accccgctga gcttgacctc cctcgagccc cccagccacc caatgctcta     420
ggctacactg tctccagctt tccaatggc tgccctggag agggcccacg attctcagct     480
cccccggcgg tctcgacaag cagcctgcgg cacccctcgc ttggggaaga gtccacccat     540
gccctcattg ctcctgatga gcagtcccac acctatgtca acacaccggc cagtgaagat     600
gaccaccgca gggccgcca ctgcctgcag cccctgcctg agggtcaggc acccttcctc     660
ccgcaggccc gggacctga ccaacgggac ccacaggtgt tcttgcagcc aggccaggtg     720
aagtttgtgt tgggcccgac ccctgctcgg cggcacatgg tgaagtgcca gggcctctgt     780
cccagcctgc atgacccccc acaccacaat aataacaatg aggcccttc tgagtgtcca     840 gcccagccca gtgcaccta cgagaacgtc accgggggc tgtggcgagg gctggctgg      900 agactgagcc agaggagcc gggctggaat ggccttgccc accgcgggc cgccctgctg     960 cactatgaga acctgccccc actgcccct gtgtgggaaa gccaagccca gcagctggga    1020
ggggaggctg gggatgatgg ggactcgagg gatgggctca cccctcttc caatggcttc    1080 cctgatggtg aggaggacga gaccccactg cagaagccca ccagcacccg ggccgccatc    1140
```

-continued

```
cgcagccacg gcagctttcc tgtgccactg acccgccgcc gcggctcccc aagggtcttc    1200
aactttgatt ccgccggcc ggggcccgag cccccaaggc agcttaacta catccaggtg    1260
gagctaaagg gctggggtgg agaccgccct aaggggcccc agaaccctc gagccccaa     1320 gcccccatgc ccaccaccca ccctgccga agctcagact cctacgccgt gattgacctc    1380
aaaaagaccg tggccatgtc caacctgcag agagctctgc cccgagacga tggcaccgcc    1440
aggaaaaccc ggcacaacag caccgacctg cctctg                              1476
```

<210> SEQ ID NO 5
<211> LENGTH: 356
<212> TYPE: PRT
<213> ORGANISM: Homo sapiens

<400> SEQUENCE: 5

```
Met Ser Arg Pro Leu Leu Ile Thr Phe Thr Pro Ala Thr Asp Pro Ser
1               5                   10                  15

Asp Leu Trp Lys Asp Gly Gln Gln Pro Gln Pro Glu Lys Pro Glu
            20                  25                  30

Ser Thr Leu Asp Gly Ala Ala Arg Ala Phe Tyr Glu Ala Leu Ile
        35                  40                  45

Gly Asp Glu Ser Ser Ala Pro Asp Ser Gln Arg Ser Gln Thr Glu Pro
50                  55                  60

Ala Arg Glu Arg Lys Arg Lys Lys Arg Ile Met Lys Ala Pro Ala
65                  70                  75                  80

Ala Glu Ala Val Ala Glu Gly Ala Ser Gly Arg His Gly Gln Gly Arg
                85                  90                  95

Ser Leu Glu Ala Glu Asp Lys Met Thr His Arg Ile Leu Arg Ala Ala
            100                 105                 110

Gln Glu Gly Asp Leu Pro Glu Leu Arg Arg Leu Leu Glu Pro His Glu
        115                 120                 125

Ala Gly Gly Ala Gly Gly Asn Ile Asn Ala Arg Asp Ala Phe Trp Trp
    130                 135                 140

Thr Pro Leu Met Cys Ala Ala Arg Ala Gly Gln Gly Ala Ala Val Ser
145                 150                 155                 160

Tyr Leu Leu Gly Arg Gly Ala Ala Trp Val Gly Val Cys Glu Leu Ser
                165                 170                 175

Gly Arg Asp Ala Ala Gln Leu Ala Glu Glu Ala Gly Phe Pro Glu Val
            180                 185                 190

Ala Arg Met Val Arg Glu Ser His Gly Glu Thr Arg Ser Pro Glu Asn
        195                 200                 205

Arg Ser Pro Thr Pro Ser Leu Gln Tyr Cys Glu Asn Cys Asp Thr His
    210                 215                 220

Phe Gln Asp Ser Asn His Arg Thr Ser Thr Ala His Leu Leu Ser Leu
225                 230                 235                 240

Ser Gln Gly Pro Gln Pro Pro Asn Leu Pro Leu Gly Val Pro Ile Ser
                245                 250                 255

Ser Pro Gly Phe Lys Leu Leu Leu Arg Gly Gly Trp Glu Pro Gly Met
            260                 265                 270

Gly Leu Gly Pro Arg Gly Glu Gly Arg Ala Asn Pro Ile Pro Thr Val
        275                 280                 285

Leu Lys Arg Asp Gln Glu Gly Leu Gly Tyr Ser Ala Pro Gln Pro
    290                 295                 300

Arg Val Thr His Phe Pro Ala Trp Asp Thr Arg Ala Val Ala Gly Arg
305                 310                 315                 320
```

Glu Arg Pro Pro Arg Val Ala Thr Leu Ser Trp Arg Glu Arg Arg
            325                 330                 335

Arg Glu Glu Lys Asp Arg Ala Trp Glu Arg Asp Leu Arg Thr Tyr Met
        340                 345                 350

Asn Leu Glu Phe
        355

<210> SEQ ID NO 6
<211> LENGTH: 1068
<212> TYPE: DNA
<213> ORGANISM: Homo sapiens

<400> SEQUENCE: 6

```
atgtcccggc ccttgctcat caccttcacc ccagccactg accccagcga cctctggaag      60
gatgggcagc agcagccaca gcccgagaag ccagagtcca ccctggatgg ggctgcagcc     120
cgagctttct atgaggccct gattggggat gagagcagcg ctcctgactc ccagagatct     180
cagactgaac ctgccagaga agaaaagaga agaaaagaa gaataatgaa ggcaccagca     240
gcagaagcag tggcagaagg agcatcagga agacatggac aagggagatc ccttgaggct     300
gaggataaga tgactcaccg atactgagg gcagcccagg aggggaccct gccagaactt     360
aggagactgc tggaaccgca tgaggcagga ggagctgggg ggaatatcaa cgcccgggat     420
gccttctggt ggaccccact gatgtgtgct gctcgagcgg gccaggggggc agctgtgagc     480
tatctcctgg gccgtggggc tgcctgggtg ggggtctgtg agctgagtgg cagggatgcg     540
gctcagctcg ctgaagaagc tggcttccct gaggtagccc gcatggtcag ggagagccat     600
ggagagacaa ggagcccgga aaaccggtct cctactccct ccctccagta ctgcgagaac     660
tgtgacaccc acttccaaga ttccaaccac cgcacatcca ctgctcacct gctgtcactg     720
tcgcagggtc ctcagcctcc caaccttcca cttggggtgc ccatctccag cccgggcttc     780
aaactgctgc tgaggggggg ctgggagcca ggaatgggc tgggaccccg gggtgagggc     840
cgtgccaatc ccatccccac tgtcctcaag agggaccagg aaggactagg ctacagatca     900
gcaccccagc cccgagtgac acatttccca gcttgggata cccagctgt ggctgggagg     960
gagagacccc ctcgggtggc cacactgagc tggaggggagg agagaaggag ggaggagaaa    1020
gacagggctt gggagcggga tctaaggact acatgaacc tcgagttc                  1068
```

<210> SEQ ID NO 7
<211> LENGTH: 328
<212> TYPE: PRT
<213> ORGANISM: Homo sapiens

<400> SEQUENCE: 7

Met Ser Ser Tyr Leu Glu Tyr Val Ser Cys Ser Ser Gly Gly Val
1               5                   10                  15

Gly Gly Asp Val Leu Ser Leu Ala Pro Lys Phe Cys Arg Ser Asp Ala
            20                  25                  30

Arg Pro Val Ala Leu Gln Pro Ala Phe Pro Leu Gly Asn Gly Asp Gly
        35                  40                  45

Ala Phe Val Ser Cys Leu Pro Leu Ala Ala Ala Arg Pro Ser Pro Ser
    50                  55                  60

Pro Pro Ala Ala Pro Ala Arg Pro Ser Val Pro Pro Ala Ala Pro
65                  70                  75                  80

Gln Tyr Ala Gln Cys Thr Leu Glu Gly Ala Tyr Glu Pro Gly Ala Ala
                85                  90                  95

Pro Ala Ala Ala Gly Gly Ala Asp Tyr Gly Phe Leu Gly Ser Gly
            100                 105                 110

Pro Ala Tyr Asp Phe Pro Gly Val Leu Gly Arg Ala Ala Asp Asp Gly
        115                 120                 125

Gly Ser His Val His Tyr Ala Thr Ser Ala Val Phe Gly Gly Gly
    130                 135                 140

Ser Phe Leu Leu Ser Gly Gln Val Asp Tyr Ala Ala Phe Gly Glu Pro
145                 150                 155                 160

Gly Pro Phe Ser Ala Cys Leu Lys Ala Ser Ala Asp Gly His Pro Gly
                165                 170                 175

Ala Phe Gln Thr Ala Ser Pro Ala Pro Gly Thr Tyr Pro Lys Ser Val
            180                 185                 190

Ser Pro Ala Ser Gly Leu Pro Ala Ala Phe Ser Thr Phe Glu Trp Met
        195                 200                 205

Lys Val Lys Arg Asn Ala Ser Lys Gly Lys Leu Ala Glu Tyr Gly
    210                 215                 220

Ala Ala Ser Pro Ser Ser Ala Ile Arg Thr Asn Phe Ser Thr Lys Gln
225                 230                 235                 240

Leu Thr Glu Leu Glu Lys Glu Phe His Phe Asn Lys Tyr Leu Thr Arg
                245                 250                 255

Ala Arg Arg Ile Glu Ile Ala Asn Cys Leu His Leu Asn Asp Thr Gln
            260                 265                 270

Val Lys Ile Trp Phe Gln Asn Arg Arg Met Lys Gln Lys Lys Arg Glu
        275                 280                 285

Arg Glu Gly Leu Leu Ala Thr Ala Ile Pro Val Ala Pro Leu Gln Leu
    290                 295                 300

Pro Leu Ser Gly Thr Thr Pro Thr Lys Phe Ile Lys Asn Pro Gly Ser
305                 310                 315                 320

Pro Ser Gln Ser Gln Glu Pro Ser
                325

<210> SEQ ID NO 8
<211> LENGTH: 984
<212> TYPE: DNA
<213> ORGANISM: Homo sapiens

<400> SEQUENCE: 8
atgagctcct acctggagta cgtgtcatgc agcagcagcg gcggggtcgg cggcgacgtg      60
ctcagcttgg cacccaagtt ctgccgctcc gacgcccggc cgtggctct gcagcccgcc     120 ttccctctgg gcaacggcga cggcgccttc gtcagctgtc tgcccctggc cgccgcccga     180
ccctcgcctt cgcccccggc cgcccccgcg cggccgtccg taccgcctcc ggccgcgccc     240
cagtacgcgc agtgcaccct ggagggggcc tacgaacctg gtgccgcacc tgccgcggca     300
gctgggggcg cggactacgg cttcctgggg tccggccgg cgtacgactt cccgggcgtg     360
ctggggcggg cggccgacga cggcgggtct cacgtccact acgccacctc ggccgtcttc     420
tcgggcggcg gctctttcct cctcagcggc caggtggatt acgcggcctt cggcgaaccc     480
ggcccttttt cggcttgtct caaagcgtca gccgacggcc accctggtgc tttccagacc     540
gcatccccgg ccccaggcac ctaccccaag tccgtctctc cgcctccgg cctccctgcc     600 gccttcagca cgttcgagtg gatgaaagtg aagaggaatg cctctaagaa aggcaaactc     660
gccgagtatg gggccgctag ccccctccagc gcgatccgca cgaatttcag caccaagcaa     720
ctgacagaac tggaaaaaga gtttcatttc aataagtact taactcgagc ccggcgcatc     780

```
gagatagcca actgcttgca cctgaatgac acgcaagtca aaatctggtt ccagaaccgc    840
aggatgaaac agaagaaaag ggaacgagaa gggcttctgg ccacggccat tcctgtggct    900
cccctccaac ttcccctctc tggaacaacc cccactaagt ttatcaagaa ccccggcagc    960
ccttctcagt cccaagagcc ttcg                                           984
```

<210> SEQ ID NO 9
<211> LENGTH: 416
<212> TYPE: PRT
<213> ORGANISM: Homo sapiens

<400> SEQUENCE: 9

```
Met Glu Leu Arg Val Gly Asn Lys Tyr Arg Leu Gly Arg Lys Ile Gly
1               5                   10                  15

Ser Gly Ser Phe Gly Asp Ile Tyr Leu Gly Ala Asn Ile Ala Ser Gly
            20                  25                  30

Glu Glu Val Ala Ile Lys Leu Glu Cys Val Lys Thr Lys His Pro Gln
        35                  40                  45

Leu His Ile Glu Ser Lys Phe Tyr Lys Met Met Gln Gly Gly Val Gly
    50                  55                  60

Ile Pro Ser Ile Lys Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
    210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285

Asp Trp Asn Met Leu Lys Phe Gly Ala Ala Arg Asn Pro Glu Asp Val
    290                 295                 300

Asp Arg Glu Arg Arg Glu His Glu Arg Glu Glu Arg Met Gly Gln Leu
305                 310                 315                 320

Arg Gly Ser Ala Thr Arg Ala Leu Pro Pro Gly Pro Pro Thr Gly Ala
                325                 330                 335
```

```
Thr Ala Asn Arg Leu Arg Ser Ala Ala Glu Pro Val Ala Ser Thr Pro
            340                 345                 350

Ala Ser Arg Ile Gln Pro Ala Gly Asn Thr Ser Pro Arg Ala Ile Ser
        355                 360                 365

Arg Val Asp Arg Glu Arg Lys Val Ser Met Arg Leu His Arg Gly Ala
    370                 375                 380

Pro Ala Asn Val Ser Ser Ser Asp Leu Thr Gly Arg Gln Glu Val Ser
385                 390                 395                 400

Arg Ile Pro Ala Ser Gln Thr Ser Val Pro Phe Asp His Leu Gly Lys
                405                 410                 415

<210> SEQ ID NO 10
<211> LENGTH: 1248
<212> TYPE: DNA
<213> ORGANISM: Homo sapiens

<400> SEQUENCE: 10
atggagctac gtgtggggaa caagtaccgc ctgggacgga agatcgggag cgggtccttc      60
ggagatatct acctgggtgc caacatcgcc tctggtgagg aagtcgccat caagctggag     120
tgtgtgaaga caaagcaccc ccagctgcac atcgagagca agttctacaa gatgatgcag     180
ggtggcgtgg ggatcccgtc catcaagtgg tgcggagctg agggcgacta caacgtgatg     240
gtcatggagc tgctggggcc tagcctcgag gacctgttca acttctgttc ccgcaaattc     300
agcctcaaga cggtgctgct cttggccgac cagatgatca gccgcatcga gtatatccac     360
tccaagaact tcatccaccg ggacgtcaag cccgacaact tcctcatggg gctggggaag     420
aagggcaacc tggtctacat catcgacttc ggcctggcca gaagtaccgg gacgcccgc      480 acccaccagc acattcccta ccgggaaaac aagaacctga ccggcacggc ccgctacgct     540
tccatcaaca cgcacctggg cattgagcaa agccgtcgag atgacctgga gcctgggc      600 tacgtgctca tgtacttcaa cctgggctcc ctgccctggc aggggctcaa agcagccacc     660
aagcgccaga agtatgaacg gatcagcgag aagaagatgt caacgcccat cgaggtcctc     720
tgcaaaggct atcccttccga attctcaaca tacctcaact tctgccgctc cctgcgtttt     780
gacgacaagc ccgactactc ttacctacgt cagctcttcc gcaacctctt ccaccggcag     840
ggcttctcct atgactacgt ctttgactgg aacatgctga aattcggtgc agcccggaat     900
cccgaggatg tggaccggga gcggcgagaa cacgaacgcg aggagaggat ggggcagcta     960
cgggggtccg cgacccgagc cctgcccct ggcccaccca cgggggccac tgccaaccgg    1020
ctccgcagtg ccgccgagcc cgtggcttcc acgccagcct cccgcatcca gccggctggc    1080
aatacttctc ccagagcgat ctcgcgggtc gaccgggaga ggaaggtgag tatgaggctg    1140 cacagggtg cgcccgccaa cgtctcctcc tcagacctca ctgggcggca agaggtctcc    1200
cggatcccag cctcacagac aagtgtgcca tttgaccatc tcgggaag               1248

<210> SEQ ID NO 11
<211> LENGTH: 549
<212> TYPE: PRT
<213> ORGANISM: Homo sapiens

<400> SEQUENCE: 11

Met Ser Pro Thr Ile Ser His Lys Asp Ser Ser Arg Gln Arg Arg Pro
1               5                   10                  15

Gly Asn Phe Ser His Ser Leu Asp Met Lys Ser Gly Pro Leu Pro Pro
            20                  25                  30
```

```
Gly Gly Trp Asp Asp Ser His Leu Asp Ser Ala Gly Arg Glu Gly Asp
            35                  40                  45

Arg Glu Ala Leu Leu Gly Asp Thr Gly Thr Gly Asp Phe Leu Lys Ala
 50                  55                  60

Pro Gln Ser Phe Arg Ala Glu Leu Ser Ser Ile Leu Leu Leu Leu Phe
 65                  70                  75                  80

Leu Tyr Val Leu Gln Gly Ile Pro Leu Gly Leu Ala Gly Ser Ile Pro
                85                  90                  95

Leu Ile Leu Gln Ser Lys Asn Val Ser Tyr Thr Asp Gln Ala Phe Phe
                100                 105                 110

Ser Phe Val Phe Trp Pro Phe Ser Leu Lys Leu Leu Trp Ala Pro Leu
                115                 120                 125

Val Asp Ala Val Tyr Val Lys Asn Phe Gly Arg Arg Lys Ser Trp Leu
130                 135                 140

Val Pro Thr Gln Tyr Ile Leu Gly Leu Phe Met Ile Tyr Leu Ser Thr
145                 150                 155                 160

Gln Val Asp Arg Leu Leu Gly Asn Thr Asp Asp Arg Thr Pro Asp Val
                165                 170                 175

Ile Ala Leu Thr Val Ala Phe Phe Leu Phe Glu Phe Leu Ala Ala Thr
                180                 185                 190

Gln Asp Ile Ala Val Asp Gly Trp Ala Leu Thr Met Leu Ser Arg Glu
                195                 200                 205

Asn Val Gly Tyr Ala Ser Thr Cys Asn Ser Val Gly Gln Thr Ala Gly
                210                 215                 220

Tyr Phe Leu Gly Asn Val Leu Phe Leu Ala Leu Glu Ser Ala Asp Phe
225                 230                 235                 240

Cys Asn Lys Tyr Leu Arg Phe Gln Pro Gln Pro Arg Gly Ile Val Thr
                245                 250                 255

Leu Ser Asp Phe Leu Phe Phe Trp Gly Thr Val Phe Leu Ile Thr Thr
                260                 265                 270

Thr Leu Val Ala Leu Leu Lys Lys Glu Asn Glu Val Ser Val Val Lys
            275                 280                 285

Glu Glu Thr Gln Gly Ile Thr Asp Thr Tyr Lys Leu Leu Phe Ala Ile
            290                 295                 300

Ile Lys Met Pro Ala Val Leu Thr Phe Cys Leu Leu Ile Leu Thr Ala
305                 310                 315                 320

Lys Ile Gly Phe Ser Ala Ala Asp Ala Val Thr Gly Leu Lys Leu Val
                325                 330                 335

Glu Glu Gly Val Pro Lys Glu His Leu Ala Leu Leu Ala Val Pro Met
                340                 345                 350

Val Pro Leu Gln Ile Ile Leu Pro Leu Ile Ser Lys Tyr Thr Ala
                355                 360                 365

Gly Pro Gln Pro Leu Asn Thr Phe Tyr Lys Ala Met Pro Tyr Arg Leu
370                 375                 380

Leu Leu Gly Leu Glu Tyr Ala Leu Leu Val Trp Trp Thr Pro Lys Val
385                 390                 395                 400

Glu His Gln Gly Gly Phe Pro Ile Tyr Tyr Ile Val Val Leu Leu
                405                 410                 415

Ser Tyr Ala Leu His Gln Val Thr Val Tyr Ser Met Tyr Val Ser Ile
                420                 425                 430

Met Ala Phe Asn Ala Lys Val Ser Asp Pro Leu Ile Gly Gly Thr Tyr
            435                 440                 445
```

```
Met Thr Leu Leu Asn Thr Val Ser Asn Leu Gly Gly Asn Trp Pro Ser
450                 455                 460
Thr Val Ala Leu Trp Leu Val Asp Pro Leu Thr Val Lys Glu Cys Val
465                 470                 475                 480
Gly Ala Ser Asn Gln Asn Cys Arg Thr Pro Asp Ala Val Glu Leu Cys
                485                 490                 495
Lys Lys Leu Gly Gly Ser Cys Val Thr Ala Leu Asp Gly Tyr Tyr Val
                500                 505                 510
Glu Ser Ile Ile Cys Val Phe Ile Gly Phe Gly Trp Trp Phe Phe Leu
                515                 520                 525
Gly Pro Lys Phe Lys Lys Leu Gln Asp Glu Gly Ser Ser Ser Trp Lys
530                 535                 540
Cys Lys Arg Asn Asn
545
```

<210> SEQ ID NO 12
<211> LENGTH: 1647
<212> TYPE: DNA
<213> ORGANISM: Homo sapiens

<400> SEQUENCE: 12

| | | | | | |
|---|---|---|---|---|---|
| atgtcaccca | ccatctccca | caaggacagc | agccggcaac | ggcggccagg | gaatttcagt | 60 |
| cactctctgg | atatgaagag | cggtcccctg | ccgccaggcg | gttgggatga | cagtcatttg | 120 |
| gactcagcgg | gccgggaagg | ggacagagaa | gctcttctgg | gggataccgg | cactggcgac | 180 |
| ttcttaaaag | ccccacagag | cttccgggcc | gaactaagca | gcattttgct | actactcttt | 240 |
| ctttacgtgc | ttcagggtat | tcccctgggc | ttggcgggaa | gcatcccact | catttttgcaa | 300 |
| agcaaaaatg | ttagctatac | agaccaagct | tccttcagtt | ttgtcttttg | gcccttcagt | 360 |
| ctcaaattac | tctgggcccc | gttggttgat | gcggtctacg | ttaagaactt | cggtcgtcgc | 420 |
| aaatcttggc | ttgtcccgac | acagtatata | ctaggactct | tcatgatcta | tttatccact | 480 |
| caggtggacc | gtttgcttgg | gaataccgat | gacagaacac | ccgacgtgat | tgctctcact | 540 |
| gtggcgttct | ttttgtttga | attcttggcc | gccactcagg | acattgccgt | cgatggttgg | 600 |
| gcgttaacta | tgttatccag | ggaaaatgtg | ggttatgctt | ctacttgcaa | ttcggtgggc | 660 |
| caaacagcgg | ttacttttt | gggcaatgtt | ttgttttttgg | cccttgaatc | tgccgacttt | 720 |
| tgtaacaaat | atttgcggtt | tcagcctcaa | cccagaggaa | tcgttactct | ttcagatttc | 780 |
| ctttttttct | ggggaactgt | attttttaata | acaacaacat | tggttgccct | tctgaaaaaa | 840 |
| gaaaacgaag | tatcagtagt | aaaagaagaa | acacaaggga | tcacagatac | ttacaagctg | 900 |
| ctttttgcaa | ttataaaaat | gccagcagtt | ctgacatttt | gccttctgat | tctaactgca | 960 |
| aagattggtt | tttcagcagc | agatgctgta | acaggactga | aattggtaga | agagggagta | 1020 |
| cccaaagaac | atttagcctt | attggcagtt | ccaatggttc | ctttgcagat | aatactgcct | 1080 |
| ctgattatca | gcaaatacac | tgcaggtccc | cagccattaa | acacatttta | caaagccatg | 1140 |
| ccctacagat | tattgcttgg | gttagaatat | gccctactgg | tttggtggac | tcctaaagta | 1200 |
| gaacatcaag | ggggattccc | tatatattac | tatatcgtag | tcctgctgag | ttatgcttta | 1260 |
| catcaggtta | cagtgtacag | catgtatgtt | tctataatgg | ctttcaatgc | aaaggttagt | 1320 |
| gatccactta | ttggaggaac | atacatgacc | cttttaaata | ccgtgtccaa | tctgggagga | 1380 |
| aactggcctt | ctacagtagc | tctttggctt | gtagatcccc | tcacagtaaa | agagtgtgta | 1440 |
| ggagcatcaa | accagaattg | tcgaacacct | gatgctgttg | agctttgcaa | aaaactgggt | 1500 |

```
ggctcatgtg ttacagccct ggatggttat tatgtggagt ccattatttg tgttttcatt    1560
ggatttggtt ggtggttctt tcttggtcca aaatttaaaa agttacagga tgaaggatca    1620
tcttcgtgga aatgcaaaag gaacaat                                        1647
```

<210> SEQ ID NO 13
<211> LENGTH: 470
<212> TYPE: PRT
<213> ORGANISM: Homo sapiens

<400> SEQUENCE: 13

```
Met Met Ala Ala Met Ala Thr Ala Arg Val Arg Met Gly Pro Arg Cys
1               5                   10                  15

Ala Gln Ala Leu Trp Arg Met Pro Trp Leu Pro Val Phe Leu Ser Leu
            20                  25                  30

Ala Ala Ala Ala Ala Ala Ala Ala Glu Gln Gln Val Pro Leu Val
        35                  40                  45

Leu Trp Ser Ser Asp Arg Asp Leu Trp Ala Pro Ala Ala Asp Thr His
    50                  55                  60

Glu Gly His Ile Thr Ser Asp Leu Gln Leu Ser Thr Tyr Leu Asp Pro
65                  70                  75                  80

Ala Leu Glu Leu Gly Pro Arg Asn Val Leu Phe Leu Gln Asp Lys
                85                  90                  95

Leu Ser Ile Glu Asp Phe Thr Ala Tyr Gly Gly Val Phe Gly Asn Lys
            100                 105                 110

Gln Asp Ser Ala Phe Ser Asn Leu Glu Asn Ala Leu Asp Leu Ala Pro
        115                 120                 125

Ser Ser Leu Val Leu Pro Ala Val Asp Trp Tyr Ala Val Ser Thr Leu
    130                 135                 140

Thr Thr Tyr Leu Gln Glu Lys Leu Gly Ala Ser Pro Leu His Val Asp
145                 150                 155                 160

Leu Ala Thr Leu Arg Glu Leu Lys Leu Asn Ala Ser Leu Pro Ala Leu
                165                 170                 175

Leu Leu Ile Arg Leu Pro Tyr Thr Ala Ser Ser Gly Leu Met Ala Pro
            180                 185                 190

Arg Glu Val Leu Thr Gly Asn Asp Glu Val Ile Gly Gln Val Leu Ser
        195                 200                 205

Thr Leu Lys Ser Glu Asp Val Pro Tyr Thr Ala Ala Leu Thr Ala Val
    210                 215                 220

Arg Pro Ser Arg Val Ala Arg Asp Val Ala Val Ala Gly Gly Leu
225                 230                 235                 240

Gly Arg Gln Leu Leu Gln Lys Gln Pro Val Ser Pro Val Ile His Pro
                245                 250                 255

Pro Val Ser Tyr Asn Asp Thr Ala Pro Arg Ile Leu Phe Trp Ala Gln
            260                 265                 270

Asn Phe Ser Val Ala Tyr Lys Asp Gln Trp Glu Asp Leu Thr Pro Leu
        275                 280                 285

Thr Phe Gly Val Gln Glu Leu Asn Leu Thr Gly Ser Phe Trp Asn Asp
    290                 295                 300

Ser Phe Ala Arg Leu Ser Leu Thr Tyr Glu Arg Leu Phe Gly Thr Thr
305                 310                 315                 320

Val Thr Phe Lys Phe Ile Leu Ala Asn Arg Leu Tyr Pro Val Ser Ala
                325                 330                 335

Arg His Trp Phe Thr Met Glu Arg Leu Glu Val His Ser Asn Gly Ser
            340                 345                 350
```

```
Val Ala Tyr Phe Asn Ala Ser Gln Val Thr Gly Pro Ser Ile Tyr Ser
        355                 360                 365

Phe His Cys Glu Tyr Val Ser Ser Leu Ser Lys Lys Gly Ser Leu Leu
    370                 375                 380

Val Ala Arg Thr Gln Pro Ser Pro Trp Gln Met Met Leu Gln Asp Phe
385                 390                 395                 400

Gln Ile Gln Ala Phe Asn Val Met Gly Glu Gln Phe Ser Tyr Ala Ser
                405                 410                 415

Asp Cys Ala Ser Phe Phe Ser Pro Gly Ile Trp Met Gly Leu Leu Thr
            420                 425                 430

Ser Leu Phe Met Leu Phe Ile Phe Thr Tyr Gly Leu His Met Ile Leu
        435                 440                 445

Ser Leu Lys Thr Met Asp Arg Phe Asp Asp His Lys Gly Pro Thr Ile
    450                 455                 460

Ser Leu Thr Gln Ile Val
465                 470

<210> SEQ ID NO 14
<211> LENGTH: 1410
<212> TYPE: DNA
<213> ORGANISM: Homo sapiens

<400> SEQUENCE: 14
atgatggcgg ccatggcgac ggctcgagtg cggatggggc cgcggtgcgc ccaggcgctc      60
tggcgcatgc cgtggctgcc ggtgttttg tcgttggcgg cggcggcggc ggcggcagcg     120
gcggagcagc aggtcccgct ggtgctgtgg tcgagtgacc gggacttgtg ggctcctgcg     180
gccgacactc atgaaggcca catcaccagc gacttgcagc tctctaccta cttagatccc     240
gccctggagc tgggtccag gaatgtgctg ctgttcctgc aggacaagct gagcattgag     300
gatttcacag catatggcgg tgtgtttgga aacaagcagg acagcgcctt ttctaaccta     360
gagaatgccc tggacctggc ccctcctca ctggtgcttc ctgccgtcga ctggtatgca     420
gtcagcactc tgaccactta cctgcaggag aagctcgggg ccagccctt gcatgtggac     480 ctggccaccc tgcgggagct gaagctcaat gccagcctcc tgctctgct gctcattcgc     540 ctgccctaca cagccagctc tggtctgatg caccagggg aagtcctcac aggcaacgat     600
gaggtcatcg gcaggtcct gagcacactc aagtccgaag atgtcccata cacagcggcc     660
ctcacagcgg tccgccttc cagggtggcc cgtgatgtag ccgtggtggc cggagggcta     720
ggtcgccagc tgctacaaaa acagccagta tcacctgtga tccatcctcc tgtgagttac     780
aatgacaccg ctccccggat cctgttctgg gcccaaaact tctctgtggc gtacaaggac     840
cagtgggagg acctgactcc cctcacctt ggggtgcagg aactcaacct gactggctcc     900
ttctggaatg actcctttgc caggctctca ctgacctatg aacgactctt tggtaccaca     960
gtgacattca gttcattct ggccaaccgc tctacccag tgtctgcccg gcactggttt    1020
accatggagc gcctcgaagt ccacagcaat ggctccgtcg cctacttcaa tgcttcccag    1080
gtcacagggc ccagcatcta ctccttccac tgcgagtatg tcagcagcct gagcaagaag    1140
ggtagtctcc tcgtggcccg cacgcagccc tctccctggc agatgatgct tcaggacttc    1200
cagatccagg ctttcaacgt aatggggag cagttctcct acgccagcga ctgtgccagc    1260
ttcttctccc ccggcatctg gatggggctg ctcacctccc tgttcatgct cttcatcttc    1320
acctatggcc tgcacatgat cctcagcctc aagaccatgg atcgctttga tgaccacaag    1380
```

```
ggccccacta tttctttgac ccagattgtg                                    1410
```

```
<210> SEQ ID NO 15
<211> LENGTH: 192
<212> TYPE: PRT
<213> ORGANISM: Homo sapiens

<400> SEQUENCE: 15
```

```
Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65              70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro His Thr Pro Ile Leu Leu
            100                 105                 110

Val Gly Thr Lys Leu Asp Leu Arg Asp Asp Lys Asp Thr Ile Glu Arg
        115                 120                 125

Leu Arg Asp Lys Lys Leu Ala Pro Ile Thr Tyr Pro Gln Gly Leu Ala
    130                 135                 140

Met Ala Arg Glu Ile Gly Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Pro Gly Lys Lys Cys Thr Val Phe
            180                 185                 190
```

```
<210> SEQ ID NO 16
<211> LENGTH: 576
<212> TYPE: DNA
<213> ORGANISM: Homo sapiens

<400> SEQUENCE: 16
atgcaggcca tcaagtgcgt ggtggtcggc gacggcgccg tggggaagac atgcttgctg    60
atcagctaca cgaccaacgc cttccccgga gagtacatcc ccaccgtttt tgacaactac   120
tctgccaacg tgatggtgga cgggaaacca gtcaacttgg ggctgtggga cacagcgggt   180
caggaggact acgatcggct gcggccactc tcctaccccc aaactgacgt ctttctgatc   240
tgcttctctc tggtgagccc ggcctccttc gagaatgttc gtgccaagtg gtacccggag   300
gtgcggcacc actgccccca cacgcccatc ctcctggtgg caccaagct ggacctccgc   360 gacgacaagg acaccattga gcggctgcgg gacaagaagc tggcacccat cacctaccca   420
cagggcctgg ccatggcccg ggagattggc tctgtgaaat acctggagtg ctcagccctg   480
acccagcggg gcctgaagac agtgtttgac gaggcgatcc gcgcggtgct ctgcccgccc   540
ccagtgaaga agccggggaa gaagtgcacc gtcttc                            576
```

```
<210> SEQ ID NO 17
<211> LENGTH: 247
<212> TYPE: PRT
<213> ORGANISM: Homo sapiens
```

<400> SEQUENCE: 17

| Met | Thr | Ile | Leu | Phe | Leu | Thr | Met | Val | Ile | Ser | Tyr | Phe | Gly | Cys | Met |
| 1 | | | | 5 | | | | | 10 | | | | | 15 | |

| Lys | Ala | Ala | Pro | Met | Lys | Glu | Ala | Asn | Ile | Arg | Gly | Gln | Gly | Gly | Leu |
| | | | 20 | | | | | 25 | | | | | 30 | | |

| Ala | Tyr | Pro | Gly | Val | Arg | Thr | His | Gly | Thr | Leu | Glu | Ser | Val | Asn | Gly |
| | | 35 | | | | | 40 | | | | | 45 | | | |

| Pro | Lys | Ala | Gly | Ser | Arg | Gly | Leu | Thr | Ser | Leu | Ala | Asp | Thr | Phe | Glu |
| | 50 | | | | | 55 | | | | | 60 | | | | |

| His | Met | Ile | Glu | Glu | Leu | Leu | Asp | Glu | Asp | Gln | Lys | Val | Arg | Pro | Asn |
| 65 | | | | | 70 | | | | | 75 | | | | | 80 |

| Glu | Glu | Asn | Asn | Lys | Asp | Ala | Asp | Leu | Tyr | Thr | Ser | Arg | Val | Met | Leu |
| | | | | 85 | | | | | 90 | | | | | 95 | |

| Ser | Ser | Gln | Val | Pro | Leu | Glu | Pro | Pro | Leu | Leu | Phe | Leu | Leu | Glu | Glu |
| | | | | 100 | | | | | 105 | | | | | 110 | |

| Tyr | Lys | Asn | Tyr | Leu | Asp | Ala | Ala | Asn | Met | Ser | Met | Arg | Val | Arg | Arg |
| | | | | 115 | | | | | 120 | | | | | 125 | |

| His | Ser | Asp | Pro | Ala | Arg | Arg | Gly | Glu | Leu | Ser | Val | Cys | Asp | Ser | Ile |
| | 130 | | | | | 135 | | | | | 140 | | | | |

| Ser | Glu | Trp | Val | Thr | Ala | Ala | Asp | Lys | Lys | Thr | Ala | Val | Asp | Met | Ser |
| 145 | | | | | 150 | | | | | 155 | | | | | 160 |

| Gly | Gly | Thr | Val | Thr | Val | Leu | Glu | Lys | Val | Pro | Val | Ser | Lys | Gly | Gln |
| | | | | 165 | | | | | 170 | | | | | 175 | |

| Leu | Lys | Gln | Tyr | Phe | Tyr | Glu | Thr | Lys | Cys | Asn | Pro | Met | Gly | Tyr | Thr |
| | | | | 180 | | | | | 185 | | | | | 190 | |

| Lys | Glu | Gly | Cys | Arg | Gly | Ile | Asp | Lys | Arg | His | Trp | Asn | Ser | Gln | Cys |
| | | | 195 | | | | | 200 | | | | | 205 | | |

| Arg | Thr | Thr | Gln | Ser | Tyr | Val | Arg | Ala | Leu | Thr | Met | Asp | Ser | Lys | Lys |
| | | 210 | | | | | 215 | | | | | 220 | | | |

| Arg | Ile | Gly | Trp | Arg | Phe | Ile | Arg | Ile | Asp | Thr | Ser | Cys | Val | Cys | Thr |
| 225 | | | | | 230 | | | | | 235 | | | | | 240 |

| Leu | Thr | Ile | Lys | Arg | Gly | Arg |
| | | | | 245 | | |

<210> SEQ ID NO 18
<211> LENGTH: 741
<212> TYPE: DNA
<213> ORGANISM: Homo sapiens

<400> SEQUENCE: 18

| atgaccatcc | ttttccttac | tatggttatt | tcatactttg | gttgcatgaa | ggctgccccc | 60 |
| atgaaagaag | caaacatccg | aggacaaggt | ggcttggcct | acccaggtgt | gcggacccat | 120 |
| gggactctgg | agagcgtgaa | tgggcccaag | gcaggttcaa | gaggcttgac | atcattggct | 180 |
| gacactttcg | aacacatgat | agaagagctg | ttggatgagg | accagaaagt | tcggcccaat | 240 |
| gaagaaaaca | ataaggacgc | agacttgtac | acgtccaggg | tgatgctcag | tagtcaagtg | 300 |
| cctttggagc | ctcctcttct | ctttctgctg | gaggaataca | aaaattacct | agacgctgca | 360 |
| aacatgtcca | tgagggtccg | cgccactct | gaccctgccc | gccaggggga | gctgagcgtg | 420 |
| tgtgacagta | ttagtgagtg | ggtaacggcg | gcagacaaaa | agactgcagt | ggacatgtcg | 480 |
| ggcgggacgg | tcacagtcct | tgaaaaggtc | cctgtatcaa | aaggccaact | gaagcaatac | 540 |
| ttctacgaga | ccaagtgcaa | tcccatgggt | tacacaaaag | aaggctgcag | ggcatagac | 600 |

```
aaaaggcatt ggaactccca gtgccgaact acccagtcgt acgtgcgggc ccttaccatg      660
gatagcaaaa agagaattgg ctggcgattc ataaggatag acacttcttg tgtatgtaca      720
ttgaccatta aagggggaag a                                                 741
```

<210> SEQ ID NO 19
<211> LENGTH: 181
<212> TYPE: PRT
<213> ORGANISM: Homo sapiens

<400> SEQUENCE: 19

```
Met Met Leu Gln His Pro Gly Gln Val Ser Ala Ser Glu Val Ser Ala
1               5                   10                  15

Ser Ala Ile Val Pro Cys Leu Ser Pro Pro Gly Ser Leu Val Phe Glu
                20                  25                  30

Asp Phe Ala Asn Leu Thr Pro Phe Val Lys Glu Glu Leu Arg Phe Ala
            35                  40                  45

Ile Gln Asn Lys His Leu Cys His Arg Met Ser Ser Ala Leu Glu Ser
        50                  55                  60

Val Thr Val Ser Asp Arg Pro Leu Gly Val Ser Ile Thr Lys Ala Glu
65                  70                  75                  80

Val Ala Pro Glu Glu Asp Glu Arg Lys Lys Arg Arg Glu Arg Asn
                85                  90                  95

Lys Ile Ala Ala Lys Cys Arg Asn Lys Lys Lys Glu Lys Thr Glu
                100                 105                 110

Cys Leu Gln Lys Glu Ser Glu Lys Leu Glu Ser Val Asn Ala Glu Leu
                115                 120                 125

Lys Ala Gln Ile Glu Glu Leu Lys Asn Glu Lys Gln His Leu Ile Tyr
        130                 135                 140

Met Leu Asn Leu His Arg Pro Thr Cys Ile Val Arg Ala Gln Asn Gly
145                 150                 155                 160

Arg Thr Pro Glu Asp Glu Arg Asn Leu Phe Ile Gln Gln Ile Lys Glu
                165                 170                 175

Gly Thr Leu Gln Ser
            180
```

<210> SEQ ID NO 20
<211> LENGTH: 543
<212> TYPE: DNA
<213> ORGANISM: Homo sapiens

<400> SEQUENCE: 20

```
atgatgcttc aacacccagg ccaggtctct gcctcggaag tgagtgcttc tgccatcgtc       60
ccctgcctgt cccctcctgg gtcactggtg tttgaggatt ttgctaacct gacgcccttt      120
gtcaaggaag agctgaggtt tgccatccag aacaagcacc tctgccaccg gatgtcctct      180
gcgctggaat cagtcactgt cagcgacaga cccctcgggg tgtccatcac aaaagccgag      240
gtagcccctg aagaagatga aggaaaaag aggcgacaga aagaaataa gattgcagct       300 gcaaagtgcc gaaacaagaa gaaggagaag acggagtgcc tgcagaaaga gtcggagaag      360
ctggaaagtg tgaatgctga actgaaggct cagattgagg agctcaagaa cgagaagcag      420
catttgatat acatgctcaa ccttcatcgg cccacgtgta ttgtccgggc tcagaatggg      480
aggactccag aagatgagag aaacctcttt atccaacaga taaaagaagg aacattgcag      540
agc                                                                     543
```

<210> SEQ ID NO 21
<211> LENGTH: 868
<212> TYPE: PRT
<213> ORGANISM: Homo sapiens

<400> SEQUENCE: 21

Met Ala Thr Phe Ile Ser Val Gln Leu Lys Lys Thr Ser Glu Val Asp
1               5                   10                  15

Leu Ala Lys Pro Leu Val Lys Phe Ile Gln Gln Thr Tyr Pro Ser Gly
            20                  25                  30

Gly Glu Glu Gln Ala Gln Tyr Cys Arg Ala Ala Glu Glu Leu Ser Lys
        35                  40                  45

Leu Arg Arg Ala Ala Val Gly Arg Pro Leu Asp Lys His Glu Gly Ala
50                  55                  60

Leu Glu Thr Leu Leu Arg Tyr Tyr Asp Gln Ile Cys Ser Ile Glu Pro
65                  70                  75                  80

Lys Phe Pro Phe Ser Glu Asn Gln Ile Cys Leu Thr Phe Thr Trp Lys
                85                  90                  95

Asp Ala Phe Asp Lys Gly Ser Leu Phe Gly Gly Ser Val Lys Leu Ala
            100                 105                 110

Leu Ala Ser Leu Gly Tyr Glu Lys Ser Cys Val Leu Phe Asn Cys Ala
        115                 120                 125

Ala Leu Ala Ser Gln Ile Ala Ala Glu Gln Asn Leu Asp Asn Asp Glu
130                 135                 140

Gly Leu Lys Ile Ala Ala Lys His Tyr Gln Phe Ala Ser Gly Ala Phe
145                 150                 155                 160

Leu His Ile Lys Glu Thr Val Leu Ser Ala Leu Ser Arg Glu Pro Thr
                165                 170                 175

Val Asp Ile Ser Pro Asp Thr Val Gly Thr Leu Ser Leu Ile Met Leu
            180                 185                 190

Ala Gln Ala Gln Glu Val Phe Phe Leu Lys Ala Thr Arg Asp Lys Met
        195                 200                 205

Lys Asp Ala Ile Ile Ala Lys Leu Ala Asn Gln Ala Ala Asp Tyr Phe
210                 215                 220

Gly Asp Ala Phe Lys Gln Cys Gln Tyr Lys Asp Thr Leu Pro Lys Glu
225                 230                 235                 240

Val Phe Pro Val Leu Ala Ala Lys His Cys Ile Met Gln Ala Asn Ala
                245                 250                 255

Glu Tyr His Gln Ser Ile Leu Ala Lys Gln Gln Lys Lys Phe Gly Glu
            260                 265                 270

Glu Ile Ala Arg Leu Gln His Ala Ala Glu Leu Ile Lys Thr Val Ala
        275                 280                 285

Ser Arg Tyr Asp Glu Tyr Val Asn Val Lys Asp Phe Ser Asp Lys Ile
290                 295                 300

Asn Arg Ala Leu Ala Ala Ala Lys Lys Asp Asn Asp Phe Ile Tyr His
305                 310                 315                 320

Asp Arg Val Pro Asp Leu Lys Asp Leu Asp Pro Ile Gly Lys Ala Thr
                325                 330                 335

Leu Val Lys Ser Thr Pro Val Asn Val Pro Ile Ser Gln Lys Phe Thr
            340                 345                 350

Asp Leu Phe Glu Lys Met Val Pro Val Ser Val Gln Gln Ser Leu Ala
        355                 360                 365

Ala Tyr Asn Gln Arg Lys Ala Asp Leu Val Asn Arg Ser Ile Ala Gln
370                 375                 380

```
Met Arg Glu Ala Thr Thr Leu Ala Asn Gly Val Leu Ala Ser Leu Asn
385                 390                 395                 400

Leu Pro Ala Ala Ile Glu Asp Val Ser Gly Asp Thr Val Pro Gln Ser
            405                 410                 415

Ile Leu Thr Lys Ser Arg Ser Val Ile Glu Gln Gly Gly Ile Gln Thr
            420                 425                 430

Val Asp Gln Leu Ile Lys Glu Leu Pro Glu Leu Leu Gln Arg Asn Arg
        435                 440                 445

Glu Ile Leu Asp Glu Ser Leu Arg Leu Leu Asp Glu Glu Ala Thr
        450                 455                 460

Asp Asn Asp Leu Arg Ala Lys Phe Lys Glu Arg Trp Gln Arg Thr Pro
465                 470                 475                 480

Ser Asn Glu Leu Tyr Lys Pro Leu Arg Ala Glu Gly Thr Asn Phe Arg
            485                 490                 495

Thr Val Leu Asp Lys Ala Val Gln Ala Asp Gly Gln Val Lys Glu Cys
                500                 505                 510

Tyr Gln Ser His Arg Asp Thr Ile Val Leu Leu Cys Lys Pro Glu Pro
            515                 520                 525

Glu Leu Asn Ala Ala Ile Pro Ser Ala Asn Pro Ala Lys Thr Met Gln
        530                 535                 540

Gly Ser Glu Val Val Asn Val Leu Lys Ser Leu Leu Ser Asn Leu Asp
545                 550                 555                 560

Glu Val Lys Lys Glu Arg Glu Gly Leu Glu Asn Asp Leu Lys Ser Val
                565                 570                 575

Asn Phe Asp Met Thr Ser Lys Phe Leu Thr Ala Leu Ala Gln Asp Gly
            580                 585                 590

Val Ile Asn Glu Glu Ala Leu Ser Val Thr Glu Leu Asp Arg Val Tyr
        595                 600                 605

Gly Gly Leu Thr Thr Lys Val Gln Glu Ser Leu Lys Lys Gln Glu Gly
610                 615                 620

Leu Leu Lys Asn Ile Gln Val Ser His Gln Glu Phe Ser Lys Met Lys
625                 630                 635                 640

Gln Ser Asn Asn Glu Ala Asn Leu Arg Glu Glu Val Leu Lys Asn Leu
            645                 650                 655

Ala Thr Ala Tyr Asp Asn Phe Val Glu Leu Val Ala Asn Leu Lys Glu
            660                 665                 670

Gly Thr Lys Phe Tyr Asn Glu Leu Thr Glu Ile Leu Val Arg Phe Gln
        675                 680                 685

Asn Lys Cys Ser Asp Ile Val Phe Ala Arg Lys Thr Glu Arg Asp Glu
690                 695                 700

Leu Leu Lys Asp Leu Gln Gln Ser Ile Ala Arg Glu Pro Ser Ala Pro
705                 710                 715                 720

Ser Ile Pro Thr Pro Ala Tyr Gln Ser Ser Pro Ala Gly Gly His Ala
            725                 730                 735

Pro Thr Pro Pro Thr Pro Ala Pro Arg Thr Met Pro Pro Thr Lys Pro
        740                 745                 750

Gln Pro Pro Ala Arg Pro Pro Pro Val Leu Pro Ala Asn Arg Ala
            755                 760                 765

Pro Ser Ala Thr Ala Pro Ser Pro Val Gly Ala Gly Thr Ala Ala Pro
        770                 775                 780

Ala Pro Ser Gln Thr Pro Gly Ser Ala Pro Pro Gln Ala Gln Gly
785                 790                 795                 800

Pro Pro Tyr Pro Thr Tyr Pro Gly Tyr Pro Gly Tyr Cys Gln Met Pro
```

|  | 805 |  |  | 810 |  |  | 815 |  |
|---|---|---|---|---|---|---|---|---|

Met Pro Met Gly Tyr Asn Pro Tyr Ala Tyr Gly Gln Tyr Asn Met Pro
            820                 825                 830

Tyr Pro Pro Val Tyr His Gln Ser Pro Gly Gln Ala Pro Tyr Pro Gly
        835                 840                 845

Pro Gln Gln Pro Ser Tyr Pro Phe Pro Gln Pro Gln Gln Ser Tyr
    850                 855                 860

Tyr Pro Gln Gln
865

<210> SEQ ID NO 22
<211> LENGTH: 2604
<212> TYPE: DNA
<213> ORGANISM: Homo sapiens

<400> SEQUENCE: 22

| atggcgacat | tcatctcggt | gcagctgaaa | aagacctcag | aggtggacct | ggccaagccg | 60 |
| ctggtgaagt | tcatccagca | gacttaccca | agcggcgggg | aagagcaggc | ccagtactgc | 120 |
| cgcgcggcgg | aggagctcag | caagctgcgc | cgcgccgcag | tcggtcgtcc | gctggacaag | 180 |
| cacgagggcg | cgctcgagac | gctcctgaga | tattatgatc | agatttgttc | tattgaaccc | 240 |
| aaattcccat | tttctgaaaa | tcagatctgc | ttgacattta | cctggaagga | tgctttcgat | 300 |
| aaaggttcac | ttttggagg | ctctgtaaaa | ctggctcttg | caagcttagg | atatgaaaag | 360 |
| agctgtgtgt | tgttcaattg | tgcagcctta | gctagccaaa | ttgcagcaga | cagaacctg | 420 |
| gataatgatg | aaggattgaa | atcgctgct | aaacattacc | agtttgctag | tggtgccttt | 480 |
| ttacatatta | agagacggt | tttatctgcc | ttaagtcgag | agccgaccgt | ggacatatct | 540 |
| ccagatactg | ttgggaccct | cagtcttatt | atgctggcac | aggctcaaga | agtatttttt | 600 |
| ttaaaagcca | aagagataa | aatgaaagat | gccatcatag | ctaaattggc | taatcaggct | 660 |
| gcagattatt | ttggtgatgc | tttcaaacag | tgtcaataca | agatactct | ccccaaggag | 720 |
| gtgttccctg | tcttggctgc | aaagcactgt | atcatgcagg | ccaatgctga | gtaccatcag | 780 |
| tctatcctgg | caaaacagca | gaagaaattt | ggagaagaaa | ttgcaaggtt | acagcatgca | 840 |
| gcagaactga | ttaaaacagt | ggcatctcgc | tatgatgaat | atgttaatgt | gaaggatttt | 900 |
| tctgacaaaa | tcaatcgtgc | ccttgctgca | gcaagaagg | ataatgactt | catttatcat | 960 |
| gatcgagttc | cagaccttaa | agatctagat | cctattggca | aagccacact | tgtgaaatct | 1020 |
| accccggtca | atgtacccat | cagtcagaaa | tttactgatc | tgtttgagaa | gatggttccc | 1080 |
| gtgtcagtac | agcagtcttt | ggctgcctat | aatcagagga | agccgatttt | ggttaacaga | 1140 |
| tcaattgctc | agatgagaga | agccaccact | ttggcaaatg | gggtgctagc | ttcccttaat | 1200 |
| cttccagcag | caattgaaga | tgtgtctgga | gacactgtac | ctcagtctat | attgactaaa | 1260 |
| tccagatctg | tgattgaaca | gggaggcatc | cagactgttg | atcagttgat | taaagaactg | 1320 |
| cctgaattac | tgcaacgaaa | tagagaaatc | ctagatgagt | cattaaggtt | gttggatgaa | 1380 |
| gaagaagcaa | ccgataatga | tttaagagca | aaatttaagg | aacgttggca | aaggacacca | 1440 |
| tccaatgaac | tgtataagcc | tttaagagca | gagggaacca | acttcagaac | agttttagat | 1500 |
| aaagctgtgc | aggcagatgg | acaagtgaaa | gaatgttacc | agtctcatcg | tgacaccatc | 1560 |
| gtgcttttgt | gtaagccaga | gcctgagctg | aatgctgcca | tcccttctgc | taatccagca | 1620 |
| aagaccatgc | agggcagtga | ggttgtaaat | gtccttaaaat | ccttattgtc | aaatcttgat | 1680 |
| gaagtaaaga | aggaaagaga | gggtctggag | aatgacttga | aatctgtgaa | ttttgacatg | 1740 |

```
acaagcaagt ttttgacagc cctggctcaa gatggtgtga taaatgaaga agctctttct    1800
gttactgaac tagatcgagt ctatggaggt cttacaacta aagtccaaga atctctaaag    1860
aaacaggagg gacttcttaa aaatattcag gtctcacatc aggaattttc aaaaatgaaa    1920
caatctaata atgaagctaa cttaagaaa gaagttttga agaatttagc tactgcatat     1980
gacaactttg ttgaacttgt agctaatttg aaggaaggca caaagttta caatgagttg     2040 actgaaatcc tggtcaggtt ccagaacaaa tgcagtgata tagttttgc acggaagaca     2100 gaaagagatg aactcttaaa ggacttgcaa caaagcattg ccagagaacc tagtgctcct    2160
tcaattccta cacctgcgta tcagtcctca ccagcaggag gacatgcacc aactcctcca    2220
actccagcgc caagaaccat gccgcctact aagccccagc ccccagccag gcctccacca    2280
cctgtgcttc cagcaaatcg agctccttct gctactgctc catctccagt gggggctggg    2340
actgctgcgc cagctccatc acaaacgcct ggctcagctc ctcctccaca ggcgcaggga    2400 ccacccctatc ccacctatcc aggatatcct gggtattgcc aaatgcccat gcccatgggc   2460
tataatcctt atgcgtatgg ccagtataat atgccatatc caccagtgta tcaccagagt    2520
cctggacagg ctccataccc gggaccccag cagccttcat accccttccc tcagccccca    2580
cagcagtctt actatccaca gcag                                           2604
```

<210> SEQ ID NO 23
<211> LENGTH: 215
<212> TYPE: PRT
<213> ORGANISM: Homo sapiens

<400> SEQUENCE: 23

```
Met Ala Ser Arg Gly Ala Thr Arg Pro Asn Gly Pro Asn Thr Gly Asn
1               5                   10                  15

Lys Ile Cys Gln Phe Lys Leu Val Leu Leu Gly Glu Ser Ala Val Gly
            20                  25                  30

Lys Ser Ser Leu Val Leu Arg Phe Val Lys Gly Gln Phe His Glu Phe
        35                  40                  45

Gln Glu Ser Thr Ile Gly Ala Ala Phe Leu Thr Gln Thr Val Cys Leu
    50                  55                  60

Asp Asp Thr Thr Val Lys Phe Glu Ile Trp Asp Thr Ala Gly Gln Glu
65                  70                  75                  80

Arg Tyr His Ser Leu Ala Pro Met Tyr Tyr Arg Gly Ala Gln Ala Ala
                85                  90                  95

Ile Val Val Tyr Asp Ile Thr Asn Glu Glu Ser Phe Ala Arg Ala Lys
            100                 105                 110

Asn Trp Val Lys Glu Leu Gln Arg Gln Ala Ser Pro Asn Ile Val Ile
        115                 120                 125

Ala Leu Ser Gly Asn Lys Ala Asp Leu Ala Asn Lys Arg Ala Val Asp
    130                 135                 140

Phe Gln Glu Ala Gln Ser Tyr Ala Asp Asp Asn Ser Leu Leu Phe Met
145                 150                 155                 160

Glu Thr Ser Ala Lys Thr Ser Met Asn Val Asn Glu Ile Phe Met Ala
                165                 170                 175

Ile Ala Lys Lys Leu Pro Lys Asn Glu Pro Gln Asn Pro Gly Ala Asn
            180                 185                 190

Ser Ala Arg Gly Arg Gly Val Asp Leu Thr Glu Pro Thr Gln Pro Thr
        195                 200                 205

Arg Asn Gln Cys Cys Ser Asn
```

<210> SEQ ID NO 24
<211> LENGTH: 645
<212> TYPE: DNA
<213> ORGANISM: Homo sapiens

<400> SEQUENCE: 24

```
atggctagtc gaggcgcaac aagacccaac gggccaaata ctggaaataa aatatgccag      60
ttcaaactag tacttctggg agagtccgct gttggcaaat caagcctagt gcttcgtttt     120
gtgaaaggcc aatttcatga atttcaagag agtaccattg gggctgcttt tctaacccaa     180
actgtatgtc ttgatgacac tacagtaaag tttgaaatat gggatacagc tggtcaagaa     240
cgataccata gcctagcacc aatgtactac agaggagcac aagcagccat agttgtatat     300
gatatcacaa atgaggagtc ctttgcaaga gcaaaaaatt gggttaaaga acttcagagg     360
caagcaagtc ctaacattgt aatagcttta tcgggaaaca aggccgacct agcaaataaa     420
agagcagtag atttccagga agcacagtcc tatgcagatg acaatagttt attattcatg     480
gagacatccg ctaaaacatc aatgaatgta aatgaaatat tcatggcaat agctaaaaaa     540
ttgccaaaga atgaaccaca aaatccagga gcaaattctg ccagaggaag aggagtagac     600
cttaccgaac ccacacaacc aaccaggaat cagtgttgta gtaac                     645
```

<210> SEQ ID NO 25
<211> LENGTH: 482
<212> TYPE: PRT
<213> ORGANISM: Homo sapiens

<400> SEQUENCE: 25

Met Ala Ala Val Arg Met Leu Arg Thr Trp Ser Arg Asn Ala Gly Lys
1               5                   10                  15

Leu Ile Cys Val Arg Tyr Phe Gln Thr Cys Gly Asn Val His Val Leu
            20                  25                  30

Lys Pro Asn Tyr Val Cys Phe Gly Tyr Pro Ser Phe Lys Tyr Ser
        35                  40                  45

His Pro His His Phe Leu Lys Thr Thr Ala Ala Leu Arg Gly Gln Val
    50                  55                  60

Val Gln Phe Lys Leu Ser Asp Ile Gly Glu Gly Ile Arg Glu Val Thr
65                  70                  75                  80

Val Lys Glu Trp Tyr Val Lys Glu Gly Asp Thr Val Ser Gln Phe Asp
                85                  90                  95

Ser Ile Cys Glu Val Gln Ser Asp Lys Ala Ser Val Thr Ile Thr Ser
            100                 105                 110

Arg Tyr Asp Gly Val Ile Lys Lys Leu Tyr Tyr Asn Leu Asp Asp Ile
        115                 120                 125

Ala Tyr Val Gly Lys Pro Leu Val Asp Ile Glu Thr Glu Ala Leu Lys
    130                 135                 140

Asp Ser Glu Glu Asp Val Val Glu Thr Pro Ala Val Ser His Asp Glu
145                 150                 155                 160

His Thr His Gln Glu Ile Lys Gly Arg Lys Thr Leu Ala Thr Pro Ala
                165                 170                 175

Val Arg Arg Leu Ala Met Glu Asn Asn Ile Lys Leu Ser Glu Val Val
            180                 185                 190

Gly Ser Gly Lys Asp Gly Arg Ile Leu Lys Glu Asp Ile Leu Asn Tyr
        195                 200                 205

Leu Glu Lys Gln Thr Gly Ala Ile Leu Pro Pro Ser Pro Lys Val Glu
    210                 215                 220

Ile Met Pro Pro Pro Lys Pro Lys Asp Met Thr Val Pro Ile Leu
225                 230                 235                 240

Val Ser Lys Pro Pro Val Phe Thr Gly Lys Asp Lys Thr Glu Pro Ile
                245                 250                 255

Lys Gly Phe Gln Lys Ala Met Val Lys Thr Met Ser Ala Ala Leu Lys
            260                 265                 270

Ile Pro His Phe Gly Tyr Cys Asp Glu Ile Asp Leu Thr Glu Leu Val
        275                 280                 285

Lys Leu Arg Glu Glu Leu Lys Pro Ile Ala Phe Ala Arg Gly Ile Lys
    290                 295                 300

Leu Ser Phe Met Pro Phe Phe Leu Lys Ala Ala Ser Leu Gly Leu Leu
305                 310                 315                 320

Gln Phe Pro Ile Leu Asn Ala Ser Val Asp Glu Asn Cys Gln Asn Ile
                325                 330                 335

Thr Tyr Lys Ala Ser His Asn Ile Gly Ile Ala Met Asp Thr Glu Gln
            340                 345                 350

Gly Leu Ile Val Pro Asn Val Lys Asn Val Gln Ile Cys Ser Ile Phe
        355                 360                 365

Asp Ile Ala Thr Glu Leu Asn Arg Leu Gln Lys Leu Gly Ser Val Gly
    370                 375                 380

Gln Leu Ser Thr Thr Asp Leu Thr Gly Gly Thr Phe Thr Leu Ser Asn
385                 390                 395                 400

Ile Gly Ser Ile Gly Gly Thr Phe Ala Lys Pro Val Ile Met Pro Pro
                405                 410                 415

Glu Val Ala Ile Gly Ala Leu Gly Ser Ile Lys Ala Ile Pro Arg Phe
            420                 425                 430

Asn Gln Lys Gly Glu Val Tyr Lys Ala Gln Ile Met Asn Val Ser Trp
        435                 440                 445

Ser Ala Asp His Arg Val Ile Asp Gly Ala Thr Met Ser Arg Phe Ser
    450                 455                 460

Asn Leu Trp Lys Ser Tyr Leu Glu Asn Pro Ala Phe Met Leu Leu Asp
465                 470                 475                 480

Leu Lys

<210> SEQ ID NO 26
<211> LENGTH: 1446
<212> TYPE: DNA
<213> ORGANISM: Homo sapiens

<400> SEQUENCE: 26
atggctgcag tccgtatgct gagaacctgg agcaggaatg cggggaagct gatttgtgtt    60
cgctattttc aaacatgtgg taatgttcat gttttgaagc caaattatgt gtgtttcttt   120
ggttatcctt cattcaagta tagtcatcca catcacttcc tgaaaacaac tgctgctctc   180
cgtggacagg ttgttcagtt caagctctca gacattggag aagggattag agaagtaact   240
gttaaagaat ggtatgtaaa agaaggagat acagtgtctc agtttgatag catctgtgaa   300
gttcaaagtg ataagcttc tgttaccatc actagtcgtt atgatggagt cattaaaaaa   360
ctctattata atctagacga tattgccat gtggggaagc cattagtaga catagaaacg   420
gaagctttaa agattcaga agaagatgtt gttgaaactc ctgcagtgtc tcatgatgaa   480
catacacacc aagagataaa gggccgaaaa acactggcaa ctcctgcagt tcgccgtctg   540

```
gcaatggaaa acaatattaa gctgagtgaa gttgttggct caggaaaaga tggcagaata    600
cttaaagaag atatcctcaa ctatttggaa aagcagacag gagctatatt gcctccttca    660
cccaaagttg aaattatgcc acctccacca aagccaaaag acatgactgt tcctatacta    720
gtatcaaaac ctccggtatt cacaggcaaa gacaaaacag aacccataaa aggctttcaa    780
aaagcaatgg tcaagactat gtctgcagcc ctgaagatac ctcattttgg ttattgtgat    840
gagattgacc ttactgaact ggttaagctc cgagaagaat taaaacccat tgcatttgct    900
cgtggaatta aactctcctt tatgcctttc ttcttaaagg ctgcttcctt gggattacta    960
cagtttccta tccttaacgc ttctgtggat gaaaactgcc agaatataac atataaggct    1020
tctcataaca ttgggatagc aatggatact gagcagggtt tgattgtccc taatgtgaaa    1080
aatgttcaga tctgctctat atttgacatc gccactgaac tgaaccgcct ccagaaattg    1140
ggctctgtgg gtcagctcag caccactgat cttacaggag aacatttac tctttccaac    1200 attggatcaa ttggtggtac ctttgccaaa ccagtgataa tgccacctga agtagccatt    1260
ggggcccttg gatcaattaa ggccattccc cgatttaacc agaaaggaga agtatataag    1320
gcacagataa tgaatgtgag ctggtcagct gatcacagag ttattgatgg tgctacaatg    1380
tcacgcttct ccaatttgtg gaaatcctat ttagaaaacc cagcttttat gctactagat    1440
ctgaaa                                                                1446
```

```
<210> SEQ ID NO 27
<211> LENGTH: 473
<212> TYPE: PRT
<213> ORGANISM: Homo sapiens

<400> SEQUENCE: 27

Met Ala Gln Leu Glu Gly Tyr Tyr Phe Ser Ala Leu Ser Cys Thr
1               5                   10                  15

Phe Leu Val Ser Cys Leu Leu Phe Ser Ala Phe Ser Arg Ala Leu Arg
                20                  25                  30

Glu Pro Tyr Met Asp Glu Ile Phe His Leu Pro Gln Ala Gln Arg Tyr
            35                  40                  45

Cys Glu Gly His Phe Ser Leu Ser Gln Trp Asp Pro Met Ile Thr Thr
        50                  55                  60

Leu Pro Gly Leu Tyr Leu Val Ser Ile Gly Val Ile Lys Pro Ala Ile
65                  70                  75                  80

Trp Ile Phe Gly Trp Ser Glu His Val Val Cys Ser Ile Gly Met Leu
                85                  90                  95

Arg Phe Val Asn Leu Leu Phe Ser Val Gly Asn Phe Tyr Leu Leu Tyr
                100                 105                 110

Leu Leu Phe Cys Lys Val Gln Pro Arg Asn Lys Ala Ala Ser Ser Ile
            115                 120                 125

Gln Arg Val Leu Ser Thr Leu Thr Leu Ala Val Phe Pro Thr Leu Tyr
        130                 135                 140

Phe Phe Asn Phe Leu Tyr Tyr Thr Glu Ala Gly Ser Met Phe Phe Thr
145                 150                 155                 160

Leu Phe Ala Tyr Leu Met Cys Leu Tyr Gly Asn His Lys Thr Ser Ala
                165                 170                 175

Phe Leu Gly Phe Cys Gly Phe Met Phe Arg Gln Thr Asn Ile Ile Trp
            180                 185                 190

Ala Val Phe Cys Ala Gly Asn Val Ile Ala Gln Lys Leu Thr Glu Ala
        195                 200                 205
```

Trp Lys Thr Glu Leu Gln Lys Glu Asp Arg Leu Pro Pro Ile Lys
            210                 215                 220
Gly Pro Phe Ala Glu Phe Arg Lys Ile Leu Gln Phe Leu Leu Ala Tyr
225                 230                 235                 240
Ser Met Ser Phe Lys Asn Leu Ser Met Leu Leu Leu Thr Trp Pro
                245                 250                 255
Tyr Ile Leu Leu Gly Phe Leu Phe Cys Ala Phe Val Val Asn Gly
            260                 265                 270
Gly Ile Val Ile Gly Asp Arg Ser His Glu Ala Cys Leu His Phe
            275                 280                 285
Pro Gln Leu Phe Tyr Phe Ser Phe Thr Leu Phe Phe Ser Phe Pro
290                 295                 300
His Leu Leu Ser Pro Ser Lys Ile Lys Thr Phe Leu Ser Leu Val Trp
305                 310                 315                 320
Lys Arg Arg Ile Leu Phe Phe Val Val Thr Leu Val Ser Val Phe Leu
                325                 330                 335
Val Trp Lys Phe Thr Tyr Ala His Lys Tyr Leu Leu Ala Asp Asn Arg
            340                 345                 350
His Tyr Thr Phe Tyr Val Trp Lys Arg Val Phe Gln Arg Tyr Glu Thr
            355                 360                 365
Val Lys Tyr Leu Leu Val Pro Ala Tyr Ile Phe Ala Gly Trp Ser Ile
370                 375                 380
Ala Asp Ser Leu Lys Ser Lys Ser Ile Phe Trp Asn Leu Met Phe Phe
385                 390                 395                 400
Ile Cys Leu Phe Thr Val Ile Val Pro Gln Lys Leu Leu Glu Phe Arg
                405                 410                 415
Tyr Phe Ile Leu Pro Tyr Val Ile Tyr Arg Leu Asn Ile Pro Leu Pro
            420                 425                 430
Pro Thr Ser Arg Leu Ile Cys Glu Leu Ser Cys Tyr Ala Val Val Asn
                435                 440                 445
Phe Ile Thr Phe Phe Ile Phe Leu Asn Lys Thr Phe Gln Trp Pro Asn
            450                 455                 460
Ser Gln Asp Ile Gln Arg Phe Met Trp
465                 470

<210> SEQ ID NO 28
<211> LENGTH: 1419
<212> TYPE: DNA
<213> ORGANISM: Homo sapiens

<400> SEQUENCE: 28
atggcgcagc tggaaggtta ctatttctcg gccgccttga gctgtacctt tttagtatcc      60
tgcctcctct tctccgcctt cagccgggcg ttgcgagagc cctacatgga cgagatcttc     120
cacctgcctc aggcgcagcg ctactgtgag gccatttct ccctttccca gtgggatccc      180
atgattacta cattacctgg cttgtacctg gtgtcaattg gagtgatcaa acctgccatt     240
tggatctttg atggtctga acatgttgtc tgctccattg ggatgctcag atttgttaat     300
cttctcttca gtgttggcaa cttctatttta ctatatttgc tttttctgcaa ggtacaaccc     360 agaaacaagg ctgcctcaag tatccagaga gtcttgtcaa cattaacact agcagtattt     420
ccaacacttt atttttttaa cttccttttat tatacagaag caggatctat gttttttact     480
ctttttgcgt atttgatgtg tctttatgga aatcataaaa cttcagcctt ccttggattt     540
tgtggcttca tgtttcggca aacaaatatc atctgggctg tcttctgtgc aggaaatgtc     600

```
attgcacaaa agttaacgga ggcttggaaa actgagctac aaaagaagga agacagactt    660
ccacctatta aaggaccatt tgcagaattc agaaaaattc ttcagtttct tttggcttat    720
tccatgtcct ttaaaaactt gagtatgctt ttgcttctga cttggcccta catccttctg    780
ggatttctgt tttgtgcttt tgtagtagtt aatggtggaa ttgttattgg cgatcggagt    840
agtcatgaag cctgtcttca ttttcctcaa ctattctact ttttttcatt tactctcttt    900
ttttcctttc ctcatctcct gtctcctagc aaaattaaga cttttctttc cttagtttgg    960
aaacgtagaa ttctgttttt tgtggttacc ttagtctctg tgttttagt ttggaaattc   1020
acttatgctc ataaatactt gctagcagac aatagacatt atactttcta tgtgtggaaa   1080
agagttttc aaagatatga aactgtaaaa tatttgttag ttccagccta tatatttgct   1140
ggttggagta tagctgactc attgaaatca aagtcaattt tttggaattt aatgtttttc   1200
atatgcttgt tcactgttat agttcctcag aaactgctgg aatttcgtta cttcatttta   1260
ccttatgtca tttataggct taacataccct ctgcctccca catccagact catttgtgaa   1320
ctgagctgct atgcagttgt taatttcata actttttca tctttctgaa caagactttt   1380
cagtggccaa atagtcagga cattcaaagg tttatgtgg                          1419
```

<210> SEQ ID NO 29
<211> LENGTH: 440
<212> TYPE: PRT
<213> ORGANISM: Homo sapiens

<400> SEQUENCE: 29

```
Met Gly Ser Ser His Leu Leu Asn Lys Gly Leu Pro Leu Gly Val Arg
1               5                   10                  15

Pro Pro Ile Met Asn Gly Pro Leu His Pro Arg Pro Leu Val Ala Leu
            20                  25                  30

Leu Asp Gly Arg Asp Cys Thr Val Glu Met Pro Ile Leu Lys Asp Val
        35                  40                  45

Ala Thr Val Ala Phe Cys Asp Ala Gln Ser Thr Gln Glu Ile His Glu
    50                  55                  60

Lys Val Leu Asn Glu Ala Val Gly Ala Leu Met Tyr His Thr Ile Thr
65                  70                  75                  80

Leu Thr Arg Glu Asp Leu Glu Lys Phe Lys Ala Leu Arg Ile Ile Val
                85                  90                  95

Arg Ile Gly Ser Gly Phe Asp Asn Ile Asp Ile Lys Ser Ala Gly Asp
            100                 105                 110

Leu Gly Ile Ala Val Cys Asn Val Pro Ala Ala Ser Val Glu Glu Thr
        115                 120                 125

Ala Asp Ser Thr Leu Cys His Ile Leu Asn Leu Tyr Arg Arg Ala Thr
    130                 135                 140

Trp Leu His Gln Ala Leu Arg Glu Gly Thr Arg Val Gln Ser Val Glu
145                 150                 155                 160

Gln Ile Arg Glu Val Ala Ser Gly Ala Ala Arg Ile Arg Gly Glu Thr
                165                 170                 175

Leu Gly Ile Ile Gly Leu Gly Arg Val Gly Gln Ala Val Ala Leu Arg
            180                 185                 190

Ala Lys Ala Phe Gly Phe Asn Val Leu Phe Tyr Asp Pro Tyr Leu Ser
        195                 200                 205

Asp Gly Val Glu Arg Ala Leu Gly Leu Gln Arg Val Ser Thr Leu Gln
    210                 215                 220

Asp Leu Leu Phe His Ser Asp Cys Val Thr Leu His Cys Gly Leu Asn
```

```
                225                 230                 235                 240
Glu His Asn His His Leu Ile Asn Asp Phe Thr Val Lys Gln Met Arg
                245                 250                 255
Gln Gly Ala Phe Leu Val Asn Thr Ala Arg Gly Gly Leu Val Asp Glu
            260                 265                 270
Lys Ala Leu Ala Gln Ala Leu Lys Glu Gly Arg Ile Arg Gly Ala Ala
            275                 280                 285
Leu Asp Val His Glu Ser Glu Pro Phe Ser Phe Ser Gln Gly Pro Leu
            290                 295                 300
Lys Asp Ala Pro Asn Leu Ile Cys Thr Pro His Ala Ala Trp Tyr Ser
305                 310                 315                 320
Glu Gln Ala Ser Ile Glu Met Arg Glu Glu Ala Ala Arg Glu Ile Arg
                325                 330                 335
Arg Ala Ile Thr Gly Arg Ile Pro Asp Ser Leu Lys Asn Cys Val Asn
            340                 345                 350
Lys Asp His Leu Thr Ala Ala Thr His Trp Ala Ser Met Asp Pro Ala
            355                 360                 365
Val Val His Pro Glu Leu Asn Gly Ala Ala Tyr Arg Tyr Pro Pro Gly
        370                 375                 380
Val Val Gly Val Ala Pro Thr Gly Ile Pro Ala Ala Val Glu Gly Ile
385                 390                 395                 400
Val Pro Ser Ala Met Ser Leu Ser His Gly Leu Pro Pro Val Ala His
                405                 410                 415
Pro Pro His Ala Pro Ser Pro Gly Gln Thr Val Lys Pro Glu Ala Asp
            420                 425                 430
Arg Asp His Ala Ser Asp Gln Leu
            435                 440

<210> SEQ ID NO 30
<211> LENGTH: 1320
<212> TYPE: DNA
<213> ORGANISM: Homo sapiens

<400> SEQUENCE: 30
atgggcagct cgcacttgct caacaagggc ctgccgcttg gcgtccgacc tccgatcatg      60
aacgggcccc tgcacccgcg gcccctggtg gcattgctgg atggccggga ctgcacagtg     120
gagatgccca tcctgaagga cgtggccact gtggccttct cgacgcgca gtccacgcag     180 gagatccatg agaaggtcct gaacgaggct gtggggcccc tgatgtacca ccatcact     240 ctcaccaggg aggacctgga gaagttcaaa gccctccgca tcatcgtccg gattggcagt     300
ggttttgaca catcgacat caagtcggcc ggggatttag cattgccgt ctgcaacgtg      360 cccgcggcgt ctgtggagga cggccgac tcgacgctgt ccacatcct gaacctgtac       420 cggcgggcca cctggctgca ccaggcgctg cgggagggca cgagtccga gcgtcgag       480 cagatccgcg aggtggcgtc cggcgctgcc aggatccgcg gggagacctt ggcatcatc      540 ggacttggtc gcgtggggca ggcagtggcg ctgcgggcca aggccttcgg cttcaacgtg     600
ctcttctacg accttactt gtcggatggc gtggagcggg cgctggggct gcagcgtgtc     660
agcaccctgc aggacctgct cttccacagc gactgcgtga ccctgcactg cggcctcaac     720
gagcacaacc accacctcat caacgacttc accgtcaagc agatgagaca gggggccttc     780
ctggtgaaca cagcccgggg tggcctggtg gatgagaagg cgctggccca ggccctgaag     840
gagggccgga tccgcggcgc ggccctggat gtgcacgagt cggaacccct tcagctttagc    900
```

-continued

```
cagggccctc tgaaggatgc acccaacctc atctgcaccc cccatgctgc atggtacagc    960
gagcaggcat ccatcgagat gcagaggag gcggcacggg agatccgcag agccatcaca   1020
ggccggatcc cagacagcct gaagaactgt gtcaacaagg accatctgac agccgccacc   1080
cactgggcca gcatggaccc cgccgtcgtg caccctgagc tcaatggggc tgcctatagg   1140
taccctccgg gcgtggtggg cgtggccccc actggcatcc cagctgctgt ggaaggtatc   1200
gtccccagcg ccatgtccct gtcccacggc ctgcccctg tggcccaccc gccccacgcc   1260
ccttctcctg gccaaaccgt caagcccgag gcggatagag accacgccag tgaccagttg   1320
```

<210> SEQ ID NO 31
<211> LENGTH: 317
<212> TYPE: PRT
<213> ORGANISM: Homo sapiens

<400> SEQUENCE: 31

```
Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300
```

Gly Thr Ala Ile Asn Gly Thr Leu Pro Leu Ser His Met
305                 310                 315

<210> SEQ ID NO 32
<211> LENGTH: 951
<212> TYPE: DNA
<213> ORGANISM: Homo sapiens

<400> SEQUENCE: 32

| | | | | | |
|---|---|---|---|---|---|
| atgtacaaca | tgatggagac | ggagctgaag | ccgccgggcc | cgcagcaaac | ttcgggggc | 60 |
| ggcggcggca | actccaccgc | ggcggcggcc | ggcggcaacc | agaaaaacag | cccggaccgc | 120 |
| gtcaagcggc | ccatgaatgc | cttcatggtg | tggtcccgcg | gcagcggcg | caagatggcc | 180 |
| caggagaacc | ccaagatgca | caactcggag | atcagcaagc | gcctgggcgc | cgagtggaaa | 240 |
| cttttgtcgg | agacggagaa | gcggccgttc | atcgacgagg | ctaagcggct | gcgagcgctg | 300 |
| cacatgaagg | agcacccgga | ttataaatac | cggccccggc | ggaaaaccaa | gacgctcatg | 360 |
| aagaaggata | gtacacgct | gcccggcggg | ctgctggccc | ccggcggcaa | tagcatggcg | 420 |
| agcggggtcg | gggtgggcgc | cggcctgggc | gcggcgtga | accagcgcat | ggacagttac | 480 |
| gcgcacatga | acggctggag | caacggcagc | tacagcatga | tgcaggacca | gctgggctac | 540 |
| ccgcagcacc | cgggcctcaa | tgcgcacggc | gcagcgcaga | tgcagcccat | gcaccgctac | 600 |
| gacgtgagcg | ccctgcagta | caactccatg | accagctcgc | agaccyacat | gaacggctcg | 660 |
| cccaccctaca | gcatgtccta | ctcgcagcag | ggcaccctg | gcatggctct | ggctccatg | 720 |
| ggttcggtgg | tcaagtccga | ggccagctcc | agccccctg | tggttacctc | ttcctcccac | 780 |
| tccagggcgc | cctgccaggc | cggggacctc | cgggacatga | tcagcatgta | tctccccggc | 840 |
| gccgaggtgc | cggaacccgc | cgcccccagc | agacttcaca | tgtcccagca | ctaccagagc | 900 |
| ggcccggtgc | ccggcacggc | cattaacggc | acactgcccc | tctcacacat | g | 951 |

<210> SEQ ID NO 33
<211> LENGTH: 264
<212> TYPE: PRT
<213> ORGANISM: Homo sapiens

<400> SEQUENCE: 33

Met Leu Ser His Asn Thr Met Met Lys Gln Arg Lys Gln Gln Ala Thr
1               5                   10                  15

Ala Ile Met Lys Glu Val His Gly Asn Asp Val Asp Gly Met Asp Leu
            20                  25                  30

Gly Lys Lys Val Ser Ile Pro Arg Asp Ile Met Leu Glu Glu Leu Ser
        35                  40                  45

His Leu Ser Asn Arg Gly Ala Arg Leu Phe Lys Met Arg Gln Arg Arg
    50                  55                  60

Ser Asp Lys Tyr Thr Phe Glu Asn Phe Gln Tyr Gln Ser Arg Ala Gln
65                  70                  75                  80

Ile Asn His Ser Ile Ala Met Gln Asn Gly Lys Val Asp Gly Ser Asn
                85                  90                  95

Leu Glu Gly Gly Ser Gln Gln Ala Pro Leu Thr Pro Asn Thr Pro
            100                 105                 110

Asp Pro Arg Ser Pro Asn Pro Asp Asn Ile Ala Pro Gly Tyr Ser
        115                 120                 125

Gly Pro Leu Lys Glu Ile Pro Pro Glu Lys Phe Asn Thr Thr Ala Val
    130                 135                 140

Pro Lys Tyr Tyr Gln Ser Pro Trp Glu Gln Ala Ile Ser Asn Asp Pro

```
                145                 150                 155                 160
Glu Leu Leu Glu Ala Leu Tyr Pro Lys Leu Phe Lys Pro Gly Lys
                    165                 170                 175

Ala Glu Leu Pro Asp Tyr Arg Ser Phe Asn Arg Val Ala Thr Pro Phe
                    180                 185                 190

Gly Gly Phe Glu Lys Ala Ser Arg Met Val Lys Phe Lys Val Pro Asp
                    195                 200                 205

Phe Glu Leu Leu Leu Thr Asp Pro Arg Phe Met Ser Phe Val Asn
        210                 215                 220

Pro Leu Ser Gly Arg Arg Ser Phe Asn Arg Thr Pro Lys Gly Trp Ile
225                 230                 235                 240

Ser Glu Asn Ile Pro Ile Val Ile Thr Thr Glu Pro Thr Asp Asp Thr
                    245                 250                 255

Thr Val Pro Glu Ser Glu Asp Leu
                260

<210> SEQ ID NO 34
<211> LENGTH: 792
<212> TYPE: DNA
<213> ORGANISM: Homo sapiens

<400> SEQUENCE: 34
atgctatcac ataatactat gatgaagcag agaaaacagc aagcaacagc catcatgaag      60
gaagtccatg gaaatgatgt tgatggcatg gacctgggca aaaaggtcag catccccaga     120
gacatcatgt tggaagaatt atcccatctc agtaaccgtg gtgccaggct atttaagatg     180
cgtcaaagaa gatctgacaa atacacattt gaaaatttcc agtatcaatc tagagcacaa     240
ataaatcaca gtattgctat gcagaatggg aaagtggatg gaagtaactt ggaaggtggt     300
tcgcagcaag cccccttgac tcctcccaac accccagatc cacgaagccc tccaaatcca     360
gacaacattg ctccaggata ttctggacca ctgaaggaaa ttcctcctga aaaattcaac     420
accacagctg tccctaagta ctatcaatct ccctgggaac aagccattag caatgatccg     480
gagcttttag aggctttata tcctaaactt ttcaagcctg aaggaaaggc agaactgcct     540
gattacagga gctttaacag ggttgccaca ccatttggag ttttgaaaa agcatcaaga     600 atggttaaat ttaaagttcc agattttgag ctactattgc taacagatcc caggtttatg     660
tcctttgtca atcccctttc tggcagacgg tcctttaata ggactcctaa gggatggata     720
tctgagaata ttcctatagt gataacaacc gaacctacag atgataccac tgtaccagaa     780
tcagaagacc ta                                                        792

<210> SEQ ID NO 35
<211> LENGTH: 83
<212> TYPE: PRT
<213> ORGANISM: Homo sapiens

<400> SEQUENCE: 35

Met Ser Phe Phe Gln Leu Leu Met Lys Arg Lys Glu Leu Ile Pro Leu
1               5                   10                  15

Val Val Phe Met Thr Val Ala Ala Gly Gly Ala Ser Ser Phe Ala Val
                20                  25                  30

Tyr Ser Leu Trp Lys Thr Asp Val Ile Leu Asp Arg Lys Lys Asn Pro
            35                  40                  45

Glu Pro Trp Glu Thr Val Asp Pro Thr Val Pro Gln Lys Leu Ile Thr
        50                  55                  60
```

```
Ile Asn Gln Gln Trp Lys Pro Ile Glu Glu Leu Gln Asn Val Gln Arg
 65                  70                  75                  80

Val Thr Lys
```

<210> SEQ ID NO 36
<211> LENGTH: 249
<212> TYPE: DNA
<213> ORGANISM: Homo sapiens

<400> SEQUENCE: 36

```
atgagctttt tccaactcct gatgaaaagg aaggaactca ttcccttggt ggtgttcatg     60
actgtggcgg cgggtggagc ctcatctttc gctgtgtatt ctctttggaa aaccgatgtg    120
atccttgatc gaaaaaaaaa tccagaacct tgggaaactg tggaccctac tgtacctcaa    180
aagcttataa caatcaacca acaatggaaa cccattgaag agttgcaaaa tgtccaaagg    240
gtgaccaaa                                                            249
```

<210> SEQ ID NO 37
<211> LENGTH: 653
<212> TYPE: PRT
<213> ORGANISM: Homo sapiens

<400> SEQUENCE: 37

```
Met Ala Ala Ala Ala Ser His Leu Asn Leu Asp Ala Leu Arg Glu
  1               5                  10                  15

Val Leu Glu Cys Pro Ile Cys Met Glu Ser Phe Thr Glu Glu Gln Leu
                 20                  25                  30

Arg Pro Lys Leu Leu His Cys Gly His Thr Ile Cys Arg Gln Cys Leu
             35                  40                  45

Glu Lys Leu Leu Ala Ser Ser Ile Asn Gly Val Arg Cys Pro Phe Cys
 50                  55                  60

Ser Lys Ile Thr Arg Ile Thr Ser Leu Thr Gln Leu Thr Asp Asn Leu
 65                  70                  75                  80

Thr Val Leu Lys Ile Ile Asp Thr Ala Gly Leu Ser Glu Ala Val Gly
                 85                  90                  95

Leu Leu Met Cys Arg Ser Cys Gly Arg Arg Leu Pro Arg Gln Phe Cys
            100                 105                 110

Arg Ser Cys Gly Leu Val Leu Cys Glu Pro Cys Arg Glu Ala Asp His
            115                 120                 125

Gln Pro Pro Gly His Cys Thr Leu Pro Val Lys Glu Ala Ala Glu Glu
130                 135                 140

Arg Arg Arg Asp Phe Gly Glu Lys Leu Thr Arg Leu Arg Glu Leu Met
145                 150                 155                 160

Gly Glu Leu Gln Arg Arg Lys Ala Ala Leu Glu Gly Val Ser Lys Asp
                165                 170                 175

Leu Gln Ala Arg Tyr Lys Ala Val Leu Gln Glu Tyr Gly His Glu Glu
            180                 185                 190

Arg Arg Val Gln Asp Glu Leu Ala Arg Ser Arg Lys Phe Phe Thr Gly
            195                 200                 205

Ser Leu Ala Glu Val Glu Lys Ser Asn Ser Gln Val Val Glu Glu Gln
        210                 215                 220

Ser Tyr Leu Leu Asn Ile Ala Glu Val Gln Ala Val Ser Arg Cys Asp
225                 230                 235                 240

Tyr Phe Leu Ala Lys Ile Lys Gln Ala Asp Val Ala Leu Leu Glu Glu
                245                 250                 255
```

-continued

Thr Ala Asp Glu Glu Pro Glu Leu Thr Ala Ser Leu Pro Arg Glu
            260                 265                 270

Leu Thr Leu Gln Asp Val Glu Leu Lys Val Gly His Val Gly Pro
        275                 280                 285

Leu Gln Ile Gly Gln Ala Val Lys Lys Pro Arg Thr Val Asn Val Glu
    290                 295                 300

Asp Ser Trp Ala Met Glu Ala Thr Ala Ser Ala Ala Ser Thr Ser Val
305                 310                 315                 320

Thr Phe Arg Glu Met Asp Met Ser Pro Glu Val Val Ala Ser Pro
            325                 330                 335

Arg Ala Ser Pro Ala Lys Gln Arg Gly Pro Glu Ala Ala Ser Asn Ile
            340                 345                 350

Gln Gln Cys Leu Phe Leu Lys Lys Met Gly Ala Lys Gly Ser Thr Pro
            355                 360                 365

Gly Met Phe Asn Leu Pro Val Ser Leu Tyr Val Thr Ser Gln Gly Glu
    370                 375                 380

Val Leu Val Ala Asp Arg Gly Asn Tyr Arg Ile Gln Val Phe Thr Arg
385                 390                 395                 400

Lys Gly Phe Leu Lys Glu Ile Arg Arg Ser Pro Ser Gly Ile Asp Ser
            405                 410                 415

Phe Val Leu Ser Phe Leu Gly Ala Asp Leu Pro Asn Leu Thr Pro Leu
            420                 425                 430

Ser Val Ala Met Asn Cys Gln Gly Leu Ile Gly Val Thr Asp Ser Tyr
            435                 440                 445

Asp Asn Ser Leu Lys Val Tyr Thr Leu Asp Gly His Cys Val Ala Cys
450                 455                 460

His Arg Ser Gln Leu Ser Lys Pro Trp Gly Ile Thr Ala Leu Pro Ser
465                 470                 475                 480

Gly Gln Phe Val Val Thr Asp Val Glu Gly Gly Lys Leu Trp Cys Phe
            485                 490                 495

Thr Val Asp Arg Gly Ser Gly Val Val Lys Tyr Ser Cys Leu Cys Ser
            500                 505                 510

Ala Val Arg Pro Lys Phe Val Thr Cys Asp Ala Glu Gly Thr Val Tyr
            515                 520                 525

Phe Thr Gln Gly Leu Gly Leu Asn Leu Glu Asn Arg Gln Asn Glu His
    530                 535                 540

His Leu Glu Gly Gly Phe Ser Ile Gly Ser Val Gly Pro Asp Gly Gln
545                 550                 555                 560

Leu Gly Arg Gln Ile Ser His Phe Phe Ser Glu Asn Glu Asp Phe Arg
            565                 570                 575

Cys Ile Ala Gly Met Cys Val Asp Ala Arg Gly Asp Leu Ile Val Ala
            580                 585                 590

Asp Ser Ser Arg Lys Glu Ile Leu His Phe Pro Lys Gly Gly Gly Tyr
    595                 600                 605

Ser Val Leu Ile Arg Glu Gly Leu Thr Cys Pro Val Gly Ile Ala Leu
    610                 615                 620

Thr Pro Lys Gly Gln Leu Leu Val Leu Asp Cys Trp Asp His Cys Ile
625                 630                 635                 640

Lys Ile Tyr Ser Tyr His Leu Arg Arg Tyr Ser Thr Pro
            645                 650

<210> SEQ ID NO 38
<211> LENGTH: 1959
<212> TYPE: DNA

<213> ORGANISM: Homo sapiens

<400> SEQUENCE: 38

```
atggctgcag cagcagcttc tcacctgaac ctggatgccc tccgggaagt gctagaatgc      60
cccatctgca tggagtcctt cacagaagag cagctgcgtc caagcttcct gcactgtggc     120
cataccatct gccgccagtg cctggagaag ctattggcca gtagcatcaa tggtgtccgc     180
tgtcccttt  gcagcaagat acccgcata accagcttga cccagctgac agacaatctg     240
acagtgctaa agatcattga tacagctggg ctcagcgagg ctgtgggct  gctcatgtgt     300
cggtcctgtg gcggcgtct  gccccggcaa ttctgccgga gctgtggttt ggtgttatgt     360
gagccctgcc gggaggcaga ccatcagcct cctggccact gtacactccc tgtcaaagaa     420
gcagctgagg agcggcgtcg ggactttgga gagaagttaa ctcgtctgcg gaacttatg      480
ggggagctgc agcggcggaa ggcagccttg aaggtgtct  ccaaggacct tcaggcaagg     540
tataaagcag ttctccagga gtatgggcat gaggagcgca gggtccagga tgagctggct     600
cgctctcgga agttcttcac aggctctttg gctgaagttg agaagtccaa tagtcaagtg     660
gtagaggagc agagttacct gcttaacatt gcagaggtgc aggctgtgtc tcgctgtgac     720
tacttcctgg ccaagatcaa gcaggcagat gtagcactac tggaggagac agctgatgag     780
gaggagccag agctcactgc cagcttgcct cgggagctca ccctgcaaga tgtggagctc     840
cttaaggtag tcatgttgg  ccccctccaa attggacaag ctgttaagaa gccccggaca     900
gttaacgtgg aagattcctg gccatggag  gccacagcgt ctgctgcctc tacctctgtt     960
acttttagag agatggacat gagcccggag gaagtggttg ccagccctag gcctcacct     1020
gctaaacagc ggggtcctga ggcagcctcc aatatccagc agtgcctctt tctcaagaag    1080
atgggggcca aaggcagcac tccaggaatg ttcaatcttc cagtcagtct ctacgtgacc    1140
agtcaaggtg aagtactagt cgctgaccgt ggtaactatc gtatacaagt ctttacccgc    1200
aaaggctttt tgaaggaaat ccgccgcagc cccagtggca ttgatagctt tgtgctaagc    1260
ttccttgggg cagatctacc caacctcact cctctctcag tggcaatgaa ctgccagggg    1320
ctgattggtg tgactgacag ctatgataac tccctcaagg tatataccct ggatggccac    1380
tgcgtggcct gtcacaggag ccagctgagc aaaccatggg gtatcacagc cttgccatct    1440
ggccagtttg tagtaaccga tgtggaaggt ggaaagcttt ggtgtttcac agttgatcga    1500
ggatcagggg tggtcaaata cagctgccta tgtagtgctg tgcggcccaa atttgtcacc    1560
tgtgatgctg agggcaccgt ctacttcacc cagggcttag gcctcaatct ggagaatcgg    1620
cagaatgagc accacctgga gggtggcttt tccattggct ctgtaggccc tgatgggcag    1680
ctgggtcgcc agattagcca cttcttctcg gagaatgagg atttccgctg cattgctggc    1740
atgtgtgtgg atgctcgtgg tgatctcatc gtggctgaca gtagtcgcaa ggaaattctc    1800
catttcccta agggtggggg ctatagtgtc cttattcgag agggacttac ctgtccggtg    1860
ggcatagccc taactcctaa ggggcagctg ctggtcttgg actgttggga tcattgcatc    1920
aagatctaca gctaccatct gagaagatat tccaccccca                          1959
```

<210> SEQ ID NO 39
<211> LENGTH: 445
<212> TYPE: PRT
<213> ORGANISM: Homo sapiens

<400> SEQUENCE: 39

Met Ala Glu Tyr Asp Leu Thr Thr Arg Ile Ala His Phe Leu Asp Arg

-continued

```
 1               5                   10                  15
His Leu Val Phe Pro Leu Leu Glu Phe Leu Ser Val Lys Glu Ile Tyr
             20                  25                  30

Asn Glu Lys Glu Leu Leu Gln Gly Lys Leu Asp Leu Leu Ser Asp Thr
             35                  40                  45

Asn Met Val Asp Phe Ala Met Asp Val Tyr Lys Asn Leu Tyr Ser Asp
             50                  55                  60

Asp Ile Pro His Ala Leu Arg Glu Lys Arg Thr Thr Val Val Ala Gln
 65              70                  75                  80

Leu Lys Gln Leu Gln Ala Glu Thr Glu Pro Ile Val Lys Met Phe Glu
             85                  90                  95

Asp Pro Glu Thr Thr Arg Gln Met Gln Ser Thr Arg Asp Gly Arg Met
             100                 105                 110

Leu Phe Asp Tyr Leu Ala Asp Lys His Gly Phe Arg Gln Glu Tyr Leu
             115                 120                 125

Asp Thr Leu Tyr Arg Tyr Ala Lys Phe Gln Tyr Glu Cys Gly Asn Tyr
             130                 135                 140

Ser Gly Ala Ala Glu Tyr Leu Tyr Phe Phe Arg Val Leu Val Pro Ala
145              150                 155                 160

Thr Asp Arg Asn Ala Leu Ser Ser Leu Trp Gly Lys Leu Ala Ser Glu
             165                 170                 175

Ile Leu Met Gln Asn Trp Asp Ala Ala Met Glu Asp Leu Thr Arg Leu
             180                 185                 190

Lys Glu Thr Ile Asp Asn Asn Ser Val Ser Ser Pro Leu Gln Ser Leu
             195                 200                 205

Gln Gln Arg Thr Trp Leu Ile His Trp Ser Leu Phe Val Phe Phe Asn
             210                 215                 220

His Pro Lys Gly Arg Asp Asn Ile Ile Asp Leu Phe Leu Tyr Gln Pro
225              230                 235                 240

Gln Tyr Leu Asn Ala Ile Gln Thr Met Cys Pro His Ile Leu Arg Tyr
             245                 250                 255

Leu Thr Thr Ala Val Ile Thr Asn Lys Asp Val Arg Lys Arg Arg Gln
             260                 265                 270

Val Leu Lys Asp Leu Val Lys Val Ile Gln Gln Glu Ser Tyr Thr Tyr
             275                 280                 285

Lys Asp Pro Ile Thr Glu Phe Val Glu Cys Leu Tyr Val Asn Phe Asp
             290                 295                 300

Phe Asp Gly Ala Gln Lys Lys Leu Arg Glu Cys Glu Ser Val Leu Val
305              310                 315                 320

Asn Asp Phe Phe Leu Val Ala Cys Leu Glu Asp Phe Ile Glu Asn Ala
             325                 330                 335

Arg Leu Phe Ile Phe Glu Thr Phe Cys Arg Ile His Gln Cys Ile Ser
             340                 345                 350

Ile Asn Met Leu Ala Asp Lys Leu Asn Met Thr Pro Glu Glu Ala Glu
             355                 360                 365

Arg Trp Ile Val Asn Leu Ile Arg Asn Ala Arg Leu Asp Ala Lys Ile
             370                 375                 380

Asp Ser Lys Leu Gly His Val Val Met Gly Asn Asn Ala Val Ser Pro
385              390                 395                 400

Tyr Gln Gln Val Ile Glu Lys Thr Lys Ser Leu Ser Phe Arg Ser Gln
             405                 410                 415

Met Leu Ala Met Asn Ile Glu Lys Lys Leu Asn Gln Asn Ser Arg Ser
             420                 425                 430
```

Glu Ala Pro Asn Trp Ala Thr Gln Asp Ser Gly Phe Tyr
        435                 440                 445

<210> SEQ ID NO 40
<211> LENGTH: 1335
<212> TYPE: DNA
<213> ORGANISM: Homo sapiens

<400> SEQUENCE: 40
atggcggagt acgacttgac tactcgcatc gcgcactttt tggatcggca tctagtcttt      60
ccgcttcttg aatttctctc tgtaaaggag atatataatg aaaaggaatt attacaaggt     120
aaattggacc ttcttagtga taccaacatg gtagactttg ctatggatgt atacaaaaac     180
ctttattctg atgatattcc tcatgctttg agagagaaaa gaaccacagt ggttgcacaa     240
ctgaaacagc ttcaggcaga aacagaacca attgtgaaga tgtttgaaga tccagaaact     300
acaaggcaaa tgcagtcaac cagggatggt aggatgctct tgactacct ggcggacaag      360
catggtttta ggcaggaata tttagataca ctctacagat atgcaaaatt ccagtacgaa     420
tgtgggaatt actcaggagc agcagaatat cttattttt ttagagtgct ggttccagca      480
acagataaa atgctttaag ttcactctgg ggaaagctgg cctctgaaat cttaatgcag      540
aattgggatg cagccatgga agaccttaca cggttaaaag agaccataga taataattct     600
gtgagttctc cacttcagtc tcttcagcag agaacatggc tcattcactg gtctctgttt     660
gttttcttca atcaccccaa aggtcgcgat aatattattg acctcttcct ttatcagcca     720
caatatctta tgcaattca gacaatgtgt ccacacattc ttcgctattt gactacagca      780
gtcataacaa caaggatgt tcgaaaacgt cggcaggttc taaaagatct agttaaagtt      840
attcaacagg agtcttacac atataaagac ccaattacag aatttgttga atgtttatat     900
gttaactttg actttgatgg ggctcagaaa aagctgaggg aatgtgaatc agtgcttgtg     960
aatgacttct tcttggtggc ttgtcttgag gatttcattg aaaatgcccg tctcttcata    1020
tttgagactt tctgtcgcat ccaccagtgt atcagcatta acatgttggc agataaattg    1080
aacatgactc cagaagaagc tgaaggtgg attgtaaatt tgattagaaa tgcaagactg     1140
gatgccaaga ttgattctaa attaggtcat gtggttatgg gtaacaatgc agtctcaccc    1200
tatcagcaag tgattgaaaa gaccaaaagc ctttccttta agagccagat gttggccatg    1260
aatattgaga gaaaacttaa tcagaatagc aggtcagagg ctcctaactg ggcaactcaa    1320
gattctggct ctac                                                     1335

<210> SEQ ID NO 41
<211> LENGTH: 156
<212> TYPE: PRT
<213> ORGANISM: Homo sapiens

<400> SEQUENCE: 41

Met Lys Glu Pro Leu Asp Gly Glu Cys Gly Lys Ala Val Val Pro Gln
1               5                   10                  15

Gln Glu Leu Leu Asp Lys Ile Lys Glu Glu Pro Asp Asn Ala Gln Glu
            20                  25                  30

Tyr Gly Cys Val Gln Gln Pro Lys Thr Gln Glu Ser Lys Leu Lys Ile
        35                  40                  45

Gly Gly Val Ser Ser Val Asn Glu Arg Pro Ile Ala Gln Gln Leu Asn
    50                  55                  60

Pro Gly Phe Gln Leu Ser Phe Ala Ser Ser Gly Pro Ser Val Leu Leu

```
                65                  70                  75                  80
Pro Ser Val Pro Ala Val Ala Ile Lys Val Phe Cys Ser Gly Cys Lys
                    85                  90                  95

Lys Met Leu Tyr Lys Gly Gln Thr Ala Tyr His Lys Thr Gly Ser Thr
                100                 105                 110

Gln Leu Phe Cys Ser Thr Arg Cys Ile Thr Arg His Ser Ser Pro Ala
                115                 120                 125

Cys Leu Pro Pro Pro Lys Lys Thr Cys Thr Asn Cys Ser Lys Tyr
                130                 135                 140

Lys Ile Leu Asn Ile Pro Phe Tyr Phe Thr Phe Phe
145                 150                 155

<210> SEQ ID NO 42
<211> LENGTH: 468
<212> TYPE: DNA
<213> ORGANISM: Homo sapiens

<400> SEQUENCE: 42
atgaaagaac ctttggatgg tgaatgtggc aaagcagtgg taccacagca ggagcttctg     60
gacaaaatta agaagaacc agacaatgct caagagtatg atgtgtcca acagccaaaa      120 actcaagaaa gtaaattgaa aattggtggt gtgtcttcag ttaatgagag acctattgcc     180
cagcagttga acccaggctt tcagctttct tttgcatcat ctggcccaag tgtgttgctt     240
ccttcagttc cagctgttgc tattaaggtt ttttgttctg gttgtaaaaa aatgctttat     300
aagggccaaa ctgcatatca taagacagga tctactcagc tcttctgctc cacacgatgc     360
atcaccagac attcttcacc tgcctgcctg ccacctcctc ccaagaaaac ctgcacaaac     420
tgctcgaagt ataaaattct taacatccct ttttacttta ccttttttt              468

<210> SEQ ID NO 43
<211> LENGTH: 155
<212> TYPE: PRT
<213> ORGANISM: Homo sapiens

<400> SEQUENCE: 43

Met Gln Pro Ser Pro Pro Thr Glu Leu Val Pro Ser Glu Arg Ala
1               5                   10                  15

Val Val Leu Leu Ser Cys Ala Leu Ser Ala Leu Gly Ser Gly Leu Leu
                    20                  25                  30

Val Ala Thr His Ala Leu Trp Pro Asp Leu Arg Ser Arg Ala Arg Arg
                    35                  40                  45

Leu Leu Leu Phe Leu Ser Leu Ala Asp Leu Leu Ser Ala Ala Ser Tyr
                    50                  55                  60

Phe Tyr Gly Val Leu Gln Asn Phe Ala Gly Pro Ser Trp Asp Cys Val
65                  70                  75                  80

Leu Gln Gly Ala Leu Ser Thr Phe Ala Asn Thr Ser Ser Phe Phe Trp
                    85                  90                  95

Thr Val Ala Ile Ala Leu Tyr Leu Tyr Leu Ser Ile Val Arg Ala Ala
                    100                 105                 110

Arg Gly Pro Arg Thr Asp Arg Leu Leu Trp Ala Phe His Val Val Arg
                    115                 120                 125

Trp Val Ala Val Ala Leu Leu Phe Gln Glu Pro Pro Thr Gln Ala Asp
                    130                 135                 140

Pro Ser Arg Ser Cys Pro Pro Arg Gly Arg Val
145                 150                 155
```

<210> SEQ ID NO 44
<211> LENGTH: 465
<212> TYPE: DNA
<213> ORGANISM: Homo sapiens

<400> SEQUENCE: 44

```
atgcagccgt ccccgccgcc caccgagctg gtgccgtcgg agcgcgccgt ggtgctgctg    60
tcgtgcgcac tctccgcgct cggctcgggc ctgctggtgg ccacgcacgc cctgtggccc   120
gacctgcgca gccgggcacg cgcctgctg ctcttcctgt cgctggccga cctgctctcg   180
gccgcctcct acttctacgg agtgctgcag aacttcgcgg cccgtcgtg ggactgcgtg   240
ctgcagggcg cgctgtccac cttcgccaac accagctcct tcttctggac cgtggccatt   300
gcgctctact tgtacctcag catcgtccgc gccgcgcgcg ggcctcgcac agatcgcctg   360
ctttgggcct tccatgtcgt caggtgggtg gcggtggcgc tgcttttcca ggagcccccg   420
acacaggccg acccctcccg gtcttgccct cccagaggcc gcgtc                  465
```

<210> SEQ ID NO 45
<211> LENGTH: 675
<212> TYPE: PRT
<213> ORGANISM: Homo sapiens

<400> SEQUENCE: 45

Met Asp Thr Lys Ser Ile Leu Glu Glu Leu Leu Leu Lys Arg Ser Gln
1               5                   10                  15

Gln Lys Lys Lys Met Ser Pro Asn Asn Tyr Lys Glu Arg Leu Phe Val
            20                  25                  30

Leu Thr Lys Thr Asn Leu Ser Tyr Tyr Glu Tyr Asp Lys Met Lys Arg
        35                  40                  45

Gly Ser Arg Lys Gly Ser Ile Glu Ile Lys Lys Ile Arg Cys Val Glu
    50                  55                  60

Lys Val Asn Leu Glu Glu Gln Thr Pro Val Glu Arg Gln Tyr Pro Phe
65                  70                  75                  80

Gln Ile Val Tyr Lys Asp Gly Leu Leu Tyr Val Tyr Ala Ser Asn Glu
                85                  90                  95

Glu Ser Arg Ser Gln Trp Leu Lys Ala Leu Gln Lys Glu Ile Arg Gly
            100                 105                 110

Asn Pro His Leu Leu Val Lys Tyr His Ser Gly Phe Phe Val Asp Gly
        115                 120                 125

Lys Phe Leu Cys Cys Gln Gln Ser Cys Lys Ala Ala Pro Gly Cys Thr
    130                 135                 140

Leu Trp Glu Ala Tyr Ala Asn Leu His Thr Ala Val Asn Glu Glu Lys
145                 150                 155                 160

His Arg Val Pro Thr Phe Pro Asp Arg Val Leu Lys Ile Pro Arg Ala
                165                 170                 175

Val Pro Val Leu Lys Met Asp Ala Pro Ser Ser Thr Thr Leu Ala
            180                 185                 190

Gln Tyr Asp Asn Glu Ser Lys Lys Asn Tyr Gly Ser Gln Pro Pro Ser
        195                 200                 205

Ser Ser Thr Ser Leu Ala Gln Tyr Asp Ser Asn Ser Lys Lys Ile Tyr
    210                 215                 220

Gly Ser Gln Pro Asn Phe Asn Met Gln Tyr Ile Pro Arg Glu Asp Phe
225                 230                 235                 240

Pro Asp Trp Trp Gln Val Arg Lys Leu Lys Ser Ser Ser Ser Ser Glu
                245                 250                 255

```
Asp Val Ala Ser Ser Asn Gln Lys Glu Arg Asn Val Asn His Thr Thr
            260                 265                 270

Ser Lys Ile Ser Trp Glu Phe Pro Glu Ser Ser Ser Glu Glu Glu
        275                 280                 285

Glu Asn Leu Asp Asp Tyr Asp Trp Phe Ala Gly Asn Ile Ser Arg Ser
            290                 295                 300

Gln Ser Glu Gln Leu Leu Arg Gln Lys Gly Lys Glu Gly Ala Phe Met
305                 310                 315                 320

Val Arg Asn Ser Ser Gln Val Gly Met Tyr Thr Val Ser Leu Phe Ser
                325                 330                 335

Lys Ala Val Asn Asp Lys Lys Gly Thr Val Lys His Tyr His Val His
            340                 345                 350

Thr Asn Ala Glu Asn Lys Leu Tyr Leu Ala Glu Asn Tyr Cys Phe Asp
            355                 360                 365

Ser Ile Pro Lys Leu Ile His Tyr His Gln His Asn Ser Ala Gly Met
        370                 375                 380

Ile Thr Arg Leu Arg His Pro Val Ser Thr Lys Ala Asn Lys Val Pro
385                 390                 395                 400

Asp Ser Val Ser Leu Gly Asn Gly Ile Trp Glu Leu Lys Arg Glu Glu
                405                 410                 415

Ile Thr Leu Leu Lys Glu Leu Gly Ser Gly Gln Phe Gly Val Val Gln
            420                 425                 430

Leu Gly Lys Trp Lys Gly Gln Tyr Asp Val Ala Val Lys Met Ile Lys
        435                 440                 445

Glu Gly Ser Met Ser Glu Asp Glu Phe Phe Gln Glu Ala Gln Thr Met
450                 455                 460

Met Lys Leu Ser His Pro Lys Leu Val Lys Phe Tyr Gly Val Cys Ser
465                 470                 475                 480

Lys Glu Tyr Pro Ile Tyr Ile Val Thr Glu Tyr Ile Ser Asn Gly Cys
                485                 490                 495

Leu Leu Asn Tyr Leu Arg Ser His Gly Lys Gly Leu Glu Pro Ser Gln
            500                 505                 510

Leu Leu Glu Met Cys Tyr Asp Val Cys Glu Gly Met Ala Phe Leu Glu
        515                 520                 525

Ser His Gln Phe Ile His Arg Asp Leu Ala Ala Arg Asn Cys Leu Val
530                 535                 540

Asp Arg Asp Leu Cys Val Lys Val Ser Asp Phe Gly Met Thr Arg Tyr
545                 550                 555                 560

Val Leu Asp Asp Gln Tyr Val Ser Ser Val Gly Thr Lys Phe Pro Val
                565                 570                 575

Lys Trp Ser Ala Pro Glu Val Phe His Tyr Phe Lys Tyr Ser Ser Lys
            580                 585                 590

Ser Asp Val Trp Ala Phe Gly Ile Leu Met Trp Glu Val Phe Ser Leu
        595                 600                 605

Gly Lys Gln Pro Tyr Asp Leu Tyr Asp Asn Ser Gln Val Val Leu Lys
        610                 615                 620

Val Ser Gln Gly His Arg Leu Tyr Arg Pro His Leu Ala Ser Asp Thr
625                 630                 635                 640

Ile Tyr Gln Ile Met Tyr Ser Cys Trp His Glu Leu Pro Glu Lys Arg
            645                 650                 655

Pro Thr Phe Gln Gln Leu Leu Ser Ser Ile Glu Pro Leu Arg Glu Lys
            660                 665                 670
```

Asp Lys His
      675

<210> SEQ ID NO 46
<211> LENGTH: 2025
<212> TYPE: DNA
<213> ORGANISM: Homo sapiens

<400> SEQUENCE: 46

| | | | | | |
|---|---|---|---|---|---|
| atggatacaa | aatctattct | agaagaactt | cttctcaaaa | gatcacagca | aaagaagaaa | 60 |
| atgtcaccaa | ataattacaa | agaacggctt | tttgttttga | ccaaaacaaa | cctttcctac | 120 |
| tatgaatatg | acaaaatgaa | aaggggcagc | agaaaaggat | ccattgaaat | taagaaaatc | 180 |
| agatgtgtgg | agaaagtaaa | tctcgaggag | cagacgcctg | tagagagaca | gtacccattt | 240 |
| cagattgtct | ataaagatgg | gcttctctat | gtctatgcat | caaatgaaga | gagccgaagt | 300 |
| cagtggttga | aagcattaca | aaaagagata | aggggtaacc | cccacctgct | ggtcaagtac | 360 |
| catagtgggt | tcttcgtgga | cgggaagttc | ctgtgttgcc | agcagagctg | taaagcagcc | 420 |
| ccaggatgta | ccctctggga | agcatatgct | aatctgcata | ctgcagtcaa | tgaagagaaa | 480 |
| cacagagttc | ccaccttccc | agacagagtg | ctgaagatac | ctcggcagt | tcctgttctc | 540 |
| aaaatggatg | caccatcttc | aagtaccact | ctagcccaat | atgacaacga | atcaaagaaa | 600 |
| aactatggct | cccagccacc | atcttcaagt | accagtctag | cgcaatatga | cagcaactca | 660 |
| aagaaaatct | atggctccca | gccaaacttc | aacatgcagt | atattccaag | ggaagacttc | 720 |
| cctgactggt | ggcaagtaag | aaaactgaaa | agtagcagca | gcagtgaaga | tgttgcaagc | 780 |
| agtaaccaaa | aagaaagaaa | tgtgaatcac | accaccctcaa | agatttcatg | ggaattccct | 840 |
| gagtcaagtt | catctgaaga | agaggaaaac | ctggatgatt | atgactggtt | tgctggtaac | 900 |
| atctccagat | cacaatctga | acagttactc | agacaaaagg | gaaagaagg | agcatttatg | 960 |
| gttagaaatt | cgagccaagt | gggaatgtac | acagtgtcct | tatttagtaa | ggctgtgaat | 1020 |
| gataaaaaag | gaactgtcaa | acattaccac | gtgcatacaa | atgctgagaa | caaattatac | 1080 |
| ctggcagaaa | actactgttt | tgattccatt | ccaaagctta | ttcattatca | tcaacacaat | 1140 |
| tcagcaggca | tgatcacacg | gctccgccac | cctgtgtcaa | caaaggccaa | caaggtcccc | 1200 |
| gactctgtgt | ccctgggaaa | tggaatctgg | gaactgaaaa | gagaagagat | taccttgttg | 1260 |
| aaggagctgg | gaagtggcca | gtttggagtg | gtccagctgg | gcaagtggaa | ggggcagtat | 1320 |
| gatgttgctg | ttaagatgat | caaggagggc | tccatgtcag | aagatgaatt | ctttcaggag | 1380 |
| gcccagacta | tgatgaaact | cagccatccc | aagctggtta | aattctatgg | agtgtgttca | 1440 |
| aaggaatacc | ccatatacat | agtgactgaa | tatataagca | atggctgctt | gctgaattac | 1500 |
| ctgaggagtc | acggaaaagg | acttgaacct | tcccagctct | tagaaatgtg | ctacgatgtc | 1560 |
| tgtgaaggca | tggccttctt | ggagagtcac | caattcatac | accgggactt | ggctgctcgt | 1620 |
| aactgcttgg | tggacagaga | tctctgtgtg | aaagtatctg | actttggaat | gacaaggtat | 1680 |
| gttcttgatg | atcagtatgt | cagttcagtc | ggaacaaagt | ttccagtcaa | gtggtcagct | 1740 |
| ccagaggtgt | ttcattactt | caaatacagc | agcaagtcag | acgtatgggc | atttggatc | 1800 |
| ctgatgtggg | aggtgttcag | cctggggaag | cagccctatg | acttgtatga | caactcccag | 1860 |
| gtggttctga | aggtctccca | gggccacagg | ctttaccggc | ccacctggc | atcggacacc | 1920 |
| atctaccaga | tcatgtacag | ctgctggcac | gagcttccag | aaaagcgtcc | cacatttcag | 1980 |
| caactcctgt | cttccattga | accacttcgg | gaaaaagaca | agcat | | 2025 |

<210> SEQ ID NO 47
<211> LENGTH: 502
<212> TYPE: PRT
<213> ORGANISM: Homo sapiens

<400> SEQUENCE: 47

Met Ala Ser Lys Lys Leu Gly Ala Asp Phe His Gly Thr Phe Ser Tyr
1               5                   10                  15

Leu Asp Asp Val Pro Phe Lys Thr Gly Asp Lys Phe Lys Thr Pro Ala
                20                  25                  30

Lys Val Gly Leu Pro Ile Gly Phe Ser Leu Pro Asp Cys Leu Gln Val
            35                  40                  45

Val Arg Glu Val Gln Tyr Asp Phe Ser Leu Glu Lys Lys Thr Ile Glu
        50                  55                  60

Trp Ala Glu Glu Ile Lys Lys Ile Glu Ala Glu Arg Glu Ala Glu
65                  70                  75                  80

Cys Lys Ile Ala Glu Ala Glu Ala Lys Val Asn Ser Lys Ser Gly Pro
                85                  90                  95

Glu Gly Asp Ser Lys Met Ser Phe Ser Lys Thr His Ser Thr Ala Thr
                100                 105                 110

Met Pro Pro Pro Ile Asn Pro Ile Leu Ala Ser Leu Gln His Asn Ser
                115                 120                 125

Ile Leu Thr Pro Thr Arg Val Ser Ser Ala Thr Lys Gln Lys Val
            130                 135                 140

Leu Ser Pro Pro His Ile Lys Ala Asp Phe Asn Leu Ala Asp Phe Glu
145                 150                 155                 160

Cys Glu Glu Asp Pro Phe Asp Asn Leu Glu Leu Lys Thr Ile Asp Glu
                165                 170                 175

Lys Glu Glu Leu Arg Asn Ile Leu Val Gly Thr Thr Gly Pro Ile Met
                180                 185                 190

Ala Gln Leu Leu Asp Asn Asn Leu Pro Arg Gly Gly Ser Gly Ser Val
                195                 200                 205

Leu Gln Asp Glu Glu Val Leu Ala Ser Leu Glu Arg Ala Thr Leu Asp
                210                 215                 220

Phe Lys Pro Leu His Lys Pro Asn Gly Phe Ile Thr Leu Pro Gln Leu
225                 230                 235                 240

Gly Asn Cys Glu Lys Met Ser Leu Ser Ser Lys Val Ser Leu Pro Pro
                245                 250                 255

Ile Pro Ala Val Ser Asn Ile Lys Ser Leu Ser Phe Pro Lys Leu Asp
                260                 265                 270

Ser Asp Asp Ser Asn Gln Lys Thr Ala Lys Leu Ala Ser Thr Phe His
                275                 280                 285

Ser Thr Ser Cys Leu Arg Asn Gly Thr Phe Gln Asn Ser Leu Lys Pro
                290                 295                 300

Ser Thr Gln Ser Ser Ala Ser Glu Leu Asn Gly His His Thr Leu Gly
305                 310                 315                 320

Leu Ser Ala Leu Asn Leu Asp Ser Gly Thr Glu Met Pro Ala Leu Thr
                325                 330                 335

Ser Ser Gln Met Pro Ser Leu Val Leu Ser Val Cys Thr Glu Glu
                340                 345                 350

Ser Ser Pro Pro Asn Thr Gly Pro Thr Val Thr Pro Asn Phe Ser
                355                 360                 365

Val Ser Gln Val Pro Asn Met Pro Ser Cys Pro Gln Ala Tyr Ser Glu
370                 375                 380

```
Leu Gln Met Leu Ser Pro Ser Glu Arg Gln Cys Val Glu Thr Val Val
385                 390                 395                 400

Asn Met Gly Tyr Ser Tyr Glu Cys Val Leu Arg Ala Met Lys Lys Lys
            405                 410                 415

Gly Glu Asn Ile Glu Gln Ile Leu Asp Tyr Leu Phe Ala His Gly Gln
        420                 425                 430

Leu Cys Glu Lys Gly Phe Asp Pro Leu Leu Val Glu Glu Ala Leu Glu
    435                 440                 445

Met His Gln Cys Ser Glu Glu Lys Met Met Glu Phe Leu Gln Leu Met
450                 455                 460

Ser Lys Phe Lys Glu Met Gly Phe Glu Leu Lys Asp Ile Lys Glu Val
465                 470                 475                 480

Leu Leu Leu His Asn Asn Asp Gln Asp Asn Ala Leu Glu Asp Leu Met
                485                 490                 495

Ala Arg Ala Gly Ala Ser
            500
```

<210> SEQ ID NO 48
<211> LENGTH: 1506
<212> TYPE: DNA
<213> ORGANISM: Homo sapiens

<400> SEQUENCE: 48

```
atggcttcta agaagttggg tgcagatttt catgggactt tcagttacct tgatgatgtc      60
ccatttaaga caggagacaa attcaaaaca ccagctaaag ttggtctacc tattggcttc     120
tccttgcctg attgtttgca ggttgtcaga gaagtacagt atgacttctc tttggaaaag     180
aaaaccattg agtgggctga agagattaag aaaatcgaag aagccgagcg ggaagcagag     240
tgcaaaattg cggaagcaga agctaaagtg aattctaaga gtggcccaga gggcgatagc     300
aaaatgagct ctccaagac tcacagtaca gccacaatgc cacctcctat taacccccatc     360
ctcgccagct gcagcacaa cagcatcctc acaccaactc gggtcagcag tagtgccacg     420
aaacagaaag ttctcagccc acctcacata aaggcggatt tcaatcttgc tgactttgag     480
tgtgaagaag acccatttga taatctggag ttaaaaacta ttgatgagaa ggaagagctg     540
agaaatattc tggtaggaac cactggaccc attatggctc agttattgga caataacttg     600
cccagggag gctctgggtc tgtgttacag gatgaggagg tcctggcatc cttggaacgg     660
gcaaccctag atttcaagcc tcttcataaa cccaatggct ttataacctt accacagttg     720
ggcaactgtg aaaagatgtc actgtcttcc aaagtgtccc tcccccctat acctgcagta     780
agcaatatca aatccctgtc tttccccaaa cttgactctg atgacagcaa tcagaagaca     840
gccaagctgg cgagcacttt ccatagcaca tcctgcctcc gcaatggcac gttccagaat     900
tccctaaagc cttccaccca aagcagtgcc agtgagctca tgggcatca cactcttggg     960
ctttcagctt tgaacttgga cagtggcaca gagatgccag ccctgacatc ctcccagatg    1020
ccttccctct ctgttttgtc tgtgtgcaca gaggaatcat cacctccaaa tactggtccc    1080
acggtcaccc ctcctaattt ctcagtgtca caagtgccca acatgcccag ctgtccccag    1140
gcctattctg aactgcagat gctgtccccc agcgagcggc agtgtgtgga cacggtggtc    1200
aacatgggct actcgtacga gtgtgtcctc agagccatga agaagaaagg agagaatatt    1260
gagcagattc tcgactatct ctttgcacat ggacagcttt gtgagaaggg cttcgaccct    1320
cttttagtgg aagaggctct ggaaatgcac cagtgttcag aagaaaagat gatggagttt    1380
```

```
cttcagttaa tgagcaaatt taaggagatg ggctttgagc tgaaagacat taaggaagtt    1440
ttgctattac acaacaatga ccaggacaat gctttggaag acctcatggc tcgggcagga    1500
gccagc                                                               1506
```

<210> SEQ ID NO 49
<211> LENGTH: 555
<212> TYPE: PRT
<213> ORGANISM: Homo sapiens

<400> SEQUENCE: 49

```
Met Arg Val Asn Gly Asp Asp Ser Val Ala Leu Ser Phe Leu
1               5                   10                  15

Tyr Asp Tyr Tyr Met Gly Pro Lys Glu Lys Arg Ile Leu Ser Ser Ser
                20                  25                  30

Thr Gly Gly Arg Asn Asp Gln Gly Lys Arg Tyr Tyr His Gly Met Glu
            35                  40                  45

Tyr Glu Thr Asp Leu Thr Pro Leu Glu Ser Pro Thr His Leu Met Lys
        50                  55                  60

Phe Leu Thr Glu Asn Val Ser Gly Thr Pro Glu Tyr Pro Asp Leu Leu
65                  70                  75                  80

Lys Lys Asn Asn Leu Met Ser Leu Glu Gly Ala Leu Pro Thr Pro Gly
                85                  90                  95

Lys Ala Ala Pro Leu Pro Ala Gly Pro Ser Lys Leu Glu Ala Gly Ser
            100                 105                 110

Val Asp Ser Tyr Leu Leu Pro Thr Thr Asp Met Tyr Asp Asn Gly Ser
        115                 120                 125

Leu Asn Ser Leu Phe Glu Ser Ile His Gly Val Pro Pro Thr Gln Arg
130                 135                 140

Trp Gln Pro Asp Ser Thr Phe Lys Asp Asp Pro Gln Glu Ser Met Leu
145                 150                 155                 160

Phe Pro Asp Ile Leu Lys Thr Ser Pro Glu Pro Pro Cys Pro Glu Asp
                165                 170                 175

Tyr Pro Ser Leu Lys Ser Asp Phe Glu Tyr Thr Leu Gly Ser Pro Lys
            180                 185                 190

Ala Ile His Ile Lys Ser Gly Glu Ser Pro Met Ala Tyr Leu Asn Lys
        195                 200                 205

Gly Gln Phe Tyr Pro Val Thr Leu Arg Thr Pro Ala Gly Gly Lys Gly
    210                 215                 220

Leu Ala Leu Ser Ser Asn Lys Val Lys Ser Val Val Met Val Val Phe
225                 230                 235                 240

Asp Asn Glu Lys Val Pro Val Glu Gln Leu Arg Phe Lys His Trp
                245                 250                 255

His Ser Arg Gln Pro Thr Ala Lys Gln Arg Val Ile Asp Val Ala Asp
            260                 265                 270

Cys Lys Glu Asn Phe Asn Thr Val Glu His Ile Glu Glu Val Ala Tyr
        275                 280                 285

Asn Ala Leu Ser Phe Val Trp Asn Val Asn Glu Glu Ala Lys Val Phe
    290                 295                 300

Ile Gly Val Asn Cys Leu Ser Thr Asp Phe Ser Ser Gln Lys Gly Val
305                 310                 315                 320

Lys Gly Val Pro Leu Asn Leu Gln Ile Asp Thr Tyr Asp Cys Gly Leu
                325                 330                 335

Gly Thr Glu Arg Leu Val His Arg Ala Val Cys Gln Ile Lys Ile Phe
            340                 345                 350
```

```
Cys Asp Lys Gly Ala Glu Arg Lys Met Arg Asp Asp Glu Arg Lys Gln
        355                 360                 365

Phe Arg Arg Lys Val Lys Cys Pro Asp Ser Ser Asn Ser Gly Val Lys
    370                 375                 380

Gly Cys Leu Leu Ser Gly Phe Arg Gly Asn Glu Thr Thr Tyr Leu Arg
385                 390                 395                 400

Pro Glu Thr Asp Leu Glu Thr Pro Pro Val Leu Phe Ile Pro Asn Val
                405                 410                 415

His Phe Ser Ser Leu Gln Arg Ser Gly Gly Ala Ala Pro Ser Ala Gly
            420                 425                 430

Pro Ser Ser Ser Asn Arg Leu Pro Leu Lys Arg Thr Cys Ser Pro Phe
        435                 440                 445

Thr Glu Glu Phe Glu Pro Leu Pro Ser Lys Gln Ala Lys Glu Gly Asp
    450                 455                 460

Leu Gln Arg Val Leu Leu Tyr Val Arg Arg Glu Thr Glu Val Phe
465                 470                 475                 480

Asp Ala Leu Met Leu Lys Thr Pro Asp Leu Lys Gly Leu Arg Asn Ala
                485                 490                 495

Ile Ser Glu Lys Tyr Gly Phe Pro Glu Glu Asn Ile Tyr Lys Val Tyr
            500                 505                 510

Lys Lys Cys Lys Arg Gly Ile Leu Val Asn Met Asp Asn Asn Ile Ile
        515                 520                 525

Gln His Tyr Ser Asn His Val Ala Phe Leu Leu Asp Met Gly Glu Leu
    530                 535                 540

Asp Gly Lys Ile Gln Ile Ile Leu Lys Glu Leu
545                 550                 555

<210> SEQ ID NO 50
<211> LENGTH: 1665
<212> TYPE: DNA
<213> ORGANISM: Homo sapiens

<400> SEQUENCE: 50
atgagagtca atggagatga tgacagtgtt gcggccttga gcttcctcta tgattactac     60
atgggtccca aggagaagcg atattgtcc tccagcactg ggggcaggaa tgaccaagga    120
aagaggtact accatggcat ggaatatgag acggacctca ctccccttga agccccaca    180 cacctcatga aattcctgac agagaacgtg tctggaaccc cagagtaccc agatttgctc    240
aagaagaata acctgatgag cttggagggg gccttgccca ccctggcaa ggcagctccc    300 ctccctgcag gccccagcaa gctggaggcc ggctctgtgg acagctacct gttacccacc    360
actgatatgt atgataatgg ctccctcaac tccttgtttg agagcattca tggggtgccg    420
cccacacagc gctggcagcc agacagcacc ttcaaagatg acccacagga gtcgatgctc    480
ttcccagata tcctgaaaac ctccccggaa ccccatgtc agaggacta ccccagcctc    540 aaaagtgact ttgaatacac cctgggctcc ccaaagcca tccacatcaa gtcaggcgag    600
tcacccatgg cctacctcaa caaaggccag ttctaccccg tcaccctgcg accccagca    660 ggtggcaaag ccttgcctt gtcctccaac aaagtcaaga gtgtggtgat ggttgtcttc    720
gacaatgaga aggtcccagt agagcagctg cgcttctgga agcactggca ttcccggcaa    780
cccactgcca agcagcgggt cattgacgtg gctgactgca agaaaaactt caacactgtg    840
gagcacattg aggaggtggc ctataatgca ctgtcctttg tgtggaacgt gaatgaagag    900
gccaaggtgt tcatcggcgt aaactgtctg agcacagact tttcctcaca aaagggggtg    960
```

-continued

```
aagggtgtcc ccctgaacct gcagattgac acctatgact gtggcttggg cactgagcgc    1020
ctggtacacc gtgctgtctg ccagatcaag atcttctgtg acaagggagc tgagaggaag    1080
atgcgcgatg acgagcggaa gcagttccgg aggaaggtca agtgccctga ctccagcaac    1140
agtggcgtca agggctgcct gctgtcgggc ttcaggggca atgagacgac ctaccttcgg    1200
ccagagactg acctggagac gccacccgtg ctgttcatcc ccaatgtgca cttctccagc    1260
ctgcagcgct ctggaggggc agcccccteg gcaggaccca gcagctccaa caggctgcct    1320
ctgaagcgta cctgctcgcc cttcactgag gagtttgagc ctctgccctc caagcaggcc    1380
aaggaaggcg accttcagag agttctgctg tatgtgcgga gggagactga ggaggtgttt    1440
gacgcgctca tgttgaagac cccagacctg aaggggctga ggaatgcgat ctctgagaag    1500
tatgggttcc ctgaagagaa catttacaaa gtctacaaga aatgcaagcg aggaatctta    1560
gtcaacatgg acaacaacat cattcagcat tacagcaacc acgtcgcctt cctgctggac    1620
atgggggagc tggacggcaa aattcagatc atccttaagg agctg                   1665
```

<210> SEQ ID NO 51
<211> LENGTH: 418
<212> TYPE: PRT
<213> ORGANISM: Homo sapiens

<400> SEQUENCE: 51

```
Met Arg Ser Leu Leu Leu Ser Ala Phe Cys Leu Leu Glu Ala Ala
1               5                   10                  15

Leu Ala Ala Glu Val Lys Lys Pro Ala Ala Ala Ala Pro Gly Thr
            20                  25                  30

Ala Glu Lys Leu Ser Pro Lys Ala Ala Thr Leu Ala Glu Arg Ser Ala
        35                  40                  45

Gly Leu Ala Phe Ser Leu Tyr Gln Ala Met Ala Lys Asp Gln Ala Val
    50                  55                  60

Glu Asn Ile Leu Val Ser Pro Val Val Ala Ser Ser Leu Gly Leu
65                  70                  75                  80

Val Ser Leu Gly Gly Lys Ala Thr Thr Ala Ser Gln Ala Lys Ala Val
                85                  90                  95

Leu Ser Ala Glu Gln Leu Arg Asp Glu Glu Val His Ala Gly Leu Gly
            100                 105                 110

Glu Leu Leu Arg Ser Leu Ser Asn Ser Thr Ala Arg Asn Val Thr Trp
        115                 120                 125

Lys Leu Gly Ser Arg Leu Tyr Gly Pro Ser Ser Val Ser Phe Ala Asp
    130                 135                 140

Asp Phe Val Arg Ser Ser Lys Gln His Tyr Asn Cys Glu His Ser Lys
145                 150                 155                 160

Ile Asn Phe Arg Asp Lys Arg Ser Ala Leu Gln Ser Ile Asn Glu Trp
                165                 170                 175

Ala Ala Gln Thr Thr Asp Gly Lys Leu Pro Glu Val Thr Lys Asp Val
            180                 185                 190

Glu Arg Thr Asp Gly Ala Leu Leu Val Asn Ala Met Phe Phe Lys Pro
        195                 200                 205

His Trp Asp Glu Lys Phe His His Lys Met Val Asp Asn Arg Gly Phe
    210                 215                 220

Met Val Thr Arg Ser Tyr Thr Val Gly Val Met Met His Arg Thr
225                 230                 235                 240

Gly Leu Tyr Asn Tyr Tyr Asp Asp Glu Lys Glu Lys Leu Gln Ile Val
```

```
                  245                 250                 255
Glu Met Pro Leu Ala His Lys Leu Ser Ser Leu Ile Ile Leu Met Pro
                260                 265                 270

His His Val Glu Pro Leu Glu Arg Leu Glu Lys Leu Leu Thr Lys Glu
            275                 280                 285

Gln Leu Lys Ile Trp Met Gly Lys Met Gln Lys Lys Ala Val Ala Ile
        290                 295                 300

Ser Leu Pro Lys Gly Val Val Glu Val Thr His Asp Leu Gln Lys His
305                 310                 315                 320

Leu Ala Gly Leu Gly Leu Thr Glu Ala Ile Asp Lys Asn Lys Ala Asp
                325                 330                 335

Leu Ser Arg Met Ser Gly Lys Lys Asp Leu Tyr Leu Ala Ser Val Phe
            340                 345                 350

His Ala Thr Ala Phe Glu Leu Asp Thr Asp Gly Asn Pro Phe Asp Gln
        355                 360                 365

Asp Ile Tyr Gly Arg Glu Glu Leu Arg Ser Pro Lys Leu Phe Tyr Ala
370                 375                 380

Asp His Pro Phe Ile Phe Leu Val Arg Asp Thr Gln Ser Gly Ser Leu
385                 390                 395                 400

Leu Phe Ile Gly Arg Leu Val Arg Pro Lys Gly Asp Lys Met Arg Asp
                405                 410                 415

Glu Leu

<210> SEQ ID NO 52
<211> LENGTH: 1254
<212> TYPE: DNA
<213> ORGANISM: Homo sapiens

<400> SEQUENCE: 52
atgcgctccc tcctgcttct cagcgccttc tgcctcctgg aggcggccct ggccgccgag      60
gtgaagaaac ctgcagccgc agcagctcct ggcactgcgg agaagttgag ccccaaggcg     120
gccacgcttg ccgagcgcag cgccggcctg ccttcagct tgtaccaggc catggccaag     180
gaccaggcag tggagaacat cctggtgtca cccgtggtgg tggcctcgtc gctggggctc     240
gtgtcgctgg gcggcaaggc gaccacggcg tcgcaggcca aggcagtgct gagcgccgag     300
cagctgcgcg acgaggaggt gcacgccggc ctgggcgagc tgctgcgctc actcagcaac     360
tccacggcgc gcaacgtgac ctggaagctg ggcagccgac tgtacggacc cagctcagtg     420
agcttcgctg atgacttcgt gcgcagcagc aagcagcact acaactgcga gcactccaag     480
atcaacttcc gcgacaagcg cagcgcgctg cagtccatca cgagtgggc cgcgcagacc     540 accgacggca gctgcccga ggtcaccaag gacgtggagc gcacggacgg cgccctgtta     600
gtcaacgcca tgttcttcaa gccacactgg gatgagaaat ccaccacaa gatggtggac     660 aaccgtggct tcatggtgac tcggtcctat accgtgggtg tcatgatgat gcaccggaca     720
ggcctctaca actactacga cgacgagaag gaaaagctgc aaatcgtgga gatgccctg     780 gcccacaagc tctccagcct catcatcctc atgccccatc acgtggagcc tctcgagcgc     840
cttgaaaagc tgctaaccaa agagcagctg aagatctgga tggggaagat gcagaagaag     900
gctgttgcca tctccttgcc caagggtgtg gtggaggtga cccatgacct gcagaaacac     960
ctggctgggc tgggcctgac tgaggccatt gacaagaaca aggccgactt gtcacgcatg    1020
tcaggcaaga aggacctgta cctggccagc gtgttccacg ccaccgcctt tgagttggac    1080
acagatggca accccttgga ccaggacatc tacgggcgcg aggagctgcg cagccccaag    1140
```

```
ctgttctacg ccgaccaccc cttcatcttc ctagtgcggg acacccaaag cggctccctg   1200
ctattcattg ggcgcctggt ccggcctaag ggtgacaaga tgcgagacga gtta          1254
```

<210> SEQ ID NO 53
<211> LENGTH: 636
<212> TYPE: PRT
<213> ORGANISM: Homo sapiens

<400> SEQUENCE: 53

```
Met Ser Pro His Pro Glu Ala Ile Thr Asp Cys Val Thr Leu Asn Thr
1               5                   10                  15

Val Gly Gln Leu Ala Glu Gly Gly Tyr Pro Leu Arg Phe Ser Thr Leu
            20                  25                  30

Phe Gln Glu Gln Gln Lys Met Asn Ile Ser Gln Ala Ser Val Ser Phe
        35                  40                  45

Lys Asp Val Thr Ile Glu Phe Thr Gln Glu Glu Trp Gln Gln Met Ala
    50                  55                  60

Pro Val Gln Lys Asn Leu Tyr Arg Asp Val Met Leu Glu Asn Tyr Ser
65                  70                  75                  80

Asn Leu Val Ser Val Gly Tyr Cys Cys Phe Lys Pro Glu Val Ile Phe
                85                  90                  95

Lys Leu Glu Gln Gly Glu Glu Pro Trp Phe Ser Glu Glu Phe Ser
            100                 105                 110

Asn Gln Ser His Pro Lys Asp Tyr Arg Gly Asp Asp Leu Ile Lys Gln
        115                 120                 125

Asn Lys Lys Ile Lys Asp Lys His Leu Glu Gln Ala Ile Cys Ile Asn
    130                 135                 140

Asn Lys Thr Leu Thr Thr Glu Glu Lys Val Leu Gly Lys Pro Phe
145                 150                 155                 160

Thr Leu His Val Ala Ala Val Ala Ser Thr Lys Met Ser Cys Lys Cys
                165                 170                 175

Asn Ser Trp Glu Val Asn Leu Gln Ser Ile Ser Glu Phe Ile Ile Asn
            180                 185                 190

Asn Arg Asn Tyr Ser Thr Lys Lys Ile Gly Cys Gly Asn Val Cys Glu
        195                 200                 205

Asn Ser Pro Phe Lys Ile Asn Phe Glu Lys Thr Gln Thr Gly Glu Lys
    210                 215                 220

Phe Tyr Glu His Asn Lys Asn Met Lys Ala Leu Asn Tyr Asn Glu Asn
225                 230                 235                 240

Leu Pro Lys His Pro Lys Phe Gln Thr Leu Glu Gln Ala Phe Glu Cys
                245                 250                 255

Asn Lys Ile Gly Lys Ala Phe Asn Asp Lys Ala Asn Cys Val Lys His
            260                 265                 270

Asn Ser Ser His Thr Gly Glu Thr Ser Ser Lys Asp Asp Glu Phe Arg
        275                 280                 285

Lys Asn Cys Asp Lys Lys Thr Leu Phe Asp His Arg Arg Thr Gly Thr
    290                 295                 300

Gly Lys Lys His Leu His Leu Asn Gln Cys Gly Lys Ser Phe Glu Lys
305                 310                 315                 320

Ser Thr Val Glu Glu Tyr Asn Lys Leu Asn Met Gly Ile Lys His Tyr
                325                 330                 335

Glu Leu Asn Pro Ser Gly Asn Asn Phe Asn Arg Lys Ala His Leu Thr
            340                 345                 350
```

```
Asp Pro Gln Thr Ala Val Ile Glu Glu Asn Pro Leu Val Ser Asn Asp
            355                 360                 365

Arg Thr Gln Thr Trp Val Lys Ser Ser Glu Tyr His Glu Asn Lys Lys
    370                 375                 380

Ser Tyr Gln Thr Ser Val His Arg Val Arg Arg Ser His Ser Met
385                 390                 395                 400

Met Lys Pro Tyr Lys Cys Asn Glu Cys Gly Lys Ser Phe Cys Gln Lys
                405                 410                 415

Gly His Leu Ile Gln His Gln Arg Thr His Thr Gly Lys Pro Phe
            420                 425                 430

Glu Cys Ser Glu Cys Gly Lys Thr Phe Ser Gln Lys Ser His Leu Ser
        435                 440                 445

Thr His Gln Arg Ile His Thr Ala Glu Lys Pro Tyr Lys Cys Asn Glu
    450                 455                 460

Cys Gly Lys Thr Phe Val Gln Lys Ser Thr Leu Arg Gly His Gln Arg
465                 470                 475                 480

Ile His Thr Gly Glu Lys Pro Tyr Glu Cys Ser Glu Cys Gly Lys Thr
                485                 490                 495

Phe Val Gln Lys Ser Thr Leu Arg Asp His His Arg Ile His Thr Gly
            500                 505                 510

Glu Lys Ser Phe Gln Cys Asn Gln Cys Gly Lys Thr Phe Gly Gln Lys
        515                 520                 525

Ser Asn Leu Arg Ile His Gln Arg Thr His Thr Gly Glu Lys Thr Tyr
    530                 535                 540

Gln Cys Asn Glu Cys Glu Lys Ser Phe Trp Arg Lys Asp His Leu Ile
545                 550                 555                 560

Gln His Gln Lys Thr His Thr Gly Glu Lys Pro Phe Lys Cys Asn Glu
                565                 570                 575

Cys Gly Lys Thr Phe Ala Arg Thr Ser Thr Leu Arg Val His Gln Arg
            580                 585                 590

Ile His Thr Gly Glu Lys Pro Phe Lys Cys Asn Glu Cys Gly Lys Lys
        595                 600                 605

Phe Val Arg Lys Ala Ile Leu Ser Asp His Gln Arg Ile His Thr Gly
    610                 615                 620

Glu Lys Pro Phe Gln Cys Asn Lys Cys Gly Lys Thr
625                 630                 635

<210> SEQ ID NO 54
<211> LENGTH: 1908
<212> TYPE: DNA
<213> ORGANISM: Homo sapiens

<400> SEQUENCE: 54
atgtcgccac atccagaagc catcacagat tgtgtgacac tgaacactgt gggccaactt      60
gcagaaggtg ttatccttt acggttctcc acactctttc aggagcagca gaaaatgaac     120
atatctcagg catcagtgtc attcaaggac gtgactatag aattcacccca ggaggagtgg    180 cagcaaatgg ccctgttca agaatctg tacagagatg tgatgctgga aactacagc         240 aacctcgtct cagtgggta ctgctgtttc aaaccagagg tgatcttcaa gttggagcaa      300
ggagaggagc cttggttctc agaggaggaa ttctcaaacc agagtcaccc aaaagattac     360
agaggtgatg acctgatcaa gcagaacaag aaaatcaaag acaaacactt ggagcaagca     420
atatgtatca ataataaaac attgactaca gaggaagaga agttttggg gaaaccatttt    480 actctgcatg tagctgctgt tgcttcaaca aaaatgtcct gcaaatgcaa ctcatgggaa     540
```

```
gtgaatttgc aaagtatttc tgaatttatc attaataata gaaactattc aacaaagaaa    600
ataggttgcg gtaatgtatg tgagaattca cctttcaaaa ttaactttga gaaaactcag    660
actggagaga aattttatga acataataaa aacatgaaag ctctcaatta taatgaaaat    720
cttcccaagc atccaaagtt tcaaactttg gagcaagctt ttgaatgtaa taaaattgga    780
aaagccttta atgataaggc taactgtgtt aaacataaca gttctcacac aggagaaaca    840
tcctctaaag atgatgaatt taggaaaaat tgtgataaga aaactctctt tgaccacagg    900
agaactggca cagggaagaa acacctgcat cttaatcaat gtgggaaatc ctttgagaag    960
tcaactgtgg aggaatataa taaacttaat atgggtataa aacattatga attaaatcca   1020
agtggaaata atttcaacag aaaggcacac ctcactgatc ctcaaacagc tgtcatagaa   1080
gagaacccat tggtaagtaa tgacagaaca cagacttggg ttaaatcctc tgaatatcat   1140
gaaaataaga aatcctacca gacgtcggtt cacagagttc gccgaagaag tcactcaatg   1200
atgaaaccct ataaatgtaa tgaatgtggg aaatccttct gtcagaaagg acatctcatt   1260
caacatcaga gaactcacac aggagagaaa ccatttgaat gtagtgaatg tggaaaaact   1320
ttctcccaga gtcacacct cagtactcat cagagaattc atacagcaga aaaaccctat   1380
aaatgtaatg aatgtggaaa acatttgtc cagaagtcaa ccctcagggg acatcaaaga   1440
attcacacag gagaaaaacc ctatgaatgt agtgaatgtg ggaaaacttt tgttcagaag   1500
tccaccctca gagatcatca cagaattcac acagggagaga atcctttca atgcaatcaa   1560
tgtggaaaaa catttggcca gaagtcaaac ctcagaatac atcagagaac tcacactggg   1620
gagaaaactt accagtgtaa tgaatgtgaa aaatccttct ggcgaaaaga tcatctcatt   1680
caacatcaga aaactcacac gggagagaaa ccattcaaat gtaacgaatg tgggaaaact   1740
tttgcccgga catcaaccct cagagtgcat caaagaattc acactgggga gaaccatttt   1800
aaatgtaacg aatgtgggaa gaatttgtc cggaaagcaa tccttagtga tcatcagaga   1860
attcacacag gggagaaacc ctttcagtgt aataaatgtg ggaaaact               1908
```

<210> SEQ ID NO 55
<211> LENGTH: 375
<212> TYPE: PRT
<213> ORGANISM: Homo sapiens

<400> SEQUENCE: 55

```
Met Gly Cys Arg Arg Thr Arg Glu Gly Pro Ser Lys Ala Met Ile Phe
1               5                   10                  15

Pro Trp Lys Cys Gln Ser Thr Gln Arg Asp Leu Trp Asn Ile Phe Lys
            20                  25                  30

Leu Trp Gly Trp Thr Met Leu Cys Cys Asp Phe Leu Ala His His Gly
        35                  40                  45

Thr Asp Cys Trp Thr Tyr His Tyr Ser Glu Lys Pro Met Asn Trp Gln
    50                  55                  60

Arg Ala Arg Arg Phe Cys Arg Asp Asn Tyr Thr Asp Leu Val Ala Ile
65                  70                  75                  80

Gln Asn Lys Ala Glu Ile Glu Tyr Leu Glu Lys Thr Leu Pro Phe Ser
                85                  90                  95

Arg Ser Tyr Tyr Trp Ile Gly Ile Arg Lys Ile Gly Gly Ile Trp Thr
            100                 105                 110

Trp Val Gly Thr Asn Lys Ser Leu Thr Glu Glu Ala Glu Asn Trp Gly
        115                 120                 125
```

```
Asp Gly Glu Pro Asn Asn Lys Lys Asn Lys Glu Asp Cys Val Glu Ile
    130                 135                 140
Tyr Ile Lys Arg Asn Lys Asp Ala Gly Lys Trp Asn Asp Asp Ala Cys
145                 150                 155                 160
His Lys Leu Lys Ala Ala Leu Cys Tyr Thr Ala Ser Cys Gln Pro Trp
                165                 170                 175
Ser Cys Ser Gly His Gly Glu Cys Val Glu Ile Ile Asn Asn Tyr Thr
            180                 185                 190
Cys Asn Cys Asp Val Gly Tyr Tyr Gly Pro Gln Cys Gln Phe Val Ile
        195                 200                 205
Gln Cys Glu Pro Leu Glu Ala Pro Glu Leu Gly Thr Met Asp Cys Thr
    210                 215                 220
His Pro Leu Gly Asn Phe Ser Phe Ser Ser Gln Cys Ala Phe Ser Cys
225                 230                 235                 240
Ser Glu Gly Thr Asn Leu Thr Gly Ile Glu Glu Thr Thr Cys Gly Pro
                245                 250                 255
Phe Gly Asn Trp Ser Ser Pro Glu Pro Thr Cys Gln Val Ile Gln Cys
            260                 265                 270
Glu Pro Leu Ser Ala Pro Asp Leu Gly Ile Met Asn Cys Ser His Pro
        275                 280                 285
Leu Ala Ser Phe Ser Phe Thr Ser Ala Cys Thr Phe Ile Cys Ser Glu
    290                 295                 300
Gly Thr Glu Leu Ile Gly Lys Lys Lys Thr Ile Cys Glu Ser Ser Gly
305                 310                 315                 320
Ile Trp Ser Asn Pro Ser Pro Ile Cys Gln Lys Leu Asp Lys Ser Phe
                325                 330                 335
Ser Met Ile Lys Glu Gly Asp Tyr Asn Pro Leu Phe Ile Pro Val Ala
            340                 345                 350
Val Met Val Thr Ala Phe Ser Gly Leu Ala Phe Ile Ile Trp Leu Ala
        355                 360                 365
Arg Arg Leu Lys Lys Gly Met
    370                 375

<210> SEQ ID NO 56
<211> LENGTH: 1125
<212> TYPE: DNA
<213> ORGANISM: Homo sapiens

<400> SEQUENCE: 56
atgggctgca gaagaactag agaaggacca agcaaagcca tgatatttcc atggaaatgt      60
cagagcaccc agagggactt atggaacatc ttcaagttgt gggggtggac aatgctctgt     120
tgtgatttcc tggcacatca tggaaccgac tgctggactt accattattc tgaaaaaccc     180
atgaactggc aaagggctag aagattctgc cgagacaatt acacagattt agttgccata     240
caaaacaagg cggaaattga gtatctggag aagactctgc ctttcagtcg ttcttactac     300
tggataggaa tccggaagat aggaggaata tggacgtggg tgggaaccaa caaatctctt     360
actgaagaag cagagaactg gggagatggt gagcccaaca caagaagaa caaggaggac     420 tgcgtggaga tctatatcaa gagaaacaaa gatgcaggca atggaacga tgacgcctgc     480 cacaaactaa aggcagccct ctgttacaca gcttcttgcc agccctggtc atgcagtggc     540
catggagaat gtgtagaaat catcaataat tacacctgca actgtgatgt ggggtactat     600
gggccccagt gtcagtttgt gattcagtgt gagcctttgg aggccccaga gctgggtacc     660
atggactgta ctcaccctt tgggaaactt cagcttcagct cacagtgtgc cttcagctgc     720
```

```
tctgaaggaa caaacttaac tgggattgaa gaaaccacct gtggaccatt tggaaactgg    780
tcatctccag aaccaacctg tcaagtgatt cagtgtgagc ctctatcagc accagatttg    840
gggatcatga actgtagcca tcccctggcc agcttcagct ttacctctgc atgtaccttc    900
atctgctcag aaggaactga gttaattggg aagaagaaaa ccatttgtga atcatctgga    960
atctggtcaa atcctagtcc aatatgtcaa aaattggaca aaagtttctc aatgattaag   1020
gagggtgatt ataaccccct cttcattcca gtggcagtca tggttactgc attctctggg   1080
ttggcattta tcatttggct ggcaaggaga ttaaaaaaag gtatg                   1125
```